US012594368B2

(12) United States Patent
Jansson et al.

(10) Patent No.: US 12,594,368 B2
(45) Date of Patent: Apr. 7, 2026

(54) PERITONEAL DIALYSIS SYSTEM USING DISINFECTION

(71) Applicants: BAXTER INTERNATIONAL INC., Deerfield, IL (US); BAXTER HEALTHCARE SA, Glattpark (CH)

(72) Inventors: Olof Jansson, Vellinge (SE); Mattias Holmer, Lund (SE); Olof Ekdahl, Lund (SE); Innas Forsal, Malmo (SE); Roger Nilsson, Hoor (SE); Henrik Hall, Lund (SE); Bjorn Ericson, Lund (SE); Jonas Alson, Lund (SE); Michael Pettersson, Malmo (SE); Oskar Erik Frode Styrbjorn Fallman, Lund (SE); Jimmie Hansson, Limhamm (SE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 1038 days.

(21) Appl. No.: 17/563,860

(22) Filed: Dec. 28, 2021

(65) Prior Publication Data

US 2022/0203005 A1    Jun. 30, 2022

Related U.S. Application Data

(60) Provisional application No. 63/131,590, filed on Dec. 29, 2020.

(51) Int. Cl.
| | |
|---|---|
| *A61M 1/28* | (2006.01) |
| *A61G 15/18* | (2006.01) |
| *A61M 1/16* | (2006.01) |

(52) U.S. Cl.
CPC ............ *A61M 1/28* (2013.01); *A61M 1/1601* (2014.02); *A61M 1/1658* (2013.01);
(Continued)

(58) Field of Classification Search
CPC .............. A61M 1/1601; A61M 1/1658; A61M 1/1662; A61M 1/1664; A61M 1/1672;
(Continued)

(56) References Cited

U.S. PATENT DOCUMENTS

| | | | |
|---|---|---|---|
| 3,946,731 A * | 3/1976 | Lichtenstein | ......... A61M 1/155 |
| | | | 210/90 |
| 4,439,179 A | 3/1984 | Lueders et al. | |

(Continued)

FOREIGN PATENT DOCUMENTS

| | | |
|---|---|---|
| WO | 2019072384 | 4/2019 |

OTHER PUBLICATIONS

International Search Report and Written Opinion for International Application No. PCT/US2021/065389 dated Jun. 8, 2022.
(Continued)

*Primary Examiner* — John Kim
(74) *Attorney, Agent, or Firm* — K&L Gates LLP

(57) ABSTRACT

A peritoneal dialysis ("PD") system includes a housing; a dialysis fluid pump housed by the housing and including a reusable pump body that accepts PD fluid for pumping; a dialysis fluid inline heater housed by the housing and including a reusable heater body that accepts PD fluid for heating; at least one reusable PD fluid line extending from the housing; at least one disinfection connector supported by the housing and configured to accept one of the at least one reusable PD fluid line; and a control unit configured to run a disinfection sequence after a PD treatment, wherein each of the at least one reusable PD fluid line is connected to one of the at least one disinfection connectors, and wherein at least one of the dialysis fluid pump or the dialysis fluid inline heater is actuated by the control unit during the disinfection sequence.

26 Claims, 33 Drawing Sheets

(52) U.S. Cl.
CPC ........ *A61M 1/1662* (2014.02); *A61M 1/1664*
(2014.02); *A61M 1/1672* (2014.02); *A61M*
*1/168* (2013.01); *A61M 1/1686* (2013.01);
*A61M 1/1688* (2014.02); *A61M 1/282*
(2014.02); *A61M 1/288* (2014.02); *A61G*
*15/18* (2013.01); *A61M 2205/15* (2013.01);
*A61M 2205/3317* (2013.01); *A61M 2205/3331*
(2013.01); *A61M 2205/3344* (2013.01); *A61M*
*2205/3355* (2013.01); *A61M 2205/3368*
(2013.01); *A61M 2205/3379* (2013.01); *A61M*
*2205/3673* (2013.01); *A61M 2205/75*
(2013.01); *A61M 2209/082* (2013.01)

(58) Field of Classification Search
CPC .. A61M 1/168; A61M 1/1686; A61M 1/1688;
A61M 1/28; A61M 1/282; A61M 1/288;
A61M 2205/15; A61M 2205/3317; A61M
2205/3331; A61M 2205/3344; A61M
2205/3355; A61M 2205/3368; A61M
2205/3379; A61M 2205/3673; A61M
2205/75; A61M 2209/082; A01K 89/00;
A01K 89/003; A01K 89/01; A01K
89/0113; A01K 89/015; A61G 15/18
See application file for complete search history.

(56) References Cited

U.S. PATENT DOCUMENTS

| | | | | |
|---|---|---|---|---|
| 4,588,402 | A | 5/1986 | Igari et al. | |
| 8,590,559 | B1* | 11/2013 | Gutierrez | G01M 3/16 200/61.04 |
| 2004/0034334 | A1* | 2/2004 | Ruddell | A61M 1/285 604/6.16 |
| 2009/0012450 | A1 | 1/2009 | Shah | |
| 2016/0236188 | A1 | 8/2016 | Muralikrishna et al. | |
| 2017/0281846 | A1 | 10/2017 | Manda et al. | |
| 2017/0281847 | A1 | 10/2017 | Venkatest et al. | |
| 2018/0021500 | A1 | 1/2018 | Gerber et al. | |
| 2018/0369470 | A1 | 12/2018 | Joseph | |
| 2020/0086028 | A1 | 3/2020 | Norman et al. | |
| 2020/0261638 | A1 | 8/2020 | Lindo et al. | |

OTHER PUBLICATIONS

International Preliminary Report on Patentability, PCT/US2021/065388 mailing date Jan. 31, 2023—7 pages.
International Preliminary Report on Patentability, PCT/US2021/065388 mailing date Mar. 15, 2023—26 pages.

* cited by examiner

PERITONEAL DIALYSIS SYSTEM USING DISINFECTION

PRIORITY CLAIM

The present application claims priority to and the benefit of provisional U.S. Patent Application No. 63/131,590, filed Dec. 29, 2020, entitled "Peritoneal Dialysis Cycler Using Disinfection", the entire contents of which are incorporated herein by reference and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal cavity via a catheter. The dialysis fluid is in contact with the peritoneal membrane in the patient's peritoneal cavity. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

APD is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal cavity of the patient until the start of the next treatment, or may be manually emptied at some point during the day.

In any of the above modalities using an automated machine, the automated machine operates typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an APD machine that reduces disposable waste.

SUMMARY

Known automated peritoneal dialysis ("APD") systems typically include a machine or cycler that accepts and actuates a pumping cassette having a hard part and a soft part that is deformable for performing pumping and valving operations. The hard part is attached to tubes that extend to various bags. The disposable cassette and associated tubes and bags can be cumbersome for a patient at home to load for treatment. The overall amount of disposable items may also lead to multiple setup procedures requiring input from the patient, which can expose room for error.

The present APD system and associated methodology of the present disclosure, on the other hand, converts much of the fluid carrying portions of its PD system into reusable components, which are disinfected after treatment. Fluid lines within the machine or cycler are reused. Disposable items remaining may include a drain line leading to a drain bag or house drain and one or more dialysis fluid container or bag, such as different dextrose or glucose level peritoneal dialysis fluid containers and a last bag container, e.g., containing icodextrine. In an embodiment, a disposable filter is placed at the distal end of the patient line to provide a final stage of PD fluid filtration prior to delivery to the patient.

The APD system of the present disclosure incudes an APD cycler having a housing. At least one and perhaps three or more reusable PD fluid lines extend from the housing. When not connected to PD fluid containers or bags, the reusable PD fluid lines can be connected to disinfection connectors supported and provided by the housing. The reusable PD fluid lines may for example extend from a front of the housing and connect to disinfection connectors also provided at the front of the housing for ready access to the PD fluid lines. The reusable PD fluid lines may be color coded and/or keyed to match a colored or keyed connector of the PD fluid container or bag. The containers or bags may hold different dextrose or glucose level dialysis fluids, such as 1.36% glucose dialysis fluid, 2.27% glucose dialysis fluid, 3.86% glucose dialysis fluid and/or a last bag of a different formulation of PD fluid, such as icodextrin.

Inside the housing, reusable tubing runs from each of the reusable dialysis fluid lines, through a dialysis fluid line valve for each dialysis fluid line to a dialysis fluid inline heater. In an embodiment, each of the valves of the APD cycler is an electrically actuated valve having a reusable valve body that occludes (e.g., when unpowered) or allows (e.g., when powered) PD fluid to flow through the body. The valves may alternatively be bistable valves. The dialysis fluid inline heater is also electrically actuated in one embodiment and is, for example, a resistive heater having a reusable heater body that accepts PD fluid for heating. The inline heater in an embodiment is able to heat PD fluid from room temperature to body temperature, e.g., 37° C., at a flowrate of at least 200 milliliters ("ml")/minute. A temperature sensor is located adjacent to the heater, e.g., downstream from the heater, to provide feedback for temperature control. It is also contemplated to place a second temperature sensor upstream of the heater for feedforward control, which stabilizes and speeds the responsiveness of the heating control. The second sensor may also provide useful information for calculating disinfection dose values, e.g., A0 values, for use during disinfection.

Reusable tubing runs from the outlet of the dialysis fluid inline heater to an air trap in one embodiment. Any of the tubing inside the housing of the cycler may be metal, e.g., stainless steel, or plastic, e.g., polyvinylchloride ("PVC") or a non-PVC material, such as polyethylene ("PE"), cross-linked polyethylene ("PEX"), polyurethane ("PU"), polyetheretherketone ("PEEK") or polycarbonate ("PC"). In an embodiment, one or more level sensor is located adjacent the air trap so that a desired level or range of levels of PD fluid is maintained in the air trap. An air trap valve is located downstream from the air trap in an embodiment, so that the air trap may be closed downstream to fill the air trap. The air trap may be closed upstream by the dialysis fluid line valves for draining. A vent valve may also be provided at the top of the air trap.

A reusable dialysis fluid pump is located within the cycler housing and includes a reusable pump body that accepts PD fluid for pumping. That is, the pump does not require the PD fluid to flow within a disposable item, such as a tube or cassette. The PD fluid pump may be an electrically operated piston, gear, membrane or centrifugal pump, which may be inherently volumetrically accurate so that a separate PD fluid volume measurement apparatus, such as a flowmeter, balance chamber or an apparatus using the ideal gas law, is not needed. The PD fluid pump is controllable to pump to and from the patient at or within a pressure limit by controlling a level of current to, or the speed of, the PD fluid pump. A positive patient pressure limit may for example be one to five psig (e.g., two psig (14 kPa)). A negative patient pressure limit may for example be −1.0 psig to −3.0 psig (e.g., −1.3 psig (−9 kPa)). As discussed herein, where a dual lumen patient line is provided, the lumen not being used for filling or draining the patient may be used as a static pressure line to so that an accurate intraperitoneal patient pressure ("IPP") may be recorded at the cycler and used in the pumping pressure control algorithm or routine for both positive and negative pressures. The PD fluid pump may be bidirectional or unidirectional, and a single pump may be provided. The PD fluid pump may also be continuous. As discussed herein, the patient line is in one embodiment reusable. As such, the pressure drop across it is repeatable from treatment to treatment, which enables the actual pressure at the patient to be known more so than if a different patient line is used for each treatment. Knowing the pressure at the patient instead of estimating same potentially allows for higher flowrates.

In an embodiment, a conductivity sensor is located adjacent to the PD fluid pump. The conductivity sensor may be used to detect the conductivity of the fresh PD fluid to make sure that it is of a prescribed type, e.g., of a prescribed glucose or dextrose level. The conductivity sensor may be used to detect the conductivity of the fresh PD fluid to make sure that it has been mixed correctly, e.g., if an online PD fluid source is connected instead of a PD fluid container to one of the reusable PD fluid lines. The conductivity sensor may also be used to detect the conductivity of the used PD fluid to assess treatment effectiveness and/or look to for patient disease, such as peritonitis. A temperature sensor is located near the conductivity sensor so that the conductivity reading can be temperature compensated.

Parallel patient line valves are located in an embodiment between the conductivity sensor and a reusable patient line. One of the parallel patient line valves selectively allows fresh PD fluid to flow in a fresh PD fluid lumen of a dual lumen reusable patient line, while the other of the parallel patient line valves selectively allows used PD fluid to flow in a used PD fluid lumen of the dual lumen reusable patient line. One or more pressure sensor is located in proximity to the parallel patient line valves to enable positive and negative patient pressures to be monitored and controlled. A patient line connector extends from the APD cycler housing and accepts the dual lumen reusable patient line during disinfection and generally while the patient is not undergoing treatment. A disinfection line located inside the APD cycler housing extends from the patient line connector to the at least one disinfection connector. At least one disinfection line valve is located along the disinfection line to selectively open the disinfection line to run a disinfection sequence. The valves of the present disclosure may be two-way valves, three-way valves or combinations of same.

The drain line is disposable in one embodiment and connects to a drain line connector extending from the housing of the APD cycler during treatment. After treatment, the drain line is removed and discarded. The drain line connector is configured to close or be closed against the outside world when the drain line is removed. The drain line connector includes dual lumens or dialysis fluid pathways that enable disinfection fluid, e.g., heated and used PD fluid, to flow into and out of the drain line connector during disinfection. One lumen or pathway of the drain line connector is placed in selective fluid communication via a first drain line valve with the dialysis fluid pump. The other lumen or pathway of the drain line connector is placed in selective fluid communication via a second drain line valve with the disinfection line.

Besides the dialysis fluid containers or bags and the drain line, another disposable item is a small disposable patient line filter, which is connected between the reusable patient line and the patient's transfer set. The disposable patient line filter, like the reusable patient line, is dual lumen in one embodiment and includes a first or fresh disposable line that communicates with the fresh PD fluid lumen of the dual lumen reusable patient line and a second or used disposable line that communicates with the used PD fluid lumen of the dual lumen reusable patient line. A final stage or sterilizing grade filter membrane is located in the first or fresh disposable line and provides a final stage of PD fluid filtration prior to delivery to the patient. The PD filter membrane can for example be a pass-through filter that does not have a reject line. Pore sizes for the sterilizing grade filter membrane may, for example, be less than a micron, such as 0.1 or 0.2 micron. Negative pressure is applied to the used disposable line to remove used dialysis fluid or effluent to drain.

An alternative single lumen reusable line may be used with an alternative single lumen disposable patient line filter. The alternative single lumen disposable patient line filter may be provided with a check valve to ensure that all fresh PD fluid is forced through the sterilizing grade filter.

In one embodiment, a spool or hose reel is located within the housing. The hose reel is configured to automatically retract the reusable patient line when the patient line is connected to the patient line connector. The spool includes a releasable lock, e.g., activated by an actuator or button, which the user opens to allow the spool to coil the patient line. Until the lock is released or opened, the patient line remains uncoiled from the spool so that the spool does not pull on the reusable patient line during treatment.

Any of the cyclers described herein may be provided with a flow switch (or flow sensor) located on the suction side of the PD fluid pump (from a patient filling standpoint) to sense when a PD fluid container or bag may be running low. The flow switch is useful during treatment as a safety check, after treatment when finally draining each of the PD fluid containers or bags, and at the beginning of disinfection when filling the cycler with fresh PD fluid for the disinfection. An additional pressure sensor may be located on the suction side of the PD fluid pump (from a patient filling standpoint) to sense the inlet negative pressure to the pump. The additional pressure sensor is also useful to detect an empty or almost empty PD fluid container or bag and may therefore be used alternatively or in addition to the flow switch. The output from the additional pressure sensor may also be used in determining a volume of PD fluid pumped in a pump stroke for a type of PD fluid pump that depends on incoming pressure for accuracy. A leak detection pan may also be provided at the bottom of the cycler housing and operate with a leak detection sensor. The leak detection pan is formed to have an angle or funnel shape, which collects any type of fluid that falls from the reusable tubing of the cycler due to a faulty connection, ruptured material, or other reason. The leak detection sensor may be ultrasonic, inductive, capacitive, optical, and/or directly contact the leaked material, e.g., include an electrical contact closure. Upon receiving a fluid leak signal from the leak detection sensor, the cycler control unit alarms and undertakes any specified corrective action.

The APD cycler of the APD system of the present disclosure includes a control unit having one or more processor and one or more memory that receive signals or outputs from the pressure sensors, temperature sensors, conductivity sensor, flow switch and leak detection sensor and process the signals or outputs as feedback. The control unit uses pressure feedback to control the dialysis fluid pump to run at safe patient pressure limits during treatment and safe system limits during disinfection. The control unit uses temperature feedback to control the dialysis fluid heater to heat the fresh dialysis fluid to, e.g., body temperature, and to heat unused fresh PD fluid to a disinfection temperature after treatment for a disinfection sequence. The control unit uses the temperature compensated conductivity readings to analyze fresh and/or used dialysis fluid for the reasons discussed herein.

The control unit also opens and closes the dialysis fluid valves in combination with the dialysis fluid pump and heater to run a priming sequence, a patient fill sequence, a patient drain sequence and a disinfection sequence after a PD treatment, wherein each of the at least one reusable PD fluid line is connected to one of the at least one disinfection connectors, and wherein the reusable patient line is connected to the reusable patient line connector. The disinfection sequence readies the APD cycler for the next treatment. In an embodiment, used dialysis fluid is heated after the final drain and is used for disinfection.

In an alternative embodiment, the cycler stores water in a water tank, which is used instead for disinfection. The cycler may also include a cleaning cartridge, e.g., a sorbent cartridge, which cleans the water after disinfection. The cleaned water is returned to the water tank for the next treatment. An alternative single lumen reusable line may be used with an alternative single lumen disposable patient line filter, which may be provided with a check valve to ensure that all fresh PD fluid is forced through the sterilizing grade filter.

It is contemplated to provide any of the systems described herein with a periodic citric acid (which may or may not be heated) disinfection. The citric acid disinfection helps to remove and hinder the growth of biofilm (concentrated NaCl may be used alternatively or additionally against biofilm), endotoxin residuals, and precipitation that may have formed during treatment.

It is also contemplated to provide a flush flow subsystem for supplying water to the inherently accurate dialysis fluid pump for lubrication. In the system embodiment provided herein having a water tank, it is contemplated to place the lubrication-needing portion of the dialysis fluid pump in fluid communication with a standing water column provided via the water tank or with a pumped water recirculation line extending from and back to the water tank. In the system embodiments provided herein that use dialysis fluid for disinfection, the flush flow subsystem in one embodiment includes a water production subsystem in which a small portion of the dialysis fluid is distilled in the inline dialysis fluid heater, e.g., at the end of disinfection. The distillation heats or boils off glucose or dextrose from the dialysis fluid to produce distilled water vapor, e.g., in the air trap. The residual glucose or dextrose remains in the dialysis fluid that is not vaporized. The distilled water is cooled, for example, via a fan and/or a cooler, e.g., a thermoelectric cooler such as a Peltier module. The thermoelectric cooler is in one embodiment integrated with a reusable air trap provided with the cycler. Alternatively, passive cooling such as heat fins may be used because the volume of water needed is small, e.g., a few milliliters. The cooled water is collected in a small chamber. As with the water tank, it is contemplated to place the lubrication-needing portion of the dialysis fluid pump in fluid communication with a standing water column provided via the small chamber or with a pumped water recirculation line extending from, and back to, the small chamber.

In light of the disclosure set forth herein, and without limiting the disclosure in any way, in a first aspect of the present disclosure, which may be combined with any other aspect, or portion thereof, a peritoneal dialysis ("PD") system includes a housing; a dialysis fluid pump housed by the housing and including a reusable pump body that accepts PD fluid for pumping; a dialysis fluid inline heater housed by the housing and including a reusable heater body that accepts PD fluid for heating; at least one reusable PD fluid line extending from the housing; at least one disinfection connector supported by the housing and configured to accept one of the at least one reusable PD fluid line; and a control unit configured to run a disinfection sequence after a PD treatment, wherein each of the at least one reusable PD fluid line is connected to one of the at least one disinfection connectors, and wherein at least one of the dialysis fluid pump and the dialysis fluid inline heater is actuated during the disinfection sequence.

In a second aspect of the present disclosure, which may be combined with any other aspect, or portion thereof, the control unit is configured to cause (i) the dialysis fluid inline heater to heat the PD fluid to at least 70° C. and (ii) the dialysis fluid pump to recirculate the heated PD fluid during the disinfection sequence.

In a third aspect of the present disclosure, which may be combined with any other aspect, or portion thereof, the dialysis fluid pump is a piston, gear, membrane or centrifugal pump, the reusable pump body of the piston, gear, membrane or centrifugal pump accepting PD fluid for pumping.

In a fourth aspect of the present disclosure, which may be combined with any other aspect described herein, or portion thereof, the dialysis fluid pump is volumetrically inherently accurate.

In a fifth aspect of the present disclosure, which may be used with any other aspect, or portion thereof, the PD system includes a pressure sensor located downstream from the dialysis fluid pump, the pressure sensor providing pressure feedback to the control unit, the pressure feedback used by the control unit to control a pressure of the PD fluid pumped by the dialysis fluid pump.

In a sixth aspect of the present disclosure, which may be combined with any other aspect, or portion thereof, the control unit controls electrical current to the dialysis fluid pump to control the pressure of the PD fluid.

In a seventh aspect of the present disclosure, which may be combined with any other aspect, or portion thereof, the PD system includes a temperature sensor located downstream from the dialysis fluid inline heater, the temperature sensor providing temperature feedback to the control unit, the temperature feedback used by the control unit to control a temperature of the PD fluid heated by the dialysis fluid inline heater.

In an eighth aspect of the present disclosure, which may be combined with any other aspect, or portion thereof, the PD system includes an air trap located downstream from the dialysis fluid inline heater, the air trap configured to collect air removed from dialysis fluid heated by the dialysis fluid inline heater and/or from a PD fluid container.

In a ninth aspect of the present disclosure, which may be combined with any other aspect, or portion thereof, the PD system includes at least one level sensor positioned and arranged to detect dialysis fluid within the air trap, the at least one level sensor providing an output to the control unit, the control unit configured to use the output to control a dialysis fluid level within the air trap.

In a tenth aspect of the present disclosure, which may be combined with any other aspect, or portion thereof, the PD system includes a conductivity sensor in fluid communication with the dialysis fluid pump, the conductivity sensor providing an output to the control unit, the control unit configured to use the output to at least one of (i) ensure fresh PD fluid is of a prescribed type or (ii) analyze used PD fluid for treatment effectiveness and/or patient disease.

In an eleventh aspect of the present disclosure, which may be combined with any other aspect, or portion thereof, the PD system includes a plurality of dialysis fluid valves, each dialysis fluid valve including a reusable valve body that occludes or allows PD fluid to flow through the reusable valve body, the plurality of valves including at least one of (i) at least one first valve between each of the at least one reusable PD fluid lines and the dialysis fluid inline heater, (ii) a second valve between the dialysis fluid inline heater and the dialysis fluid pump, or (iii) at least one third valve provided along a disinfection line in fluid communication with the at least one disinfection connector.

In a twelfth aspect of the present disclosure, which may be combined with any other aspect, or portion thereof, the PD system includes at least one of a reusable patient line or reusable drain line and at least one of (i) a patient line connector, the patient line connector supported by the housing, the patient line connector configured to accept the reusable patient line for running the disinfection sequence or (ii) a drain line connector, the drain line connector supported by the housing, the drain line connector configured to accept the reusable drain line for running the disinfection sequence.

In a thirteenth aspect of the present disclosure, which may be combined with any other aspect, or portion thereof, the reusable patient line is a dual lumen patient line.

In a fourteenth aspect of the present disclosure, which may be combined with any other aspect, or portion thereof, the PD system includes a disposable filter set configured to interface between the reusable patient line and a patient's transfer set, the disposable filter set providing a final stage of PD fluid filtration prior to delivery to the patient, and wherein the final stage of PD fluid filtration is optionally sterile filtration.

In a fifteenth aspect of the present disclosure, which may be combined with any other aspect, or portion thereof, at least one of (i) the reusable patient line when plugged into the patient line connector forms part of a disinfection loop for the disinfection sequence or (ii) the reusable patient line is coated with a non-sticking or smooth coating.

In a sixteenth aspect of the present disclosure, which may be combined with any other aspect, or portion thereof, the disinfection loop further includes at least one of (i) a first fluid line leading from the at least one reusable PD fluid line to the reusable heater body, (ii) a second fluid line leading from the reusable heater body to the reusable pump body, or (iii) a third fluid line leading from the reusable pump body to the reusable patient line.

In a seventeenth aspect of the present disclosure, which may be combined with any other aspect, or portion thereof, the PD system includes at least one spool located within the housing, the at least one spool configured to automatically retract at least one of (i) the reusable patient line when the patient line is connected to the patient line connector or (ii) the reusable drain line when the drain line is connected to the drain line connector.

In an eighteenth aspect of the present disclosure, which may be combined with any other aspect, or portion thereof, the PD system includes a dual lumen connector allowing a disinfection loop to be formed with an associated line removed from the connector, wherein the connector is optionally a drain line connector.

In a nineteenth aspect of the present disclosure, which may be combined with any other aspect, or portion thereof, the PD system includes a source of flush flow fluid and at least one flush flow line for communicating the flush flow fluid from the source to the dialysis fluid pump, wherein the source of flush flow fluid includes a mechanism to heat PD fluid to form steam or water vapor, and a condenser for condensing the steam or water vapor into the flush flow fluid.

In a twentieth aspect of the present disclosure, which may be combined with any other aspect, or portion thereof, the PD system includes at least one of a flow switch or a pressure sensor positioned between the dialysis fluid pump and the at least one reusable PD fluid line, and wherein the control unit is configured to use at least one output from the at least one flow switch or pressure sensor to detect an empty or no flow condition of a PD fluid container in fluid communication with one of the at least one reusable PD fluid line.

In a twenty-first aspect of the present disclosure, which may be combined with any other aspect, or portion thereof, the control unit is further configured to use an output from the pressure sensor in a fluid volume delivered determination for the dialysis fluid pump.

In a twenty-second aspect of the present disclosure, which may be combined with any other aspect, or portion thereof, a peritoneal dialysis ("PD") system includes a housing; a dialysis fluid pump housed by the housing and including a reusable pump body that accepts PD fluid for pumping; a dialysis fluid inline heater housed by the housing and including a reusable heater body that accepts PD fluid for heating; a reusable patient line extending from the housing; a patient line connector supported by the housing, the patient line connector configured to accept the patient line for running the disinfection sequence; and a control unit configured to run a disinfection sequence after a PD treatment, wherein the reusable patient line is connected to the patient line connector, and wherein the dialysis fluid pump and the dialysis fluid inline heater are actuated during the disinfection sequence.

In a twenty-third aspect of the present disclosure, which may be combined with any other aspect, or portion thereof, the control unit is configured to cause (i) the dialysis fluid inline heater to heat the PD fluid to at least 70° C. and (ii) the dialysis fluid pump to recirculate the heated PD fluid during the disinfection sequence.

In a twenty-fourth aspect of the present disclosure, which may be combined with any other aspect, or portion thereof, the PD system includes a disposable filter set configured to interface between the reusable patient line and a patient's transfer set, the disposable patient filter set providing at least one of (i) a final stage of PD fluid filtration prior to delivery to the patient, wherein the final stage of PD fluid filtration is optionally sterile filtration, or (ii) a final stage of air removal from the PD fluid prior to delivery to the patient.

In a twenty-fifth aspect of the present disclosure, which may be combined with any other aspect, or portion thereof, the disposable filter set includes a final stage filter located along a first disposable line and which includes a second disposable line operating in parallel with the first disposable line.

In a twenty-sixth aspect of the present disclosure, which may be combined with any other aspect, or portion thereof, the reusable patient line is a dual lumen patient line including a first lumen in fluid communication with the first disposable line and a second lumen in fluid communication with the second disposable line.

In a twenty-seventh aspect of the present disclosure, which may be combined with any other aspect, or portion thereof, the PD system includes a source of flush flow fluid and at least one flush flow line for communicating the flush flow fluid from the source to the dialysis fluid pump.

In a twenty-eighth aspect of the present disclosure, which may be combined with any other aspect, or portion thereof, the PD includes a leak detection sensor and a leak detection pan located at the bottom of the housing, the leak detection pan formed so as to collect leaked PD fluid at a location detectable by the leak detection sensor.

In a twenty-ninth aspect of the present disclosure, which may be combined with any other aspect, or portion thereof, a peritoneal dialysis ("PD") system includes a housing; a dialysis fluid pump or a flush fluid pump housed by the housing; a dialysis fluid heater housed by the housing; at least one reusable PD fluid line extending from the housing; at least one disinfection connector supported by the housing and configured to accept one of the at least one reusable PD fluid line; a cleaning cartridge; and a control unit configured to run (i) a disinfection sequence after a PD treatment, wherein each of the at least one reusable PD fluid line is connected to one of the at least one disinfection connectors, and wherein the dialysis fluid pump pumps water heated by the dialysis fluid heater during the disinfection sequence, and (ii) a water cleaning sequence before or after the disinfection sequence, wherein the dialysis fluid pump or the flush fluid pump pumps disinfection water through the cleaning cartridge for use in a subsequent disinfection sequence.

In a thirtieth aspect of the present disclosure, which may be combined with any other aspect, or portion thereof, the dialysis fluid pump includes a reusable pump body that accepts PD fluid and water for pumping.

In a thirty-first aspect of the present disclosure, which may be combined with any other aspect, or portion thereof, the dialysis fluid heater is an inline heater that includes a reusable heater body that accepts PD fluid and water for heating.

In a thirty-second aspect of the present disclosure, which may be combined with any other aspect, or portion thereof, the PD system includes a water tank for holding disinfection water for the disinfection sequence.

In a thirty-third aspect of the present disclosure, which may be combined with any other aspect, or portion thereof, the PD system includes at least one level sensor positioned and arranged to detect a level of water in the water tank, the at least one level sensor providing an output to the control unit, the control unit configured to use the output to monitor a disinfection water level within the water tank.

In a thirty-fourth aspect of the present disclosure, which may be combined with any other aspect, or portion thereof, the cleaning cartridge is a sorbent cartridge that holds at least activated carbon.

In a thirty-fifth aspect of the present disclosure, which may be combined with any other aspect, or portion thereof, the cleaning sequence is configured to pump disinfection water that has been used for disinfection at least one time through the cleaning cartridge for use in a subsequent disinfection sequence.

In a thirty-sixth aspect of the present disclosure, which may be combined with any other aspect, or portion thereof, a peritoneal dialysis ("PD") system includes a housing; a dialysis fluid pump or a flush fluid pump housed by the housing; a dialysis fluid heater housed by the housing; a reusable patient line extending from the housing; a patient line connector supported by the housing, the patient line connector configured to accept the patient line for running the disinfection sequence; a cleaning cartridge; and a control unit configured to run (i) a disinfection sequence after a PD treatment, wherein the reusable patient line is connected to the patient line connector, and wherein the dialysis fluid pump pumps water heated by the dialysis fluid heater during the disinfection sequence, and (ii) a water cleaning sequence before or after the disinfection sequence, wherein the dialysis fluid pump or the flush fluid pump pumps disinfection water through the cleaning cartridge for use in a subsequent disinfection sequence.

In a thirty-seventh aspect of the present disclosure, which may be combined with any other aspect, or portion thereof, the PD system includes a disposable filter set configured to interface between the reusable patient line and a patient's transfer set, the disposable filter set providing a final stage of PD fluid filtration prior to delivery to the patient.

In a thirty-eighth aspect of the present disclosure, which may be combined with any other aspect, or portion thereof, the reusable patient line is single lumen and the disposable filter set includes a check valve oriented to force fresh dialysis fluid through a sterilizing grade filter of the disposable filter set.

In a thirty-ninth aspect of the present disclosure, which may be combined with any other aspect, or portion thereof, the PD system includes at least one spool located within the housing, the at least one spool configured (i) to automatically retract the reusable patient line when the reusable patient line is connected to the patient line connector or (ii) to automatically retract a reusable drain line when the reusable drain line is connected to a drain line connector.

In a fortieth aspect of the present disclosure, which may be combined with any other aspect, or portion thereof, a peritoneal dialysis ("PD") system includes a housing; a dialysis fluid pump housed by the housing; a dual lumen patient line extending from the housing; a filter set including a filter membrane positioned and arranged to filter fresh PD fluid entering from a first line of the filter set, and which includes a second line in parallel with the first line, the first line in fluid communication with a first lumen of the dual lumen patient line, and the second line in fluid communication with a second lumen of the dual lumen patient line; a pressure sensor located within the housing and positioned so as to sense a static or substantially static PD fluid pressure in the second lumen while fresh PD fluid is pumped through the first lumen and the filter membrane; and a control unit configured to use the sensed static or substantially static PD fluid pressure in a pressure control routine for the dialysis fluid pump.

In a forty-first aspect of the present disclosure, which may be combined with any other aspect, or portion thereof, the filter membrane traps air from the PD fluid and is vented to release trapped air to atmosphere.

In a forty-second aspect of the present disclosure, which may be combined with any other aspect, or portion thereof, the pressure sensor is a first pressure sensor, and which includes a second, safety pressure sensor positioned so as to sense the static or substantially static PD fluid pressure in the second lumen while fresh PD fluid is pumped through the first lumen and the filter membrane.

In a forty-third aspect of the present disclosure, which may be combined with any other aspect, or portion thereof, the pressure sensor is a first pressure sensor, and which includes a second pressure sensor positioned so as to sense positive PD fluid pressure prior to entering the first lumen of the dual lumen patient line, the control unit configured to use the sensed pressure from the second pressure sensor in the pressure control routine for the dialysis fluid pump.

In a forty-fourth aspect of the present disclosure, which may be combined with any other aspect, or portion thereof, the second pressure sensor is used additionally to sense static or substantially static negative PD fluid pressure in the first lumen while used PD fluid is pulled through the second lumen of the dual lumen patient line.

In a forty-fifth aspect of the present disclosure, which may be combined with any other aspect, or portion thereof, the control unit is configured to use the sensed static or substantially static negative PD fluid pressure in the pressure control routine for the dialysis fluid pump.

In a forty-sixth aspect of the present disclosure, which may be combined with any other aspect, or portion thereof, the first pressure sensor is used additionally to detect a negative pressure of used PD fluid entering the housing from the second lumen of the dual lumen patient line.

In a forty-seventh aspect of the present disclosure, which may be combined with any other aspect, or portion thereof, the first and second lines of the filter set converge at a location for fluid communication with a patient catheter, the static or substantially static PD fluid pressure extending from the location, through the second line of the filter set and the second lumen of the dual lumen patient line, to at least one closed valve within the housing, and wherein the pressure sensor is located between the at least one closed valve and the second lumen of the dual lumen patient line.

In a forty-eighth aspect of the present disclosure, which may be combined with any other aspect, or portion thereof, the first and second lines of the filter set converge at a location for fluid communication with a patient catheter, the static or substantially static PD fluid pressure extending from the location, through the first line of the filter set and the first lumen of the dual lumen patient line, to at least one closed valve within the housing.

In a forty-ninth aspect of the present disclosure, which may be combined with any other aspect, or portion thereof, a peritoneal dialysis ("PD") system includes: a housing; a dialysis fluid pump housed by the housing and including a reusable pump body that accepts PD fluid for pumping, the dialysis fluid pump including at least one flush flow port; a dialysis fluid heater for heating the PD fluid; a container configured to accept and hold PD fluid; a condenser in fluid communication with the container; a chamber in fluid communication with the condenser; at least one flush flow line extending from the chamber to the at least one flush flow port; and a control unit programmed cause the dialysis fluid heater to heat PD fluid in the container to form steam or water vapor, wherein the steam or water vapor is condensed in the condenser into distilled water collected in the chamber and provided from the chamber to the at least one flush flow port via the at least one flush flow line.

In a fiftieth aspect of the present disclosure, which may be combined with any other aspect, or portion thereof, the dialysis fluid heater is an inline dialysis fluid heater housed by the housing and including a reusable heater body that accepts PD fluid for heating.

In a fifty-first aspect of the present disclosure, which may be combined with any other aspect, or portion thereof, the container includes an air trap operable with at least one level sensor outputting to the control unit.

In a fifty-second aspect of the present disclosure, which may be combined with any other aspect, or portion thereof, the control unit is configured to confirm that the at least one level sensor senses PD fluid within the air trap prior to causing the dialysis fluid heater to heat PD fluid.

In a fifty-third aspect of the present disclosure, which may be combined with any other aspect, or portion thereof, the condenser includes a fan and a fluid carrying structure that forces the steam or water vapor air to remain in an air flow area of the fan.

In a fifty-fourth aspect of the present disclosure, which may be combined with any other aspect, or portion thereof, the condenser includes a thermoelectric cooler configured to condense steam or water vapor within a condensing pathway.

In a fifty-fifth aspect of the present disclosure, which may be combined with any other aspect, or portion thereof, the condensing pathway extends through or is in thermal communication with a cooled side of the thermoelectric cooler.

In a fifty-sixth aspect of the present disclosure, which may be combined with any other aspect, or portion thereof, the PD system includes a fan positioned and arranged to blow air towards a warmed side of the thermoelectric cooler.

In a fifty-seventh aspect of the present disclosure, which may be combined with any other aspect, or portion thereof, the PD system includes a return line from the chamber, the return line enabling excess distilled water to return to the container.

In a fifty-eighth aspect of the present disclosure, which may be combined with any other aspect, or portion thereof, the return line extends to a steam line extending from the container to the condenser.

In a fifty-ninth aspect of the present disclosure, which may be combined with any other aspect, or portion thereof, the return line extends to the container.

In a sixtieth aspect of the present disclosure, which may be combined with any other aspect, or portion thereof, the PD system includes a flow restrictor located along the return line to initially resist distilled water flow through the flow restrictor until at least the chamber is filled.

In a sixty-first aspect of the present disclosure, which may be combined with any other aspect, or portion thereof, the condenser includes a thermoelectric cooler including a warmed side and a cooled side, and wherein the thermoelectric cooler is positioned such that the warmed side additionally heats the PD fluid and the cooled side condenses the steam or water vapor.

In a sixty-second aspect of the present disclosure, which may be combined with any other aspect, or portion thereof, the at least one flush flow line is positioned and arranged to enable the distilled water to statically contact a lubrication-needing portion of the dialysis fluid pump via the at least one flush flow port.

In a sixty-third aspect of the present disclosure, which may be combined with any other aspect, or portion thereof, the PD system includes a small pump positioned and arranged to pump distilled water through the at least one flush flow line and the at least one flush flow port.

In a sixty-fourth aspect of the present disclosure, which may be combined with any other aspect, or portion thereof, the PD system includes a steam valve located between the container and the condenser.

In a sixty-fifth aspect of the present disclosure, which may be combined with any other aspect, or portion thereof, the control unit is configured to maintain the steam valve closed during treatment and priming.

In a sixty-sixth aspect of the present disclosure, which may be combined with any other aspect, or portion thereof, the control unit is configured to open the steam valve prior to causing the dialysis fluid heater to heat PD fluid in the container to form steam, the opened steam valve enabling residual distilled water to flow from the chamber to the container.

In a sixty-seventh aspect of the present disclosure, which may be combined with any other aspect, or portion thereof, the control unit is configured to cause the dialysis fluid heater to heat PD fluid at the end of a disinfection sequence for disinfecting at least the reusable pump body of the dialysis fluid pump.

In a sixty-eighth aspect of the present disclosure, which may be combined with any other aspect, or portion thereof, at least one of the condenser and chamber are provided with the container.

In a sixty-ninth aspect of the present disclosure, which may be combined with any other aspect, or portion thereof, a peritoneal dialysis ("PD") system includes a housing; a dialysis fluid pump housed by the housing and including a reusable pump body that accepts PD fluid for pumping, the dialysis fluid pump including at least one flush flow port; a dialysis fluid heater for heating the PD fluid; a container including a primary chamber configured to accept and hold PD fluid, the container including a condenser and a water chamber; at least one flush flow line extending from the water chamber to the at least one flush flow port; and a control unit programmed cause the dialysis fluid heater to heat PD fluid in the container to form steam or water vapor, wherein the steam or water vapor is condensed by the condenser into distilled water collected in the water chamber and provided from the water chamber to the at least one flush flow port via the at least one flush flow line.

In a seventieth aspect of the present disclosure, which may be combined with any other aspect, or portion thereof, the condenser includes a thermoelectric cooler positioned and arranged to condense the steam or water vapor.

In a seventy-first aspect of the present disclosure, which may be combined with any other aspect, or portion thereof, the condenser is positioned and arranged elevationally in use above the water chamber.

In a seventy-second aspect of the present disclosure, which may be combined with any other aspect, or portion thereof, the condenser is angled in use so that condensed water gravity flows along the condenser.

In a seventy-third aspect of the present disclosure, which may be combined with any other aspect, or portion thereof, a peritoneal dialysis ("PD") system includes a housing; a dialysis fluid pump housed by the housing; a dual lumen patient line extending from the housing; a filter set including a filter membrane positioned and arranged to filter fresh PD fluid entering from a first line of the filter set, and which includes a second line in parallel with the first line, the first line in fluid communication with a first lumen of the dual lumen patient line, and the second line in fluid communication with a second lumen of the dual lumen patient line; a pressure sensor located within the housing and positioned so as to sense a static or substantially static positive PD fluid pressure in the second lumen while fresh PD fluid is pumped through the first lumen and the filter membrane; and at least one closed valve located within the housing, the static or substantially static positive PD fluid pressure extending to the at least one closed valve, and wherein the pressure sensor is located between the at least one closed valve and the second lumen of the dual lumen patient line.

In a seventy-fourth aspect of the present disclosure, which may be combined with any other aspect, or portion thereof, the first and second lines of the filter set converge at a location for fluid communication with a patient catheter, the static or substantially static positive PD fluid pressure extending from the location, through the second line of the filter set and the second lumen of the dual lumen patient line, to the at least one closed valve.

In a seventy-fifth aspect of the present disclosure, which may be combined with any other aspect, or portion thereof, the pressure sensor is a first pressure sensor, and the at least one closed valve is a first at least one valve closed while fresh PD fluid is pumped by the dialysis fluid pump, and which includes a second pressure sensor positioned within the housing so as to sense a static or substantially static negative PD fluid pressure in the first lumen while used PD fluid is pumped through the second lumen.

In a seventy-sixth aspect of the present disclosure, which may be combined with any other aspect, or portion thereof, the PD system includes a second at least one valve closed while used PD fluid is pumped, and wherein the second pressure sensor is located between the second at least one closed valve and the first lumen of the dual lumen patient line.

In a seventy-seventh aspect of the present disclosure, which may be combined with any other aspect, or portion thereof, the PD system includes a control unit, and wherein at least one of the sensed static or substantially static positive PD fluid pressure or the sensed static or substantially static negative PD fluid pressure is used as feedback in a pressure control routine performed by the control unit for the dialysis fluid pump.

In a seventy-eighth aspect of the present disclosure, which may be combined with any other aspect, or portion thereof, the first and second lines of the filter set converge at a location for fluid communication with a patient catheter, the static or substantially static negative pressure extending from the location, through the first line of the filter set and the first lumen of the dual lumen patient line, to the second at least one closed valve.

In a seventy-ninth aspect of the present disclosure, which may be combined with any other aspect, or portion thereof, a peritoneal dialysis ("PD") method includes providing a dual lumen patient line including a first lumen and a second lumen; providing a filter set including a filter membrane positioned and arranged to filter fresh PD fluid entering from a first line of the filter set, the filter set including a second line in parallel with the first line, the first line in fluid communication with the first lumen of the dual lumen patient line, and the second line in fluid communication with the second lumen of the dual lumen patient line; positioning a pressure sensor so as to sense a static or substantially static positive PD fluid pressure in the second lumen while fresh PD fluid is pumped through the first lumen and the filter membrane; and configuring a control unit to use the sensed static or substantially static positive PD fluid pressure in a pressure control routine for regulating fresh dialysis fluid pressure.

In an eightieth aspect of the present disclosure, which may be combined with any other aspect, or portion thereof, positioning the pressure sensor includes locating the pressure sensor between the second lumen of the dual lumen patient line and at least one closed valve.

In an eighty-first aspect of the present disclosure, which may be combined with any other aspect, or portion thereof, the pressure sensor is a first pressure sensor, and which includes positioning a second pressure sensor so as to sense a static or substantially static negative PD fluid pressure in the first lumen while used PD fluid is pumped through the second lumen of the dual lumen patient line.

In an eighty-second aspect of the present disclosure, which may be combined with any other aspect, or portion thereof, the PD method includes further configuring the control unit to use the sensed static or substantially static negative PD fluid pressure in the pressure control routine for regulating used dialysis fluid pressure.

In an eighty-third aspect of the present disclosure, which may be used with any other aspect, or portion thereof, a peritoneal dialysis ("PD") system includes a housing; a dialysis fluid pump housed by the housing; a patient line extendable from the housing; and a hose reel located within the housing, the hose reel configured to coil the patient line when disconnected from a patient.

In an eighty-fourth aspect of the present disclosure, which may be used with any other aspect, or portion thereof, the patient line is a dual lumen patient line, and wherein the dual lumen patient line is coiled about the hose reel during a disinfection sequence for disinfecting the dual lumen patient line and the dialysis fluid pump.

In an eighty-fifth aspect of the present disclosure, which may be used with any other aspect, or portion thereof, the PD system includes a patient line connector including a lumen that allows disinfection fluid communication between first and second lumens of the dual lumen patient line when the patient line connector is connected to the dual lumen patient line.

In an eighty-sixth aspect of the present disclosure, which may be used with any other aspect, or portion thereof, the patient line connector is pulled into a docking port provided by the housing when the dual lumen patient line is coiled by the hose reel.

In an eighty-seventh aspect of the present disclosure, which may be used with any other aspect, or portion thereof, the PD system includes a cavity provided by housing for storing the patient line connector when removed from the dual lumen patient line.

In an eighty-eighth aspect of the present disclosure, which may be used with any other aspect, or portion thereof, the PD system is configured to perform a disinfection sequence, and wherein the hose reel includes at least one rotating fluid pathway forming part of a disinfection circuit with the dialysis fluid pump and the patient line.

In an eighty-ninth aspect of the present disclosure, which may be used with any other aspect, or portion thereof, the at least one rotating fluid pathway is in fluid communication with at least one fixed fresh PD fluid line or fixed used PD fluid line via at least one rotating seal, and wherein the at least one fixed fresh or fixed used PD fluid line is located within the housing.

In a ninetieth aspect of the present disclosure, which may be used with any other aspect, or portion thereof, the patient line when extended from the housing is held in place by a releasable lock.

In a ninety-first aspect of the present disclosure, which may be used with any other aspect, or portion thereof, the PD system includes an actuator configured to be actuated operable by the patient or user to release the releasable lock, allowing the hose reel to coil the patient line within the housing.

In a ninety-second aspect of the present disclosure, which may be used with any other aspect, or portion thereof, the actuator is a momentary actuator configured such that the patient line is coiled by the hose reel only when the actuator is actuated by the patient or user.

In a ninety-third aspect of the present disclosure, which may be used with any other aspect, or portion thereof, the hose reel includes a rotating connector, wherein one end of the patient line is connected to the rotating connector.

In a ninety-fourth aspect of the present disclosure, which may be used with any other aspect, or portion thereof, any of the features, functionality and alternatives described in connection with any one or more of FIGS. 1 to 34 may be combined with any of the features, functionality and alternatives described in connection with any other of FIGS. 1 to 34.

It is accordingly an advantage of the present disclosure to provide an automated peritoneal dialysis ("APD") cycler that reuses many components that may otherwise be disposable.

It is another advantage of the present disclosure to provide an ("APD") cycler having fluid handling components that accept peritoneal dialysis fluid directly without having to operate with a disposable item, such as a tube or flexible sheeting.

It is a further advantage of the present disclosure to provide an ("APD") cycler that uses unused treatment fluid during disinfection.

It is yet another advantage of the present disclosure to provide a volumetrically accurate APD cycler.

It is yet a further advantage of the present disclosure to provide an APD cycler having fluid pressure controlled pumping to and from the patient.

It is still another advantage of the present disclosure to provide a relatively quiet APD cycler.

It is still a further advantage of the present disclosure to provide a relatively simple disposable set.

Moreover, it is an advantage of the present disclosure to provide a dual lumen patient line that enables patient fills to occur without an, or with a minimal, initial delivery of used PD fluid back into the patient and for patient drains to occur without an, or with a minimal, initial delivery of fresh PD fluid to drain.

SUMMARY

Additional features and advantages are described in, and will be apparent from, the following Detailed Description and Drawings. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE DRAWINGS

FIGS. 31 and 32 are schematic views of an alternative APD cycler and system using water for disinfection, wherein the disinfection water is cleaned for a subsequent disinfection and is used for a PD fluid pump flush flow.

DETAILED DESCRIPTION

PD Fluid Disinfection

Figure 1:
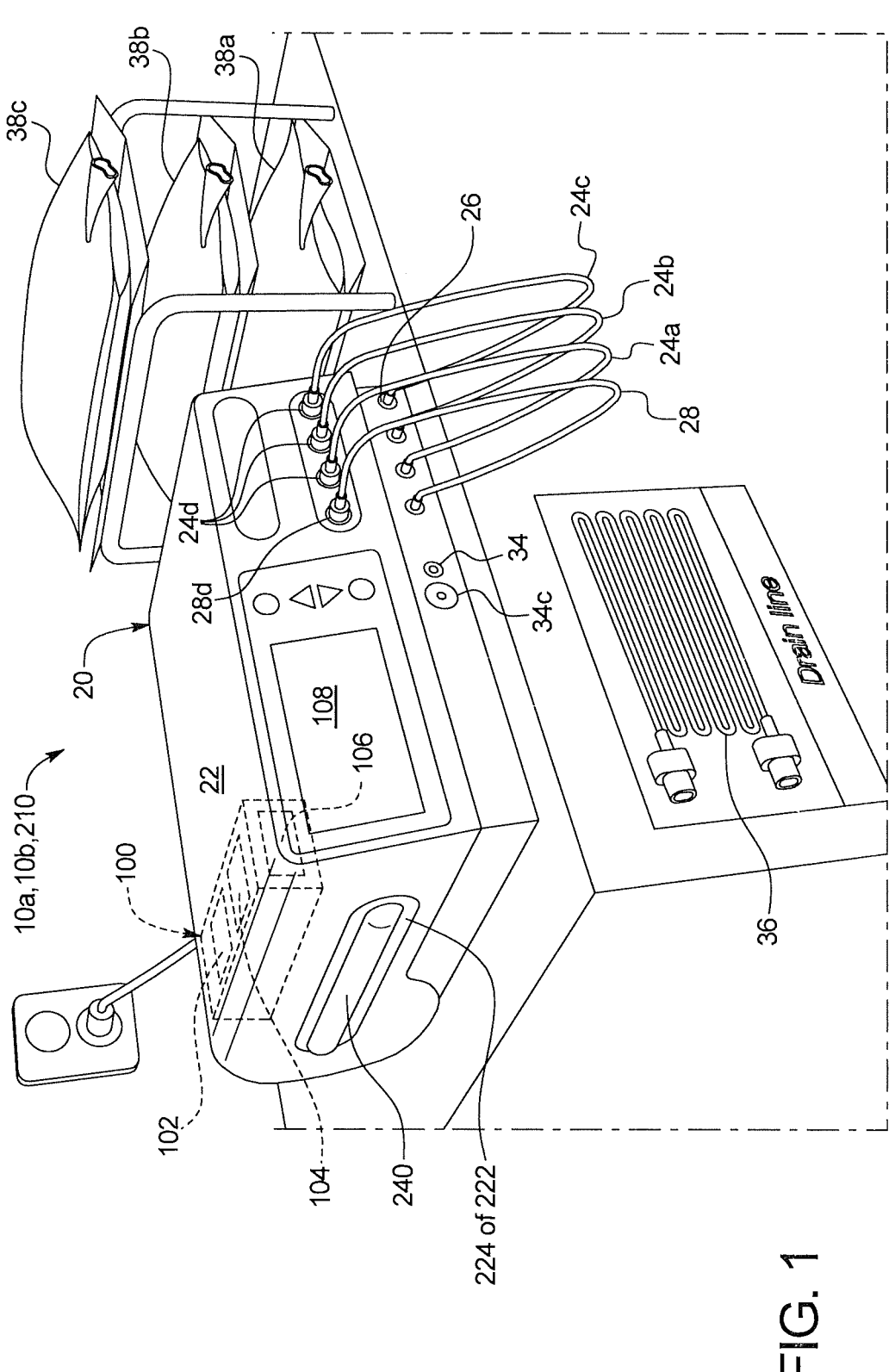
FIG. 1 is a perspective view of one embodiment of an automated peritoneal dialysis ("APD") cycler and associated system of the present disclosure.

Referring now to the drawings and in particular to FIG. 1, automated peritoneal dialysis ("APD") systems 10*a*, 10*b*, 10*c* and 210 and associated methodology of the present disclosure include an APD machine or cycler 20. Systems 10*a*, 10*b*, 10*c* and 210 and cycler 20 attempt to eliminate disposable items as much as possible and instead provide the majority of its fluid carrying portions as reusable components, which are disinfected after treatment. Fluid lines within the machine or cycler are reused. In particular, FIG.

1 illustrates that cycler 20 includes a housing 22 from which reusable PD fluid lines 24*a* to 24*c* extend from apertures 26 defined or provided by the housing. Apertures 26 may be fitted with grommets or be otherwise sealed, such that dust, fluids and other substances cannot enter housing 22 from the environment. FIG. 1 further illustrates that a reusable patient line 28 also extends from housing 22 of cycler 20 via a sealed aperture 26, e.g., fitted with a grommet. As discussed in detail below, reusable patient line 28, which is typically longer than reusable PD fluid lines 24*a* to 24*c*, may be coiled or rolled up within housing via a spool or hose reel 110 when reusable patient line 28 is not connected to a patient for treatment. Reusable patient line 28 may also be coated with a non-sticking or smooth coating to prevent dirt from collecting on the patient line over time.

When not connected to PD fluid containers or bags, the reusable PD fluid lines 24*a* to 24*c* and patient line 28 can be connected to dedicated connectors supported and provided by the housing. The reusable PD fluid and patient lines may for example extend from a front of the housing and connect to connectors also provided at the front of the housing for ready access to the PD fluid and patient lines. In the illustrated embodiment, distal ends 24*d* of reusable PD fluid lines 24*a* to 24*c* releasably attach in a fluid-tight manner to disinfection connectors 30*a* to 30*c* (see FIG. 2) provided at housing 22. Distal end 28*d* of reusable patient line 28 releasably attaches in a fluid-tight manner to patient line connector 32*a* (see FIG. 2) provided at housing 22. Disinfection connectors 30*a* to 30*c* and patient line connector 32*a* are configured to close or shut automatically when reusable PD fluid lines 24*a* to 24*c* and reusable patient line 28, respectively, are not connected to the connectors.

FIG. 1 also illustrates that housing 22 provides a drain line connector 34, which may be releasably covered by a moveable, e.g., rotatable or slideable, cover 34*c*. Drain line connector 34 receives a disposable drain line 36 for treatment, which may run to a drain container or bag or to a house drain. In an alternative embodiment, drain line 36 is reusable and is connected to a disinfection loop discussed herein.

FIG. 1 further illustrates that disposable PD fluid or solution containers or bags 38*a* to 38*c* are provided for respective connection to reusable PD fluid lines 24*a* to 24*c*. Distal ends 24*d* of reusable PD fluid lines 24*a* to 24*c* may be color coded and/or keyed to match a colored or keyed connector of a dedicated PD fluid container or bag 38*a* to 38*c*. The containers or bags may hold, e.g., different dextrose or glucose level dialysis fluids, such as 1.36% glucose dialysis fluid, 2.27% glucose dialysis fluid, 3.86% glucose dialysis fluid and/or a last bag of a different formulation of PD fluid, for example, icodextrin.

It should be appreciated that any number of reusable PD fluid lines and PD fluid containers or bags may be provided, including a single reusable PD fluid line and PD fluid container or more than one reusable PD fluid lines and PD fluid containers, such as two, three or four. In a further alternative embodiment, PD fluid containers or bags 38*a* to 38*c* are replaced by an online PD fluid generation source, which connects to and communicates fluidly with a single reusable PD fluid line. In a further alternative embodiment, any of the systems described herein are configured to operate with either prefilled PD fluid containers or bags 38*a* to 38*c* or an online PD fluid generation source. For example, the systems described herein may be provided with an additional port such that the PD machine or cycler may be docked or connected to an online PD fluid producing device. Here, the PD machine or cycler may be released or disconnected from the online PD fluid generation source if the patient wants to travel or if the online source is under repair. The patient is provided with a stock of PD fluid bags, allowing treatment to still be performed.

Besides disposable drain line 36 (and associated container if used) and disposable PD fluid containers or bags 38a to 38c, it is contemplated in one embodiment, that the only other disposable component of systems 10a to 10d is a disposable filter set 40 (see FIG. 4, system 210 also includes a disposable cleaning cartridge 240) removably connected by the patient at the distal end 28d of reusable patient line 28 to provide a final stage of PD fluid filtration prior to delivery to the patient. In an embodiment, disposable filter set 40 is spliced between the distal end 28d of reusable patient line 28 and the patient's transfer set, which leads to an indwelling PD catheter inserted into the patient.

It is contemplated for any of reusable PD fluid lines 24a to 24c, reusable patient line 28, disinfection connectors 30a to 30c, patient line connector 32a, drain line connector 34, drain line 36, PD fluid containers or bags 38a to 38c and patient line filter set 40 to be made of any one or more plastic, e.g., polyvinylchloride ("PVC") or a non-PVC material, such as polyethylene ("PE"), polyurethane ("PU"), polyetheretherketone "PEEK") or polycarbonate ("PC"). Certain of the components, such as disinfection connectors 30a to 30c, may be made of, e.g., stainless steel (of good quality) or titanium.

First Primary Embodiment

Figure 2:
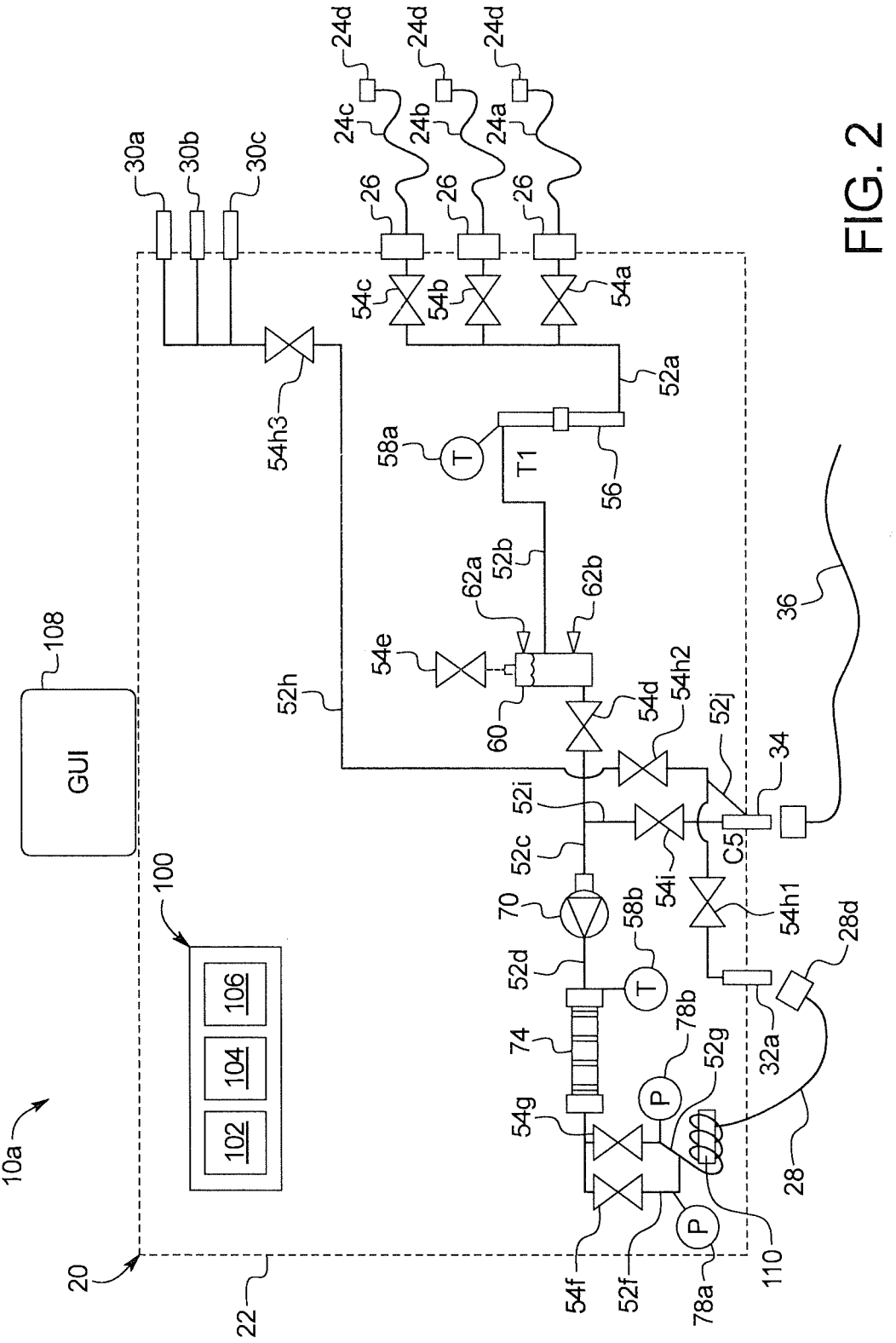
FIG. 2 is a schematic view illustrating a first primary embodiment of a flow regime for the APD cycler and associated system of the present disclosure.

Referring additionally to FIG. 2, cycler 20 of system 10a is illustrated to show one example of the inside of housing 22. FIG. 2 illustrates that reusable tubing 52a runs from each reusable PD fluid line 24a to 24c, through a PD fluid line valve 54a to 54c, respectively, to a dialysis fluid inline heater 56. In an embodiment, each of the valves of the APD cycler, including PD fluid line valve 54a to 54c, is an electrically actuated valve having a reusable valve body that occludes (e.g., when unpowered for fail safe operation) or allows (e.g., when powered) PD fluid to flow through the body. Dialysis fluid inline heater 56 is also electrically actuated in one embodiment and is, for example, a resistive heater having a reusable heater body that accepts PD fluid for treatment and disinfection heating. Inline heater 56 in an embodiment is able to heat PD fluid from room temperature or colder (e.g., if the PD fluid is stored in a cold environment) to body temperature, e.g., 37° C., at a flowrate of at least 200 milliliters (ml)/minute (lower flowrates may also be achieved, e.g., for children or infants). A temperature sensor 58a is located adjacent to heater 56, e.g., downstream from the heater to provide feedback for temperature control. If desired, a second temperature sensor (not illustrated) may be provided upstream from heater 56 to enable the incoming temperature of fresh PD fluid to be taken into account for the heating algorithm or routine, that is, to provide feedforward control, which stabilizes and speeds the responsiveness of the overall heating control. The second sensor may also provide useful information for calculating disinfection dose values, e.g., A0 values, for use during disinfection.

Reusable tubing 52b runs from the outlet of dialysis fluid inline heater 56 to an air trap 60 in the illustrated embodiment of FIG. 2. Any of the reusable tubing inside the housing of cycler 20, including reusable tubing 52a and 52b, may be made of metal, e.g., stainless steel or plastic, such as polyvinylchloride ("PVC") or a non-PVC material, such as polyethylene ("PE"), polyurethane ("PU"), polyetherether-ketone "PEEK") or polycarbonate ("PC"). In an embodiment, one or more level sensor 62a and 62b is located adjacent to air trap 60 so that a desired level or range of levels of PD fluid is maintained in the air trap. If air trap 60 needs to be filled with PD fluid as detected by level sensor 62b, control unit 100 may cause valves 54a, 54b and 54c to be closed so that pump 70 may pull a sub-atmospheric pressure in air trap 60. Pump 70 is then stopped (and possibly valve 54d is closed) to lock the pressure upstream of air trap 60. Control unit 100 then opens one of valves 54a, 54b or 54c to allow fresh fluid to be sucked into air trap 60 from one of containers 38a to 38c. Alternatively, containers 38a to 38c may be positioned above air trap 60 so that fluid can be filled gravimetrically. Another alternative option to fill air trap 60 is for control unit 100 to run pump 70 in reverse to pull PD fluid from patient line 28 (if in treatment) or drain line 36, with air trap valve 54d and vent valve 54e open and supply valves 54a, 54b and 54c closed.

Air trap 60 may be closed upstream by PD fluid line valves 54a to 54c, while valve 54d is opened to drain the air trap when needed as detected by level sensor 62a. Vent valve 54e is provided at the top of air trap 60 to allow air to be vented from the air trap during filling and to enter the air trap during draining. Although not illustrated, vent valve 54e may be provided with or operate with a vent filter, e.g., a hydrophobic filter, which prevents dialysis fluid from escaping when vent valve 54e is open and sterile filters the air entering air trap 60 to avoid contamination. Vent valve 54e may also be opened to allow air to enter the fluid lines, e.g., to mix with PD fluid for disinfection.

Reusable tubing 52c runs between air trap valve 54d and a dialysis fluid pump 70 located within housing 22 of cycler 20. Dialysis fluid pump 70 includes a reusable pump body that accepts PD fluid for pumping. That is, pump 70 does not require the PD fluid to flow within a disposable item, such as a tube or cassette. The reusable pump body of pump 70 itself accepts the PD fluid. Dialysis fluid pump 70 is of a type that is inherently volumetrically accurate so that a separate PD fluid volume measurement apparatus, such as a balance chamber or an apparatus using the ideal gas law, is not needed. Dialysis fluid pump 70 may be an electrically operated piston or membrane pump (and perhaps a gear or centrifugal pump). Apparatus and methodology for providing dialysis fluid pump 70 with a flush flow is discussed herein. Dialysis fluid pump 70 is controllable to pump to and from the patient at or within a pressure limit by controlling a level of current to the PD fluid pump. A positive patient pressure limit may for example be one to five psig (e.g., two psig (14 kPa). A negative patient pressure limit may for example be −1.0 psig to −3.0 psig (e.g., −1.3 psig (−9 kPa)). Pump 70 is also capable of supplying pressures of lower magnitude if needed, e.g., for small children or babies. Dialysis fluid pump 70 is bidirectional and continuous in one embodiment, such that a single pump may be provided. Suitable pumps for dialysis fluid pump fluid 70 include a piston pump and other inherently accurate pumps.

In the illustrated embodiment of FIG. 2, a conductivity sensor 74 is located along a reusable line or tubing 52d adjacent to dialysis fluid pump 70. Conductivity sensor 74 is used to detect the conductivity of fresh PD fluid to make sure that it is of a prescribed type, e.g., of a prescribed glucose or dextrose level. Conductivity sensor 74 may alternatively or additionally be used to detect the conductivity of the fresh PD fluid to make sure that it has been mixed correctly, e.g., if an online PD fluid source is connected instead to one of the reusable PD fluid lines 24a to 24c. Conductivity sensor 74 may alternatively or additionally be used to detect the conductivity of the used PD fluid to assess treatment effectiveness and/or to look for patient disease, such as peritonitis. A temperature sensor 58*b* is located near conductivity sensor 74, so that the conductivity reading from the sensor may be temperature compensated.

FIG. 2 further illustrates that parallel patient line valves 54*f* and 54*g* are located in an embodiment along reusable patient tubing or lines 52*f* and 52*g*, respectively, between conductivity sensor 74 and reusable patient line 28. Parallel patient line fill valve 54*f* selectively allows fresh PD fluid to flow in a fresh PD fluid lumen of the dual lumen reusable patient line 28, while parallel patient line drain valve 54*g* selectively allows used PD fluid to flow in a used PD fluid lumen of dual lumen reusable patient line 28. A first pressure sensor 78*a* is located in proximity to (e.g., downstream of) parallel patient line valve 54*f* to enable positive, fresh PD fluid fill pressures to be monitored and controlled. A second pressure sensor 78*b* is located in proximity to (e.g., upstream of) parallel patient line valve 54*g* to enable negative, used PD fluid drain pressures to be monitored and controlled. First pressure sensor 78*a* may also be used to measure used PD fluid drain pressures, e.g., for redundancy and increased accuracy. The differences in drain pressures measured by pressure sensor 78*b* versus pressure sensor 78*a* are discussed below.

As discussed above, patient line connector 32*a* extends from the APD cycler housing and accepts dual lumen reusable patient line 28 during disinfection and generally while the patient is not undergoing treatment. A disinfection tubing or line 52*h* is located inside housing 22 of APD cycler 20 and extends from patient line connector 32*a* to at least one disinfection connector, here disinfection connectors 30*a* to 30*c*. Disinfection line valves 54*h*1, 54*h*2 and 54*h*3 (valve 54*h*3 may be removed in an alternative embodiment) are located along disinfection tubing or line 52*h* to selectively open the disinfection line to run a disinfection sequence.

Figure 3:
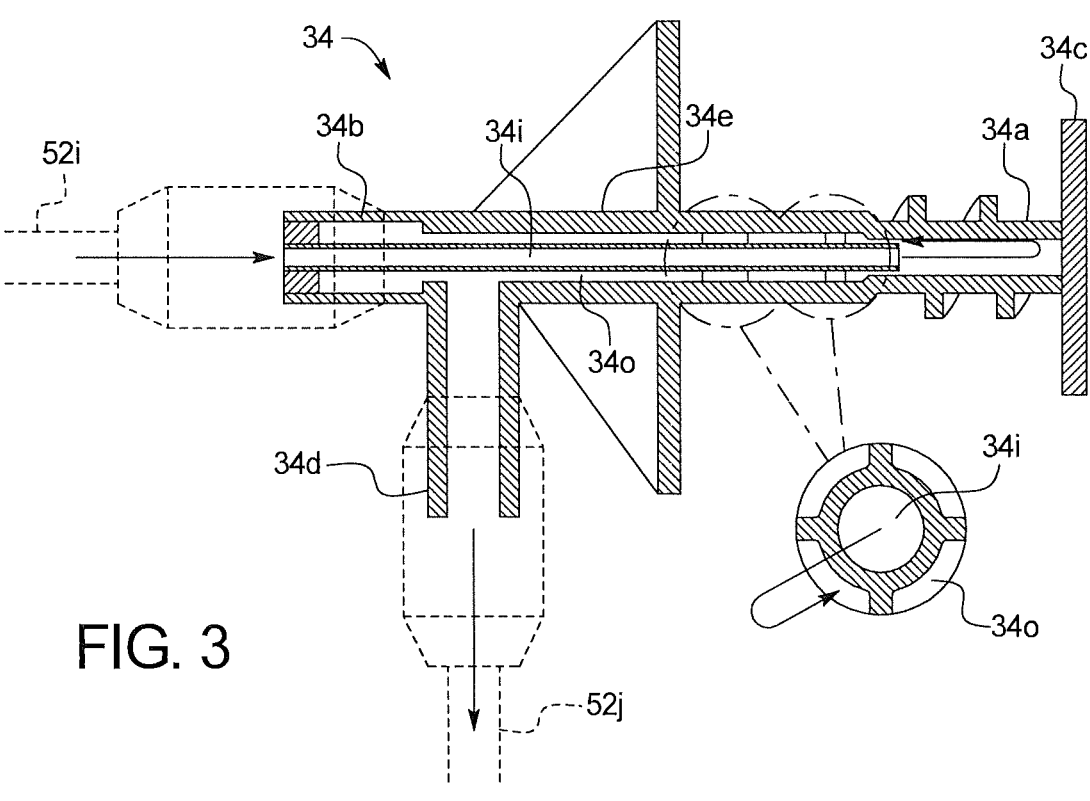
FIG. 3 shows cross-sectional and end views of one embodiment for a drain line connector of the present disclosure.

As discussed above, drain line 36 is disposable in one embodiment and connects to drain line connector 34 extending from housing 22 of APD cycler 20 during treatment. After treatment, drain line 36 is removed and discarded. Referring now to FIG. 3, drain line connector 34 is illustrated in more detail. Drain line connector 34 may be made, for example, of any of the metals or plastics discussed herein. Drain line connector 34 includes a drain line port 34*a*, e.g., a luer port, which connects releasably to drain line 36. Rotatable or slideable cover 34*c* illustrated in FIG. 1 is illustrated in FIG. 3 covering drain line port 34*a*. Rotatable or slideable cover 34*c* may be formed as part of drain line connector 34 or be separate from drain line connector 34 and mounted instead to housing 22 of APD cycler.

As illustrated in FIGS. 2 and 3, drain line connector 34 includes two internal facing ports 34*b* and 34*d*. Internal port 34*b* is placed in fluid communication with reusable tubing or line 52*i* having a drain line valve 54*i* and communicating with reusable tubing or line 52*c*. Internal port 34*d* is placed in fluid communication with reusable tubing or line 52*j*, which communicates fluidly with disinfection line valve 54*h*2 and reusable disinfection tubing or line 52*h*.

The side and sectioned end views of FIG. 3 illustrate that drain line connector 34 defines or provides a dual lumen body 34*e* that allows disinfection fluid entering port 34*b*, for example, to flow within an inner lumen 34*i* all the way to rotatable or slideable cover 34*c*, at which point the disinfection fluid is returned within an outer lumen 34*o* to port 34*d* to exit drain line connector 34. With this construction, the entire internal surface of drain line connector 34 is contacted consistently over a timed disinfection sequence and is thereby properly disinfected.

Viewing FIGS. 2 and 3, reusable PD fluid lines 24*a* to 24*c*, reusable line or tubing 52*a*, the reusable body of dialysis fluid inline heater 56, reusable line or tubing 52*b*, air trap 60, reusable line or tubing 52*c*, the reusable pump body of dialysis fluid pump 70, reusable line or tubing 52*d* including conductivity sensor 74, reusable tubing or lines 52*f* and 52*g*, reusable patient line 28, patient line connector 32*a*, capped drain line connector 34, reusable tubing or lines 52*i* and 52*j*, disinfection tubing or line 52*h* and disinfection connectors 30*a* to 30*c*, distal ends 24*d* of reusable PD fluid lines 24*a* to 24*c* and distal end 28*d* of reusable patient line 28 together form a disinfection loop 50 (see FIG. 9), which allows a disinfection fluid, e.g., heated used dialysis fluid, to contact all internal reused surfaces continuously over a timed disinfection sequence to provide proper disinfection.

Patient Line Filter Set and IPP

Figure 4:
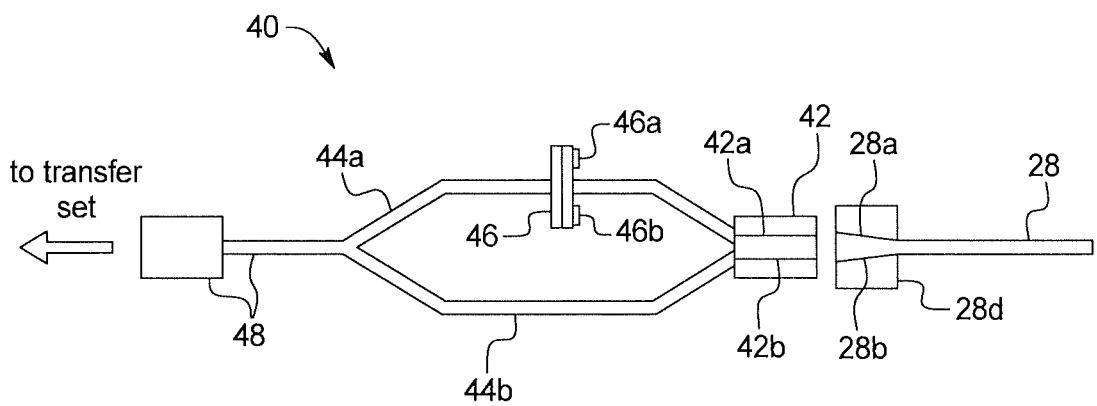
FIG. 4 is a schematic view illustrating one embodiment of a disposable filter set for connection to a reusable patient line of the present disclosure.

As discussed above, besides PD fluid containers or bags 38*a* to 38*c* and drain line 36, another disposable item of system 10*a* is a small disposable patient line filter set 40, which is connected between reusable patient line 28 and the patient's transfer set. FIG. 4 illustrates disposable patient line filter set 40 in more detail. Disposable patient line filter set 40 may be made, for example, of any of the polymer materials discussed herein. Disposable patient line filter set 40, like reusable patient line 28, is dual line lumen in one embodiment and includes a connector 42 that connects to the distal end of reusable patient line 28. Connector 42 includes a fresh PD fluid lumen 42*a* that communicates with a fresh PD fluid lumen 28*a* of the distal end of reusable patient line 28. Connector 42 also includes a used PD fluid lumen 42*b* that communicates with a used PD fluid lumen 28*b* of the distal end of reusable patient line 28. Disposable patient line filter set 40 also includes (i) a first or fresh disposable line 44*a* that communicates with the fresh PD fluid lumen 28*a* of dual lumen reusable patient line 28 and (ii) a second or effluent disposable line 44*b* that communicates with the used PD fluid lumen 28*b* of dual lumen reusable patient line 28. A final stage or sterilizing grade filter membrane 46 is located in or along first or fresh disposable line 44*a* and provides a final stage of PD fluid filtration prior to delivery to the patient. Sterilizing grade filter membrane 46 is in one embodiment itself sterilized. PD filter membrane 46 can for example be a pass-through filter that does not have a reject line. Pore sizes for sterilizing grade filter membrane 46 may, for example, 0.1 to 0.2 micron. Suitable sterile filters for filter membrane 46 may, for example, be a Pall IV-5 or GVS Speedflow filter membrane, or be a filter membrane provided by the assignee of the present disclosure.

In the illustrated embodiment, the housing of sterilizing grade filter membrane 46 may be provided with one or more hydrophobic filters or vents, e.g., vents 46*a* and 46*b*. In an embodiment, the PD fluid filtering media of sterilizing grade filter membrane 46 is hydrophilic in nature and therefore prevents air from traveling through the filter media once wetted. Sterilizing grade filter membrane 46 accordingly provides a last chance air removal mechanism just prior to the fresh PD fluid reaching the patient. Air collects in the housing of sterilizing grade filter membrane 46 upstream of the filter media, which is vented via hydrophobic filters or vents 46*a* and 46*b* located upstream of the filter medial. Hydrophobic filters or vents 46*a* and 46*b* filter and remove contaminants from any air that might enter the housing of sterilizing grade filter membrane 46 through the vents.

The configuration of disposable patient line filter set 40 allows the patient's intraperitoneal patient pressure ("IPP"), or very close to it, to be measured and used in the pumping control algorithm or routine for dialysis fluid pump 70. Viewing FIG. 4 and assuming fresh PD fluid is delivered from right to left through fresh PD fluid lumen 28*a*, fresh PD fluid lumen 42*a*, sterilizing grade filter membrane 46, fresh disposable line 44*a* and the patient's transfer set to the patient under positive pressure, the positive pressure at the junction between fresh disposable line 44*a* and used disposable line 44*b* will be the same positive pressure in used PD fluid lumen 42*b* of disposable connector 42 and all the way up used PD fluid lumen 28*b* of reusable patient line 28 and into the reusable circuitry inside the cycler (except for hydrostatic pressure due to the difference in height between the filter set 40 and the measuring pressure sensor). The reason for this is because the PD fluid in used disposable line 44*b*, used PD fluid lumen 42*b*, used PD fluid lumen 28*b* and the reusable circuitry inside the cycler (which may still be at least partially used PD fluid from the previous patient drain) is static, not moving. In cycler 20 of system 10*a*, for example, valve 54*g* is closed so that the PD fluid in the return lines has no place to flow during a patient fill. No pressure drop occurs along the static return lines, so that corresponding pressure sensor 78*b* measures the patient's positive IPP or very close to it (e.g., IPP plus a small hydrostatic component and a dynamic pressure component during flow due to the pressure drop in the line leading from the junction to the catheter tip of the patient catheter). The positive IPP measured at pressure sensor 78*b* may be used in a feedback loop by the cycler 20 control unit to set an upstream positive pressure as measured at pressure sensor 78*a*, which after the pressure drop through fresh PD fluid lumen 28*a* of reusable patient line 28, fresh PD fluid lumen 42*a* of disposable connector 42, and fresh disposable line 44*a* attempts to meet a goal or target positive IPP, wherein the positive IPP again is measured at pressure sensor 78*b*.

In system 10*b* of FIGS. 10 to 14 for positive pressure filling, valve 54*j*1 is closed and three-way valve 154*c* is oriented so that line 52*g* is closed, causing the PD fluid in used disposable line 44*b*, used PD fluid lumen 42*b*, used PD fluid lumen 28*b* and the reusable cycler line 52*g* to be static. Pressure sensor 78*b* again measures positive IPP for the pressure feedback loop of the pressure control routine for dialysis fluid pump 70 as just described.

In system 10*c* of FIGS. 15 to 21 for positive pressure filling (FIG. 19), patient valve 54*g* and disinfection valve 54*h*1 are closed, causing the PD fluid in used disposable line 44*b*, used PD fluid lumen 42*b*, used PD fluid lumen 28*b* and the reusable cycler patient line 52*g* to be static. Pressure sensors 78*b*1 and 78*b*2 (one for control, the other for safety) measure positive IPP for the pressure feedback loop of the pressure control routine for dialysis fluid pump 70 as just described.

The configuration of disposable patient line filter set 40 also allows the patient's negative IPP, or very close to it, to be measured and used in the pumping control algorithm or routine for dialysis fluid pump 70. Viewing FIG. 4 again and assuming used PD fluid is removed from left to right through the patient's transfer set, used disposable line 44*b*, used PD fluid lumen 42*b* of disposable connector 42, used PD fluid lumen 28*b* of reusable patient line 28 and into the reusable circuitry inside the cycler under negative pressure, the negative pressure at the junction between used disposable line 44*b* and fresh disposable line 44*a* will be the same negative pressure in fresh PD fluid lumen 42*a* and all the way up fresh PD fluid lumen 28*a* and into the reusable circuitry inside the cycler (except for head height differences as mentioned above). The reason for this is again because the PD fluid in fresh disposable line 44*a*, fresh PD fluid lumen 42*a*, fresh PD fluid lumen 28*a* and the reusable circuitry inside the cycler (which may still be at least partially fresh PD fluid from the previous patient fill) is static, not moving. In cycler 20 of system 10*a* for example, valve 54*f* is closed so that the PD fluid in cycler line 52*f*, fresh PD fluid lumen 28*a*, fresh PD fluid lumen 42*a* and fresh disposable line 44*a* has no place to flow during a patient drain. No pressure drop occurs along the static lines so that corresponding pressure sensor 78*a* measures the patient's negative IPP or very close to it (difference due to a small hydrostatic component and a dynamic pressure component during flow due to the pressure drop in the line leading from the junction to the catheter tip). The negative IPP measured at pressure sensor 78*a* may be used in a feedback loop by cycler 20 control unit to set an upstream negative pressure as measured at pressure sensor 78*b*, which after the pressure drop through used PD fluid lumen 28*b* of reusable patient line 28, used PD fluid lumen 42*b* of disposable connector 42, and used disposable line 44*b* attempts to meet a goal or target negative IPP, wherein the negative IPP again is measured at pressure sensor 78*b*.

In system 10*b* of FIGS. 10 to 14 for negative pressure draining, valve 54*j*1 is closed and three-way valve 154*c* is oriented so that line 52*f* is closed, causing the PD fluid in fresh disposable line 44*a*, fresh PD fluid lumen 42*a*, fresh PD fluid lumen 28*a* and the reusable cycler line 52*f* to be static (note that at least some of the PD fluid in this pathway could be fresh PD fluid from the previous patient fill). Pressure sensor 78*a* again measures negative IPP for the pressure feedback loop of the pressure control routine for dialysis fluid pump 70 as just described.

In system 10*c* of FIGS. 15 to 21 for negative pressure draining (FIG. 20), patient valve 54*f* is closed so that patient line 52*f* is closed, causing the PD fluid in fresh disposable line 44*a*, fresh PD fluid lumen 42*a*, fresh PD fluid lumen 28*a* and the reusable cycler line 52*f* to be static (note that at least some of the PD fluid in this pathway could be fresh PD fluid from the previous patient fill). Pressure sensor 78*a* (and perhaps a second safety pressure sensor) measures negative IPP for the pressure feedback loop of the pressure control routine for dialysis fluid pump 70 as just described.

Although not illustrated, it is contemplated to place a second filter in or along used disposable line 44*b*. The second filter may be a course filter that is provided for the purpose of removing fibrin, proteins, fats and other solid particles and liquid impurities from the patient's effluent prior to the effluent reaching reusable patient line 28 or other reusable lines and components within cycler 20. The second filter is discarded along with the rest of disposable patient line filter set 40 after each treatment. In an embodiment, the second, effluent filter is provided in a same housing as sterilizing grade filter membrane 46. It is contemplated to provide a fibrin trap alternatively or additionally.

Fresh and used disposable lines 44*a* and 44*b* converge at a single lumen line and connector 48, which connects to the patient's transfer set. It should be appreciated that upon draining the patient, negative pressure is applied only through used disposable line 44*b* so that used dialysis fluid does not contact sterilizing grade filter membrane 46. Likewise, all fresh PD fluid must pass through fresh disposable line 44*a* and filter membrane 46 before reaching the patient.

It should be appreciated that reusable dual lumen patient line 28 and disposable patient line filter set 40 are advantageous over a single lumen patient line because they prevent a slug of used PD fluid, present from a previous patient drain sequence, from entering the patient in a next patient fill sequence. Reusable dual lumen patient line 28 and disposable patient line filter set 40 also prevent a slug of fresh PD fluid, present from a previous patient fill sequence, from being discarded to drain in a next patient drain sequence.

FIGS. 1 and 2 illustrate that APD cycler 20 of system 10*a* of the present disclosure includes a control unit 100 having one or more processor 102 and one or more memory 104 that receive, store and process signals or outputs from the pressure sensors 78*a* and 78*b*, temperature sensors 58*a* and 58*b* and conductivity sensor 74. Control unit 100 uses pressure feedback to control dialysis fluid pump 70 to pump fresh and used PD at safe patient and system pressure limits. Control unit 100 uses temperature feedback to control inline dialysis fluid heater 56 to heat the fresh dialysis fluid to, e.g., body temperature. Control unit 100 uses temperature compensated conductivity readings to analyze fresh and/or used dialysis fluid for the reasons discussed herein.

As illustrated in detail below, control unit 100 also opens and closes dialysis fluid valves 54*a* to 54*g*, 54*h*1, 54*h*2, 54*h*3 and 54*i* in combination with the operation of dialysis fluid pump 70 and heater 56 to run a priming sequence, multiple patient fill sequences, multiple patient drain sequences, and a disinfection sequence after a PD treatment. In the disinfection sequence, each reusable PD fluid line 24*a* to 24*c* is connected to disinfection connectors 30*a* to 30*c*, respectively, reusable patient line 28 is connected to reusable patient line connector 32*a*, and drain line connector 34 is covered or capped by cover 34*c*. The disinfection sequence readies APD cycler 20 for the next treatment. In an embodiment, used dialysis fluid or effluent is heated after the final drain and is used as the disinfection fluid for disinfection.

Control unit 100 also includes a video controller 106 that interfaces with a user interface 108, which may include a display screen operating with a touchscreen and/or one or more electromechanical button, such as a membrane switch. User interface 108 may also include one or more speaker for outputting alarms, alerts and/or voice guidance commands. User interface 108 may be provided with cycler 20 as illustrated in FIG. 1 and/or be a remote user interface operating with control unit 100. Control unit 100 may also include a transceiver (not illustrated) and a wired or wireless connection to a network, e.g., the internet, for sending treatment data to and receiving prescription instructions from a doctor's or clinician's server interfacing with a doctor's or clinician's computer.

In FIGS. 5 to 21, darkened valves are open at least at some point within the sequence. The arrows show one embodiment for the direction of fresh or used dialysis fluid flow.

Figure 5:
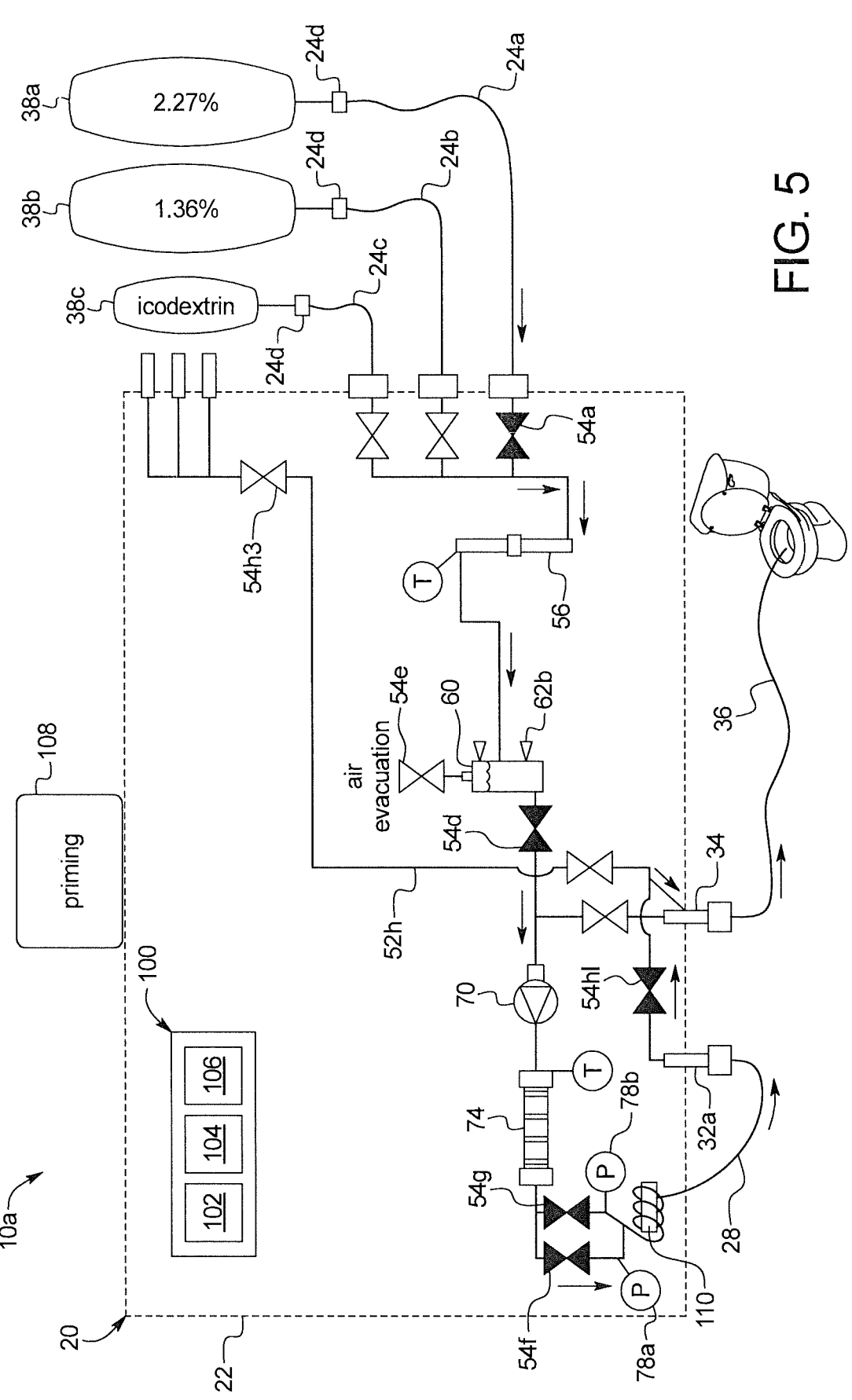
FIG. 5 is a schematic view illustrating a priming sequence for the first primary embodiment of the APD cycler and associated system of the present disclosure.

FIG. 5 illustrates one possible prime or priming sequence under control of control unit 100 controlling cycler 20 of system 10*a*. For the priming sequence, the patient or caregiver connects PD fluid or solution containers or bags 38*a* to 38*c* to reusable PD fluid lines 24*a* to 24*c*, respectively, according to the patient's prescription specifying PD fluid type and volume. PD fluid lines 24*a* to 24*c* may be dedicated to certain solution containers or bags 38*a* to 38*c* and different bags may contain different glucose or dextrose levels and/or formulations as discussed herein. The patient or caregiver also connects drain line 36 to drain line connector 34 and runs the distal end of the drain line to a drain, e.g. toilet, bathtub or drain container.

The patient or caregiver then presses "start prime" on user interface 108, e.g., via a touch screen. Control unit 100 causes the valve associated with a desired priming fluid container or bag 38*a* to 38*c*, e.g., valve 54*a* for container 38*a*, to open. Control unit 100 also causes air trap valve 54*d*, fresh fluid patient line valve 54*f* and disinfection line valve

54*h*1 to open. Opened disinfection line valve 54*h*1 allows priming fluid to flow through drain connector line 52*j* and drain line connector 34 to prime drain line 36.

Control unit 100 then actuates dialysis fluid pump 70 in the filling direction to pump fresh PD fluid through the opened priming lines. If low level sensor 62*b* senses a low level of fresh PD fluid, control unit 100 stops dialysis fluid pump 70. Control unit 100 closes valves 54*a* to 54*c*, opens vent valve 54*e* and reverses dialysis fluid pump 70 until upper level sensor 62*a* detects the PD fluid. Reversing dialysis fluid pump 70 to fill air trap 60 may be performed in steps or stages to prevent (or reduce the amount of) used dialysis fluid or air from drain line 36 entering cycler 20. In an embodiment, priming is completed when control unit, knowing the output of pump 70, calculates or accumulates that the fresh PD fluid volume needed to fill the lines to drain line connector 34 is achieved (plus an extra volume down drain line 36 to ensure proper and full priming, see also discussion of rinse below).

When the initial fluid container or bag 38*a* to 38*c*, e.g., container 38*a*, is consumed and the next fluid container or bag is to be used, e.g., container 38*b* or 38*c*, control unit 100 opens the associated valve 54*b* or 54*c* and actuates dialysis fluid pump 70 in the filling direction. Air in associated reusable PD fluid lines 24*b* or 24*c* is removed via air trap 60. If a low fluid level is detected by low level sensor 62*b*, control unit 100 may again open vent valve 54*e* and reverse dialysis fluid pump 70 until upper level sensor 62*a* detects the PD fluid.

In an embodiment, dialysis fluid heater 56 is not actuated during priming, however, the output of pressure sensor 78*a* may be monitored to pump fresh PD priming fluid at a maximum safe pressure for system 10*a* because the patient is not involved with the fluid flow. Additionally, control unit 100 may monitor the output of conductivity sensor 74 during priming to (i) ensure that solution type from container or bag 38*a* is correct according to the patient's prescription and/or (ii) detect when PD fluid has reached the conductivity sensor, replacing the air.

In various embodiments, priming as discussed in connection with FIG. 5 occurs after a rinse of the disinfection fluid from a prior disinfection sequence. The prior disinfection sequence may end with a complete drain of the disinfection fluid and a subsequent rinse of the inner walls of the tubing and components of cycler 20 contacted by the disinfection fluid. The prior disinfection sequence may instead end with a complete drain of the disinfection fluid only but no subsequent rinse. The prior disinfection sequence may further instead end with no drain of the disinfection fluid or subsequent rinse. The priming sequence of FIG. 5 picks up where the prior disinfection sequence left off. If the prior disinfection sequence ended with a drain and a rinse, then the priming sequence begins with a prime as discussed in connection with FIG. 5. If the prior disinfection sequence ended with a drain only and no rinse, then the priming sequence begins with a rinse of the inner walls of the tubing and components of cycler 20 contacted by the disinfection fluid, e.g., using heated, fresh dialysis fluid, prior to a final prime. If the prior disinfection sequence ended with no drain or rinse, then the priming sequence begins with a drain of the previously used disinfection fluid and then a rinse of the inner walls of the tubing and components of cycler 20 contacted by the disinfection fluid, e.g., using heated, fresh dialysis fluid, prior to a final prime.

Figure 6:
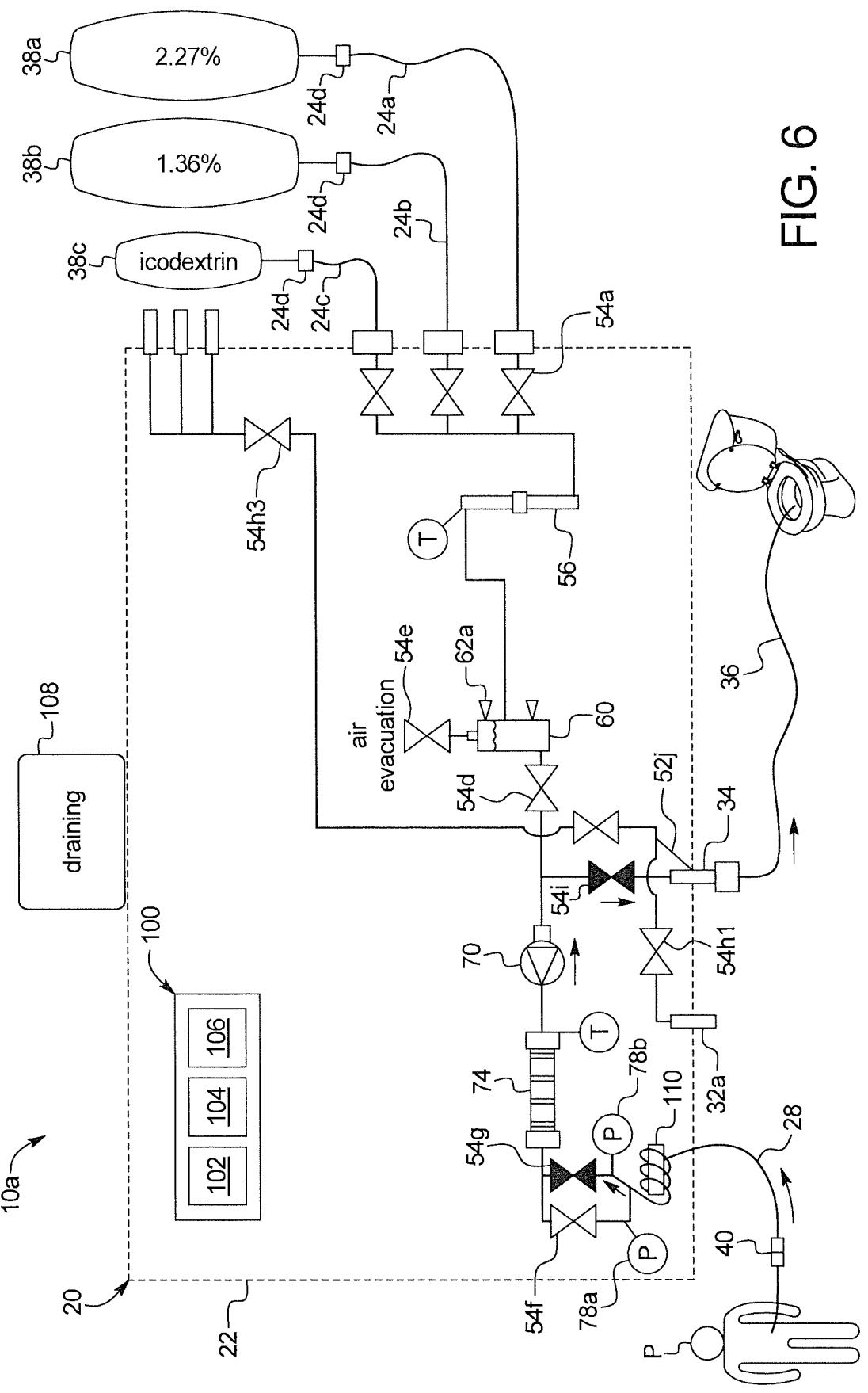
FIG. 6 is a schematic view illustrating a patient drain sequence for the first primary embodiment of the APD cycler and associated system of the present disclosure.

FIG. 6 illustrates one possible patient drain sequence under control of control unit 100 controlling cycler 20 of system 10*a*. In many instances, the patient is full of used PD fluid from a previous treatment when the patient begins a new treatment. Thus after priming, the next step is often an initial patient drain sequence. User interface 108 may prompt patient P to enter whether a drain is needed or system 10_a_ may automatically start with a drain to see if one is needed and quickly exit the drain if, e.g., one or more pressure sensor 78_a_ and 78_b_ indicates that there is no effluent to be drained. It should be appreciated however that the following description applies to all patient drain sequences. For a drain sequence occurring directly after priming, the patient or caregiver removes reusable patient line 28 from patient line connector 32_a_ provided at housing 22 of cycler 20 and connects distal end 28_d_ of reusable patient line 28 to disposable patient line filter set 40 (see FIG. 4) and then connects disposable filter set 40 to the patient's transfer set. As discussed below, reusable patient line 28 may be uncoiled from a spool or hose reel 110 to extend to patient P. Patient P or caregiver could alternatively connect disposable filter set 40 to the patient's transfer set before connecting the disposable filter to reusable patient line 28. It should be appreciated that the connections just described are the same for a patient fill occurring directly after priming. Rinsing in any of the above variations may be performed using one or more cycle of filling and flushing the rinsing fluid to drain.

The patient or caregiver then presses "start treatment" or "start drain" on user interface 108, e.g., via a touch screen. Control unit 100 causes treatment to begin, e.g., with an initial drain. Control unit 100 causes or allows patient line fill valve 54_f_, disinfection line valves 54_h_1 to 54_h_3, air trap valve 54_d_ and PD fluid line valves 54_a_ to 54_c_ to be closed. Control unit 100 causes patient line drain valve 54_g_ and drain line valve 54_i_ to be opened and dialysis fluid pump 70 to be run in a reversed drain direction to pull used PD fluid from patient P, through the patient's transfer set, through used disposable line 44_b_ of disposable filter set 40, through used PD fluid lumen 28_b_ of reusable patient line 28, and though patient line drain valve 54_g_, and to then push the used PD fluid through drain line valve 54_i_, through drain line connector 34, and through disposable drain line 36 to a house drain or drain container.

In an embodiment, dialysis fluid heater 56 is not actuated during a patient drain, however, the output of at least one of pressure sensor 78_a_ or pressure sensor 78_b_ is monitored to ensure that effluent or used PD fluid is removed from patient P at or within safe drain pressure limit, for example, −1.0 psig to −3 psig (e.g., −1.3 psig (−9 kPa)). The output of pressure sensor 78_b_ may also be monitored to detect the end of the patient drain, e.g., for control unit 100 to look for a characteristic increase in negative pressure signaling that the patient is or is almost empty, ending the patient drain. Alternatively, the patient drain may end when a prescribed amount of effluent or used PD fluid, including the patient's ultrafiltration, has been removed from the patient. Control unit 100 may additionally monitor the output of conductivity sensor 74 during the patient drain to evaluate treatment effectiveness and/or look for patient disease. Such information may be stored in one or more memory 104 and/or sent from cycler 20 via a wired or wireless connection to a network, e.g., the internet, for storage and analysis in a doctor's or clinician's database.

Filter set 40 presents an issue for priming because the set is initially full of air. The drain sequence just described removes air from disposable line 44_b_ of disposable filter set 40 but not fresh disposable line 44_a_ of the disposable filter. That air would then be delivered to the patient upon a subsequent fill. It is accordingly contemplated to configure control unit 100 to run a sequence before the patient fill to pump a small amount of fresh dialysis fluid (the volume of fresh disposable line 44_a_ is known) to push the air from fresh disposable line 44_a_ into the patient's transfer set but not into the patient, and then pull that volume back towards cycler 20 so that the air is pulled into disposable line 44_b_. The push and pull sequence may be performed multiple times so that the slug of air is pulled further up into used PD fluid lumen 28_b_ of dual lumen reusable patient line 28.

Figure 7:
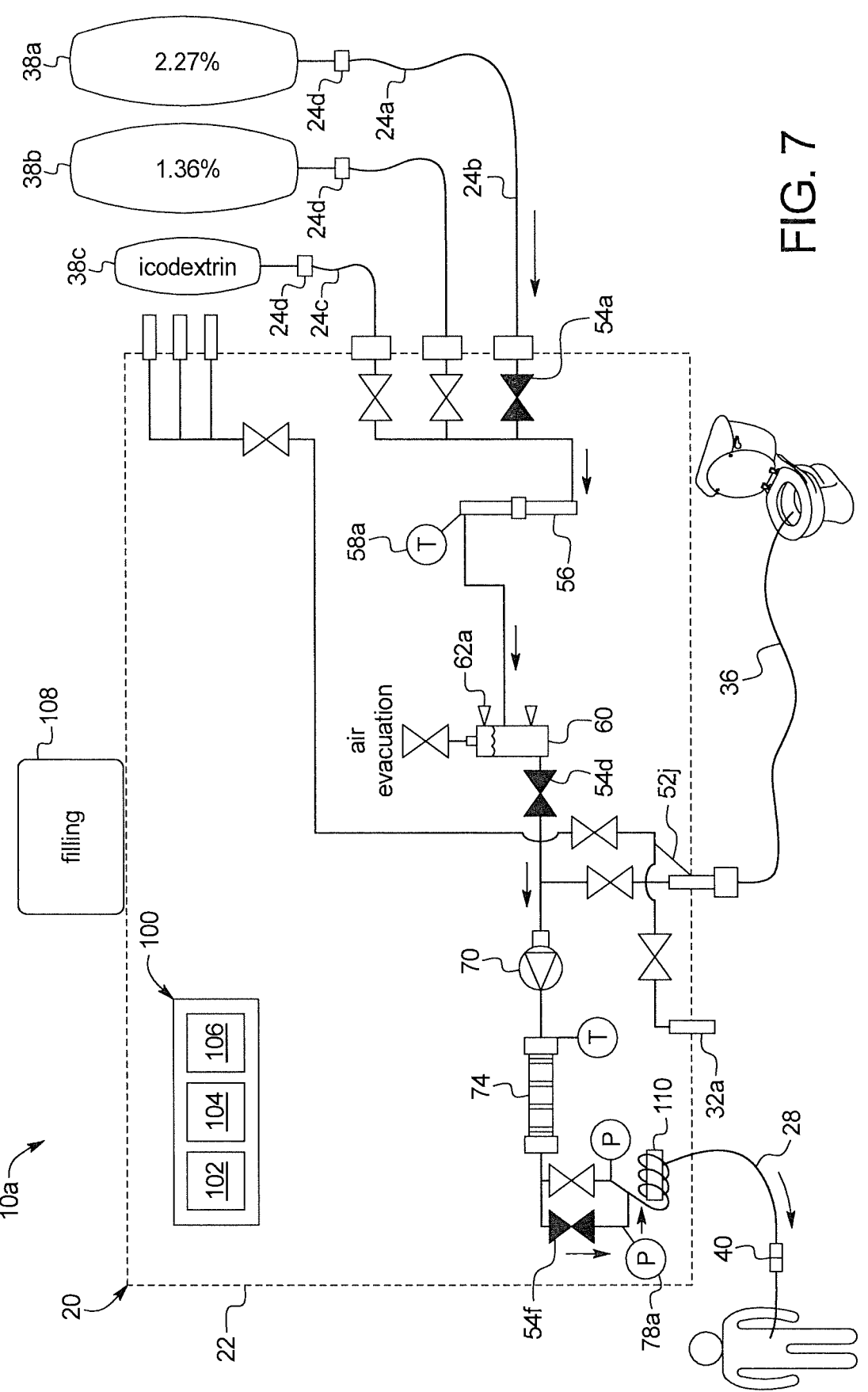
FIG. 7 is a schematic view illustrating a fill sequence for the first primary embodiment of the APD cycler and associated system of the present disclosure.

FIG. 7 illustrates one possible patient fill sequence under control of control unit 100 controlling cycler 20 of system 10_a_. If the patient fill occurs directly after priming, then the patient or caregiver makes the connections discussed above with FIG. 6 and then presses "start fill" on user interface 108, e.g., via a touch screen. If, as here, the patient fill follows an initial patient drain, control unit 100 switches automatically to the patient fill (which may include the push and pull of fresh dialysis fluid to clear fresh disposable line 44_a_ of disposable filter 40 of air discussed above) when the patient drain is finished without requiring an input from patient P or the caregiver. Here, control unit 100 causes or allows some or all of patient line drain valve 54_g_, drain line valve 54_i_ disinfection line valves 54_h_1 to 54_h_3, and the non-used PD fluid line valves 54_b_ and 54_c_ to be closed. Control unit 100 causes the needed PD fluid line valve 54_a_, air trap valve 54_d_ and patient line fill valve 54_f_ to be opened and dialysis fluid pump 70 to be run in a forward fill direction to pull fresh PD fluid from PD fluid container or bag 38_a_ and into air trap 60 and then push fresh PD fluid through conductivity sensor 74, through patient line fill valve 54_f_, through reusable patient line 28, through fresh disposable line 44_a_ and sterilizing grade filter membrane 46 of disposable filter set 40, and through the patient's transfer set to patient P. In an embodiment, control unit 100 monitors the output of inherently accurate dialysis fluid pump 70 to meter a precise amount of fresh PD fluid to the patient. Level sensors 62_a_ and 62_b_ are monitored, and control unit 100 takes into account any fluid that is removed from the fill if pump 70 has to be run in reverse to fill air trap 60 to upper level sensor 62_a_. The patient fill is complete when a prescribed amount of fresh PD fluid is delivered to patient P.

In the illustrated embodiment, inline dialysis fluid heater 56 is actuated during a patient fill, wherein the output from temperature sensor 58_a_ is used as feedback to control the temperature of fresh PD fluid to be body temperature or 37° C. Control unit 100 also monitors the output of at least one of pressure sensor 78_a_ or pressure sensor 78_b_ to ensure that fresh PD fluid is pumped to patient P at or within a safe fill pressure limit, for example, one to five psig (e.g., two psig (14 kPa)). Control unit 100 may also continue to monitor conductivity sensor 74 to ensure that the prescribed type or formulation of fresh PD fluid is being used.

The drain and fill sequences discussed above are repeated as prescribed, e.g., until the contents of each PD fluid container or bag 38_a_ to 38_c_ are delivered to the patient. In each fill, a different PD fluid line valve 54_a_ to 54_c_ may be opened, or a single valve 54_a_ to 54_c_ may be opened for multiple fills depending on the size of PD fluid containers or bags 38_a_ to 38_c_. One or more patient fill(s) of a treatment may pull different glucose level PD fluids from different containers or bags 38_a_ to 38_c_ to form a blended glucose level PD fluid for delivery to the patient. For example, a patient fill may pull from a 1.36% glucose container and a 2.27% glucose container to form a glucose level PD fluid anywhere in between 1.36% and 2.27%. Valves 54_a_ to 54_c_ may be toggled to create virtually any glucose concentration in between the glucose levels provided in PD fluid containers or bags 38a to 38c. The final PD fluid container or bag 38c may contain, for example, icodextrin, which is intended to be left within patient P after disconnecting from cycler 20, e.g., by disconnecting reusable patient line 28 from disposable filter set 40 (and allowing reusable patient line 28 to be coiled or spooled onto spool or hose reel 110), disconnecting disposable filter set 40 from the patient's transfer set and reconnecting reusable patient line 28 to patient line connector 32a. In an alternative treatment, system 10a allows treatment to end after a final patient drain.

Figure 8:
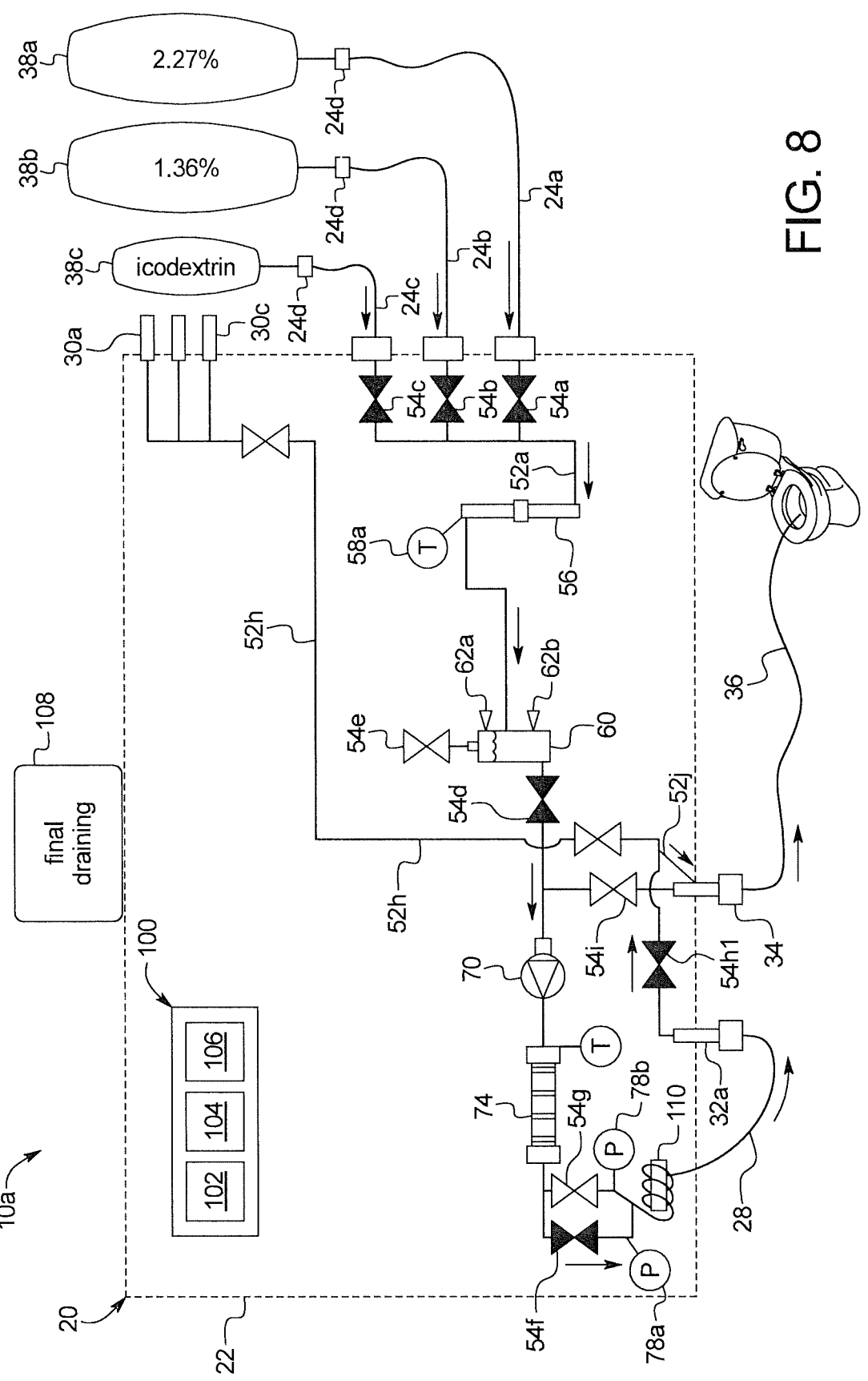
FIG. 8 is a schematic view illustrating a final drain sequence for the first primary embodiment of the APD cycler and associated system of the present disclosure.

FIG. 8 illustrates one possible final drain sequence under control of control unit 100 controlling cycler 20 of system 10a, which occurs, for example, after the final patient fill sequence and after the patient disconnects from reusable patient line 28 and plugs it back into patient line connector 32a. As soon as control unit 100 detects that reusable patient line 28 and is plugged into patient line connector 32a (e.g., (i) pump 70 pulls slight vacuum with valve 54h1 closed and one or more patient valve 54f or 54g open, while control unit monitors pressure sensor 78a and/or 78b, (ii) via a separate proximity sensor or contact closure) and/or (iii) pump 70 pumps a small volume of fluid back and forth across one or more of pressure sensors 78a and 78b creating small pressure oscillations, when patient line 28 is connected to connectors to 32a, there will be a sudden (or step wise) increase of the amplitude of the sensed pressure oscillations), control unit 100 begins the final drain sequence. Here, patient line fill valve 54f and disinfection line valve 54h1 are opened and any PD fluid container or bag 38a to 38c that is not completely empty is emptied. That is, control unit 100 knows how much fresh PD fluid has been removed from each container or bag 38a to 38c and therefore knows which containers need to be emptied. In an embodiment PD fluid line valves 54a, 54b and 54c are each opened (or opened sequentially as needed) and dialysis fluid pump 70 pulls the remaining PD fluid into air trap 60 and pushes the fluid through reconnected reusable patient line 28, through a portion of disinfection tubing or line 52h, through drain connector line 52j, drain line connector 34 and drain line 36 to drain.

In an embodiment, control unit 100 keeps track of the additional amount of fresh PD fluid removed from containers or bags 38a to 38c and stops dialysis fluid pump 70 when the accumulated amount meets or comes within a certain percentage of the supplied amount of PD fluid for the container. Alternatively or additionally, a flow switch (not illustrated) outputting to control unit 100 may be provided, e.g., along tubing or line 52a to also ensure flow is present when heater 56 is energized, to detect when any or all (depending on the state of valves 54a to 54c) of containers or bags 38a to 38c is/are empty or practically empty.

In an embodiment, when the last connected container or bag 38a to 38c bag is emptied, control unit 100 of system 10a runs pump 70 to pump a calculated volume to empty as much fluid as possible from air trap 60 to drain. To do so, air trap valve 54d, patient line fill valve 54f and vent valve 54e are opened, while all PD fluid line valves 54a to 54c are closed. Fluid remaining in air trap 60 may be used during disinfection to fill disinfection tubing or line 52h. Here, containers or bags 38a to 38c are emptied at the end of treatment so that the patient has less weight to carry, but cycler 20 is left full of fresh dialysis fluid for disinfection.

Figure 9:
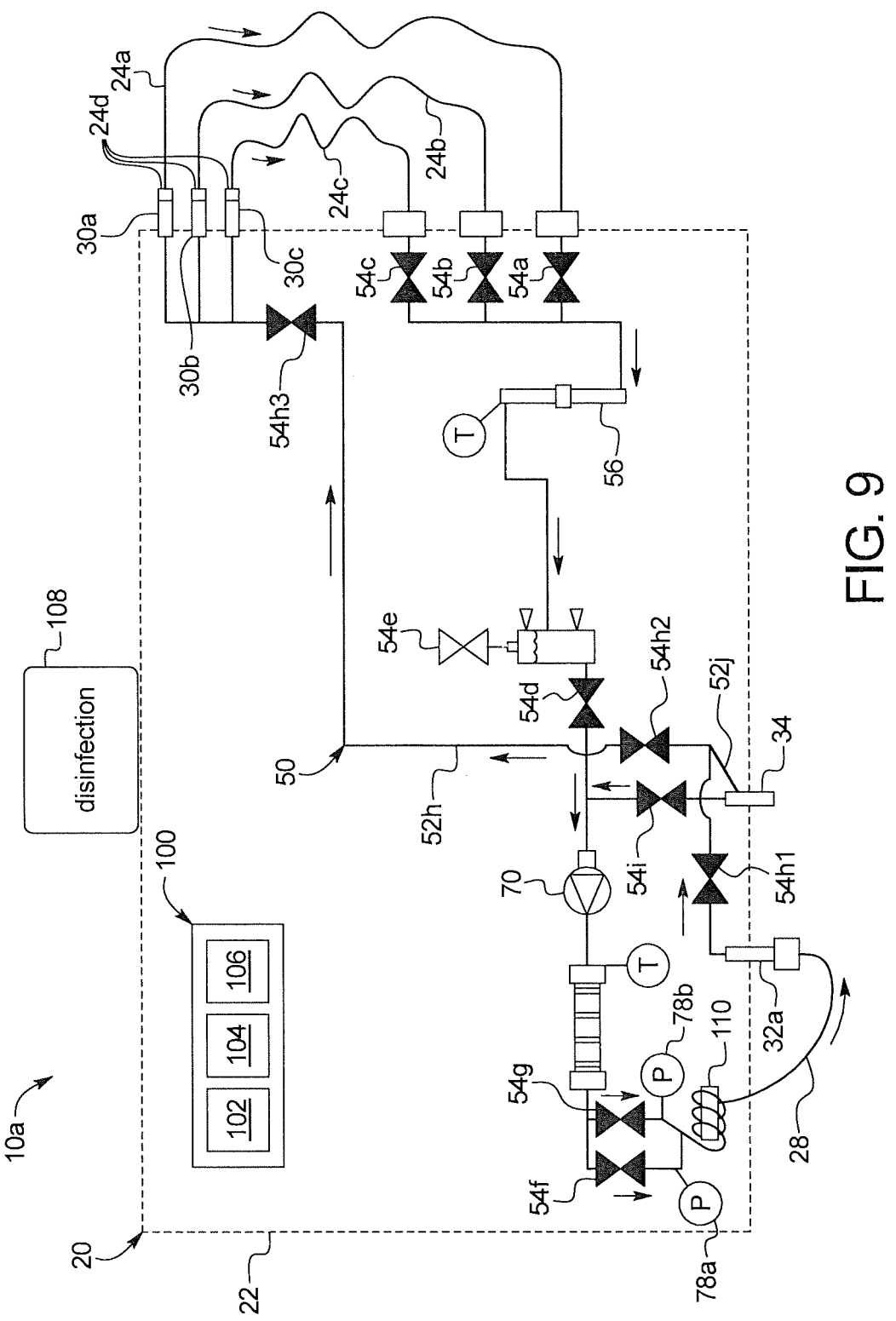
FIG. 9 is a schematic view illustrating a disinfection sequence for the first primary embodiment of the APD cycler and associated system of the present disclosure.

As illustrated in FIG. 9, at the end of treatment, control unit 100 automatically runs a disinfection sequence using disinfection circuit 50 described above in which reusable patient line 28 is connected to patient line connector 32a, drain line connector 34 is covered or capped by rotatable or slideable cover 34c, and PD fluid lines 24a to 24c are plugged into disinfection connectors 30a to 30c. Control unit 100 opens all fluid valves 54a to 54d and 54f to 54h3 and closes vent valve 54e. Control unit 100 runs dialysis fluid pump 70 and actuates heater 56 to pump heated (e.g., to 70° C. or greater) unused fresh PD fluid, used PD fluid or a combination of fresh and used PD fluid continuously throughout disinfection circuit 50, e.g., for a set amount of time such as 120 minutes. The disinfection fluid as discussed below may alternatively or additionally be water or a dedicated disinfection fluid, e.g., using citric acid. One or both pressure sensors 78a and/or 78b may be used at the beginning of the disinfection sequence for control unit 100 to see if a disinfection pressure is reached and if not to determine that one of the disinfection connections has not been made or made correctly, and to thereby halt the disinfection and post an audio, visual or audiovisual alarm at user interface 108. It is contemplated for control unit 100 to reverse dialysis fluid pump 70 one or more time(s) during the disinfection sequence (arrows would run in reverse to those shown) and/or allow a certain amount of air to fill a portion disinfection circuit 50 during the disinfection sequence (e.g., via vent valve 54e) to increase turbulence and impact force on the insides of the lines or tubing forming disinfection circuit 50. Dialysis fluid pump 70 may also be run at a maximum safe pressure and flowrate for system 10a to likewise achieve better disinfection. Disinfection may occur, for example, for 120 minutes.

It should be appreciated that while FIG. 9 illustrates all valves being open during disinfection (except vent valve 54e), certain valves may instead be closed or toggled open and closed during disinfection. For example, one or more of dialysis fluid source valves 54a to 54c, drain line valve 54i and/or disinfection line valve 54h2 may be closed or toggled open and closed during disinfection. And as discussed above, the disinfection sequence described in connection with FIG. 9 may end with a drain and rinse, a drain only or no drain or rinse (disinfection fluid left within cycler 20 until the next treatment). In an embodiment, the drain and possibly the rinse are performed by connecting the next treatment's drain line 36 to drain line connector 34 after disinfection, allowing the disinfection fluid and possibly the rinse fluid to be pumped to house drain or a drain container. The drain line 36 may then be clamped at the end if needed (e.g., when using house drain) to wait for the next treatment. The rinse fluid may be a specialized rinse fluid or fluid from one of the next treatment's PD fluid containers 38a to 38c connected to one of reusable PD fluid lines 24a to 24c. In one preferred embodiment, however, the disinfection fluid is left to reside inside cycler 20 until the next treatment, wherein no ports are opened and no bacteria can enter system 10a.

It is contemplated for system 10a, and any of the other systems described herein using a dual lumen patient line, for control unit 100 to monitor pressure sensors 78a and 78b to look for a kink in patient line 28 and possibly for scale buildup in the double lumen tubes. Dual lumens 28a and 28b may be equal in diameter, such that the pressure drop should be similar in both lumens. Thus in FIG. 9, for example, by alternating valves 54f and 54g and maintaining a constant flowrate of disinfection fluid, control unit 100 may calculate the individual pressure drop of each lumen as the difference between the outputs of pressure sensors 78a and 78b. If one lumen 28a or 28b has a higher pressure drop than the other during disinfection, more disinfection cycle time may be focused on that lumen, or the cycle time in the lumens may be adjusted to compensate for the different pressure deltas.

Control unit 100 in FIG. 9 may also make pressure check comparisons against like pressure checks made in earlier disinfection sequences (e.g., form a plot over time viewable by service personal) to gage an overall status of the reusable circuitry of cycler 20 and reusable patient line 28, e.g., for scaling or other internal build-up. Control unit 100 may be configured to automatically determine the need for and send a communication to a network service portal to signal that circuitry maintenance is likely required. Dual lumen patient tube 28 is a good candidate for such pressure checking and analysis because it may be relatively long, e.g., seven meters, thus providing a good signal to noise ratio compared to a short tube (or component) in which a scaling problem may be hard to differentiate compared to normal pressure variations.

Second Primary Embodiment

Referring now to FIGS. 10 to 14, an alternative APD system employing disinfection is illustrated by system 10b. System 10b includes many of the same components as system 10a, which are generally numbered the same and include all structure, functionality and alternatives discussed above for system 10a. For example, system 10b includes cycler 20 and control unit 100 having one or more processor 102, one or more memory 104 and a video controller 106. System 10b includes PD fluid containers or bags 38a to 38c, which connect to distal ends 24d of reusable PD fluid lines 24a to 24c, respectively. Reusable PD fluid lines 24a to 24c extend from apertures 26 defined or provided by housing 22 of cycler 20 (see FIG. 1). System 10b includes inline dialysis fluid heater 56, reusable line or tubing 52b, air trap 60 operating with upper and lower level sensors 62a and 62b, air trap valve 54d, vent valve 54e, reusable line or tubing 52c, dialysis fluid pump 70, conductivity sensor 74, temperature sensors 58a and 58b, reusable line or tubing 52d, pressure sensors 78a and 78b, reusable patient tubing or lines 52f and 52g, hose reel 110, dual lumen reusable patient line 28, reusable tubing or line 52i having a drain line valve 54i and communicating with reusable tubing or line 52c, reusable tubing or line 52j and drain line connector 34. FIGS. 10 to 14 also illustrate that system 10b includes and uses disposable filter set 40, which communicates fluidly with fresh PD fluid lumen 28a and used PD fluid lumen 28b of dual lumen reusable patient line 28. Each of pump 70, heater 56, valves and sensors is controlled by and/or outputs to control unit 100.

System 10b differs in one respect by replacing certain two-way valves of system 10a with three-way valves under control of control unit 100. In the illustrated embodiment, a first three-way valve 154a communicates with (i) PD fluid container or bag 38a via reusable PD fluid line 24a having distal end 24d, (ii) reusable tubing or line 52a1 and (iii) disinfection tubing or line 52h1. Second three-way valve 154b communicates with (i) reusable tubing or line 52a1, (ii) reusable tubing or line 52a2 and (iii) disinfection tubing or line 52h2. Third three-way valve 154c communicates with (i) reusable line or tubing 52d, (ii) fresh reusable patient tubing or line 52f and (iii) used reusable patient tubing or line 52g and (iv) drain tubing or line 52j.

Disinfection tubing or line 52h1 as illustrated is in fluid communication with drain tubing or line 52j between drain valves 54j1 and 54j2, which are under control of control unit 100. Second disinfection line or tube 52h2 extends between second three-way valve 154b and disinfection connector 30a. A third disinfection line or tube 52l extends between disinfection connectors 30b and 30c and operates with disinfection valve 54l, which is under control of control unit 100.

System 10b also includes an alternative patient line connector 32b. Unlike patient line connector 32a, patient line connector 32b does not close a loop to the internal fluid circuitry of cycler 20. Patient line connector 32b instead includes an internal lumen, e.g., a U-shaped lumen, which directs fresh or used dialysis fluid from one PD fluid lumen 28a or 28b of dual lumen reusable patient line 28 into the other PD fluid lumen 28b or 28a.

Figure 10:
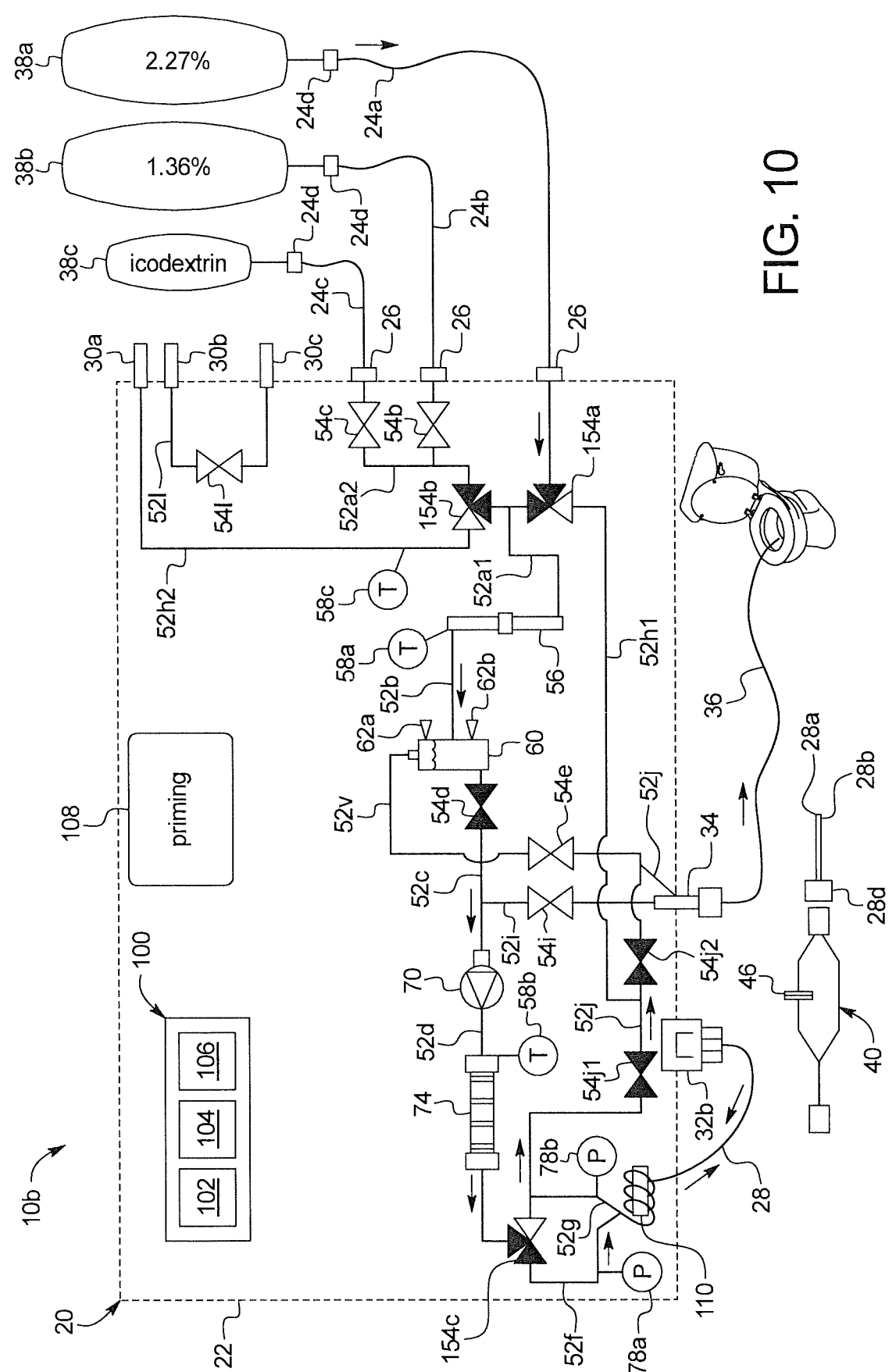
FIG. 10 is a schematic view illustrating a priming sequence for a second primary embodiment of the APD cycler and associated system of the present disclosure.

FIG. 10 also illustrates one possible priming sequence for system 10b under control of control unit 100. For the priming sequence (which may begin after a drain and rinse or after a rinse as discussed with system 10a), the patient or caregiver as with system 10a connects PD fluid or solution containers or bags 38a to 38c to reusable PD fluid lines 24a to 24c, respectively, according to the patient's prescription specifying PD fluid type and volume. The patient or caregiver also connects drain line 36 to drain line connector 34 and runs the distal end of the drain line to a drain, e.g. toilet, bathtub or drain container. The patient or caregiver then presses "start prime" on user interface 108, e.g., via a touch screen. As before, in FIGS. 10 to 14 darkened valves are open at least at some point within the sequence, while the arrows show one embodiment for the direction of fresh or used dialysis fluid flow.

Control unit 100 in FIG. 10 also causes first three-way valve 154a to be set or oriented such that fresh dialysis fluid from PD fluid container or bag 38a can flow through reusable tubing or line 52a1. Second three-way valve 154b is set or oriented so that disinfection line 52h2 is closed. Dialysis fluid container line valves 54b and 54c are also closed, such that fresh dialysis fluid from PD fluid container 38a is forced into reusable tubing or line 52a1. Control unit 100 also causes air trap valve 54d and drain valves 54j1 and 54j2 to be open and third three-way valve 154c to be set or oriented so that fresh dialysis priming fluid, pumped via pump 70, flows into patient tubing or line 52f, through PD fluid lumen 28a, through the recirculation lumen of patient line connector 32b, through the other PD fluid lumen 28b, through patient tubing or line 52g, through drain tubing or line 52j, through drain line connector 34 and disposable drain line 36 to house drain or a drain container. Heater 56 does not need to be actuated or energized. Level sensors 62a and 62b output to control unit 100, which controls pump 70 and three-way valves 154a to 154c to either fill or empty air trap 60 as needed. In another phase of priming, valve 54j2 is closed and valve 54e is opened, three-way valves 154a and 154c flip their orientation and pump 70 runs in a reverse direction to fill air trap 60. Outputs from at least one of pressure sensors 78a and 78b is/are used to ensure that priming fluid pressure is within a safe system limit.

Figure 11:
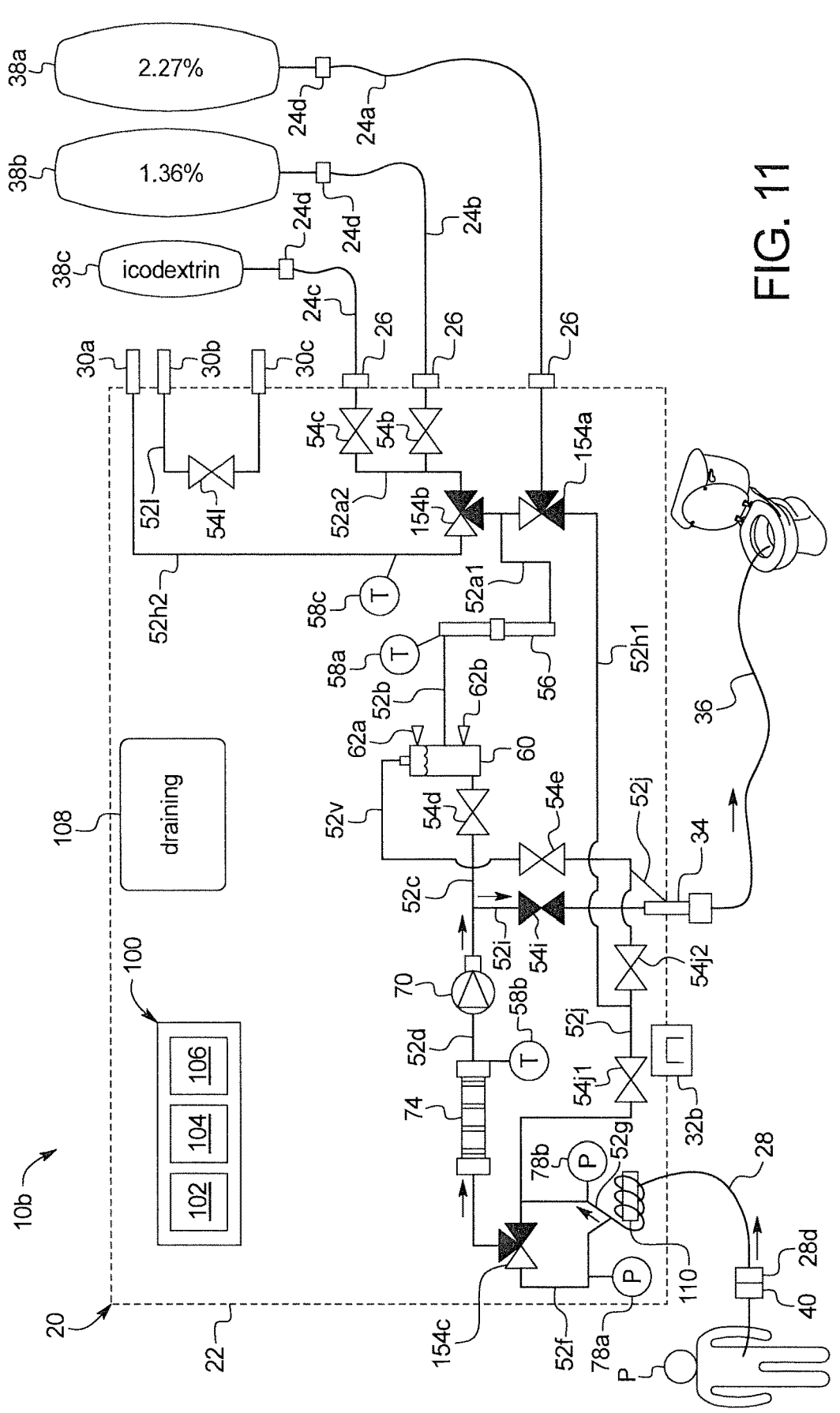
FIG. 11 is a schematic view illustrating a patient drain sequence for the second primary embodiment of the APD cycler and associated system of the present disclosure.

FIG. 11 illustrates one possible drain sequence (initial or subsequent drain) for system 10b operated via control unit 100. The initial drain sequence, assuming the patient is full of used PD fluid from a previous treatment when the patient begins a new treatment, begins after priming. The patient or caregiver removes reusable patient line 28 from patient line connector 32b provided at housing 22 of cycler 20 and connects distal end 28d of reusable patient line 28 to disposable filter set 40 (see FIG. 4) and then connects disposable filter set 40 to the patient's transfer set. As discussed herein, reusable patient line 28 may be uncoiled from a spool or hose reel 110 to extend to patient P. Patient P or caregiver could alternatively connect disposable filter set 40 to the patient's transfer set before connecting the disposable filter set to reusable patient line 28. It should be appreciated that the connections just described are the same for a patient fill occurring directly after priming.

The patient or caregiver then presses "start treatment" or "start drain" on user interface 108, e.g., via a touch screen. Control unit 100 causes treatment to begin, here with an initial drain from patient P via used dialysis fluid lumen 28*b*. Control unit 100 causes third three-way valve 154*c* to be set or oriented so as to allow used dialysis fluid to be pulled within used dialysis fluid lumen 28*b* via pump 70 running in reverse to then flow through used dialysis fluid patient tubing or line 52*g* into reusable line or tube 52*d*. Drain valve 54*i* is also opened so that the used dialysis fluid is pushed by pump 70 into drain line 52*i*, through drain line connector 34 and disposable drain line 36 to house drain or a drain container. Heater 56 again does not need to be actuated or energized. Dialysis fluid pump 70 in one embodiment is able to meter a precise amount of used dialysis fluid from patient P to drain, which is recorded by control unit 100. One or more pressure sensor 78*a* or 78*b* outputs to control draining pressure, for example, to or within −1.0 psig to −3.0 psig (e.g., −1.3 psig (−9 kPa)). Conductivity sensor 74 may be used as described above to evaluate the patient's effluent.

A second air trap or chamber (not illustrated) may be located between pump 70 and spool or hose reel 110 for the detection by control unit 100 of air due to a leaking patient connection or some internal leakage. Another air detection approach is for control unit 100 to look at the output from conductivity sensor 74 to detect air bubbles of some detectable size. Such air detection may provide sufficient mitigation against a leakage that is sufficient to affect the accuracy of a drained volume determination.

Figure 12:
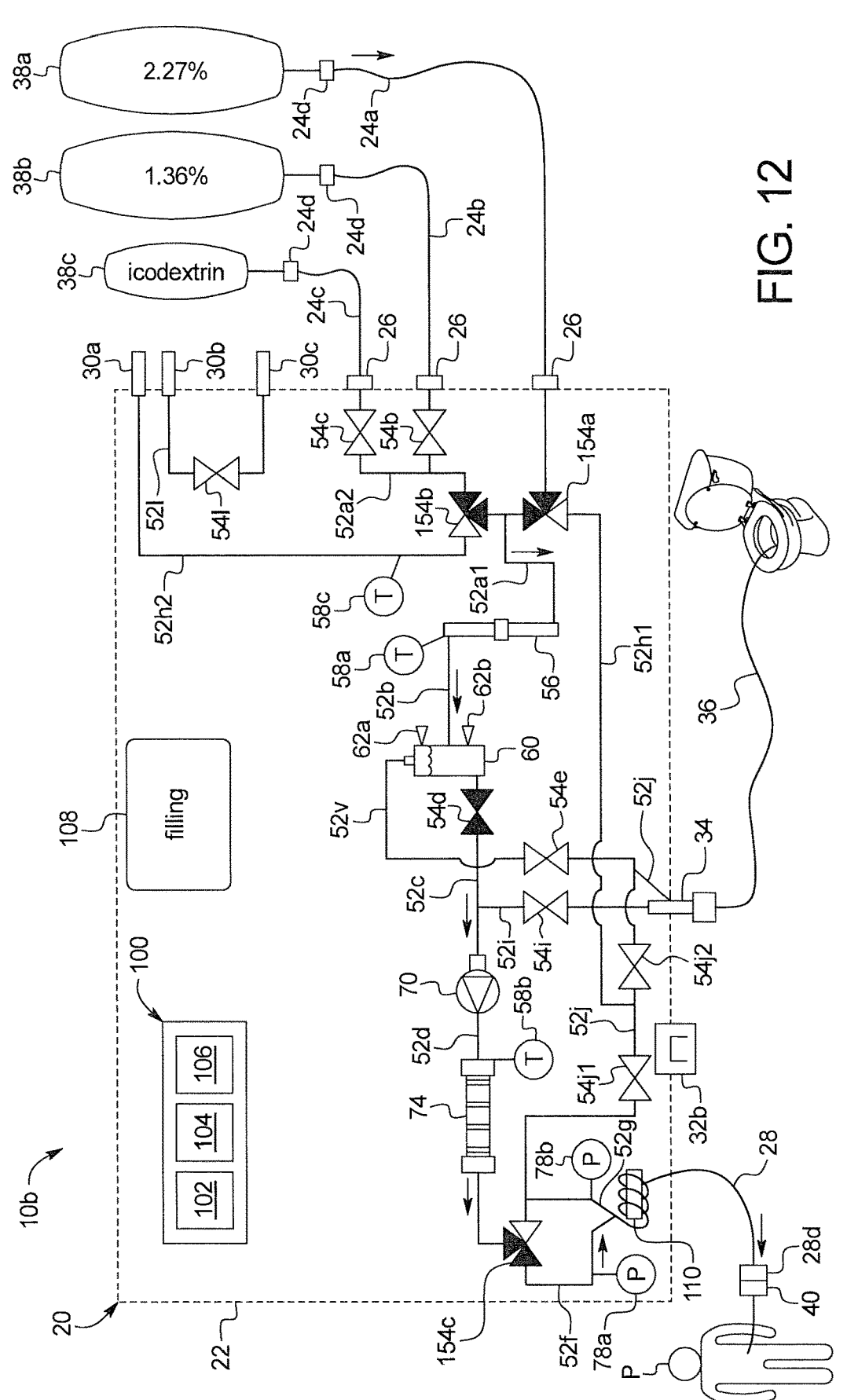
FIG. 12 is a schematic view illustrating a fill sequence for the second primary embodiment of the APD cycler and associated system of the present disclosure.

FIG. 12 illustrates one possible fill sequence for system 10*b* under control of control unit 100. If the patient fill occurs directly after priming then the patient or caregiver makes the connections discussed above with FIG. 11 and then presses "start fill" on user interface 108, e.g., via a touch screen. If, as here, the patient fill follows an initial patient drain, control unit 100 switches automatically to the patient fill when the patient drain is finished without requiring an input from patient P or the caregiver. Here, control unit 100 causes first and second three-way valves 154*a* and 154*b* (and other valves discussed above) to be set in the same states or orientations as described above for priming in FIG. 10. When PD fluid container or bag 38*a* has been emptied, valve 54*b* or 54*c* is opened and the state of three-way valve 154*a* is flipped to use PD fluid container or bag 38*b* or 38*c* instead.

Control unit causes air trap valve 54*d* to be open and third three-way valve 154*c* to be in a state or orientation such that fresh dialysis fluid flows through fresh dialysis fluid patient line 52*f* and fresh PD fluid lumen 28*a* to patient P. Inline heater 56 is actuated to heat fresh dialysis fluid to patient temperature, e.g., 37° C., as confirmed via at least one temperature sensor 58*a* and 58*b*. Level sensors 62*a* and 62*b* output to control unit 100, which controls pump 70 and three-way valves 154*a* to 154*c* to either fill or empty air trap 60 as needed. Outputs from at least one pressure sensor 78*a* and 78*b* is/are used to ensure that priming fluid pressure is within a safe positive pressure limit for patient P, for example, one to five psig (e.g., two psig (14 kPa)). The output from conductivity sensor 74 may be used to confirm that the fresh dialysis fluid type for the current patient fill is correct.

Figure 13:
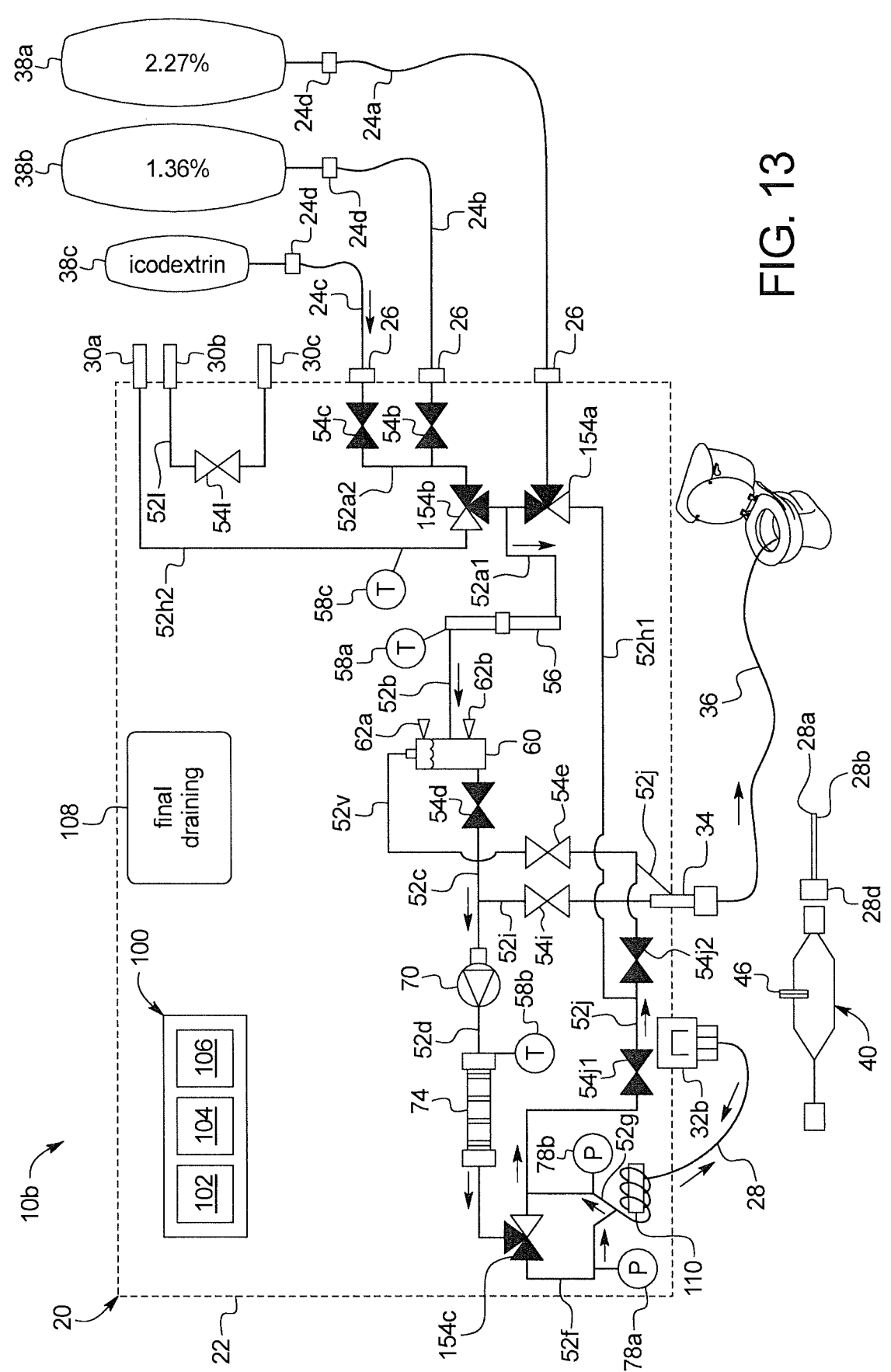
FIG. 13 is a schematic view illustrating a final drain sequence for the second primary embodiment of the APD cycler and associated system of the present disclosure.

FIG. 13 illustrates one possible final drain sequence for system 10*b* under control of control unit 100, which occurs, for example, after the final patient fill sequence and after the patient disconnects from reusable patient line 28 and plugs the line back into patient line connector 32*b*. As soon as control unit 100 detects that reusable patient line 28 is plugged into patient line connector 32*b* (e.g., via one or more pressure sensor 78*a* or 78*b* or via a separate proximity sensor or contact closure outputting to control unit 100 as described above), control unit 100 begins the final drain sequence. Here, control unit 100 orients (three-way valves) or opens (two-way valves) all patient supply valves 154*a*, 154*b*, 54*b* and 54*c* at once or sequences those valves open as needed to empty any non-emptied container or bag 38*a* to 38*c*. Air trap valve 54*d* and drain line valves 54*j*1 and 54*j*2 are opened and three-way valve 154*c* is set in a state or orientation to allow fresh dialysis fluid pump 70 to pump any remaining fresh dialysis fluid through reusable patient tubing or line 52*f*, through fresh dialysis fluid lumen 28*a*, through the recirculation lumen of patient line connector 32*b*, through used dialysis fluid lumen 28*b*, through reusable patient tubing or line 52*g*, through drain line 52*j* and through drain line connector 34 and drain line 36 to drain.

In an embodiment, control unit 100 knows how much fresh PD fluid has been removed from each container or bag 38*a* to 38*c* over the course of treatment and therefore knows which containers need to be emptied. Control unit 100 may keep track of the additional amount of fresh PD fluid removed from containers or bags 38*a* to 38*c* and stop dialysis fluid pump 70 when the accumulated amount meets or comes within a certain percentage of the supplied amount of PD fluid for the container. Alternatively or additionally, a separate flow switch (not illustrated) outputting to control unit 100 is provided, e.g., along tubing or line 52*a*.

In an embodiment, when the last connected container or bag 38*a* to 38*c* bag is emptied, control unit 100 of system 10*b* runs pump 70 to pump a calculated volume to empty as much fluid as possible from air trap 60 to drain. For this, three-way valve 154*b* switches position from that illustrated in FIG. 13, so that air may be pulled in through disinfection connector 30*a* to 30*c*, backfilling and allowing air trap 60 to be emptied. When air trap 60 has been emptied, control unit 100 then causes valve 154*b* to be set in a position interconnecting lines 52*a*1 and 52*h*2 and air trap valve 54*d* to open. Control unit 100 may then run pump 70 in a normal treatment direction to pull air into cycler 20, emptying PD fluid from chamber 60 and all lines further downstream from the chamber to drain line 36. In an alternative embodiment, fluid remaining in air trap 60 may be used during disinfection to fill disinfection tubing or line 52*h*1, 52*h*2 and 52*l*. Here, containers or bags 38*a* to 38*c* are emptied at the end of treatment so that the patient has less weight to carry, but cycler 20 is left full of fresh dialysis fluid for disinfection.

Figure 14:
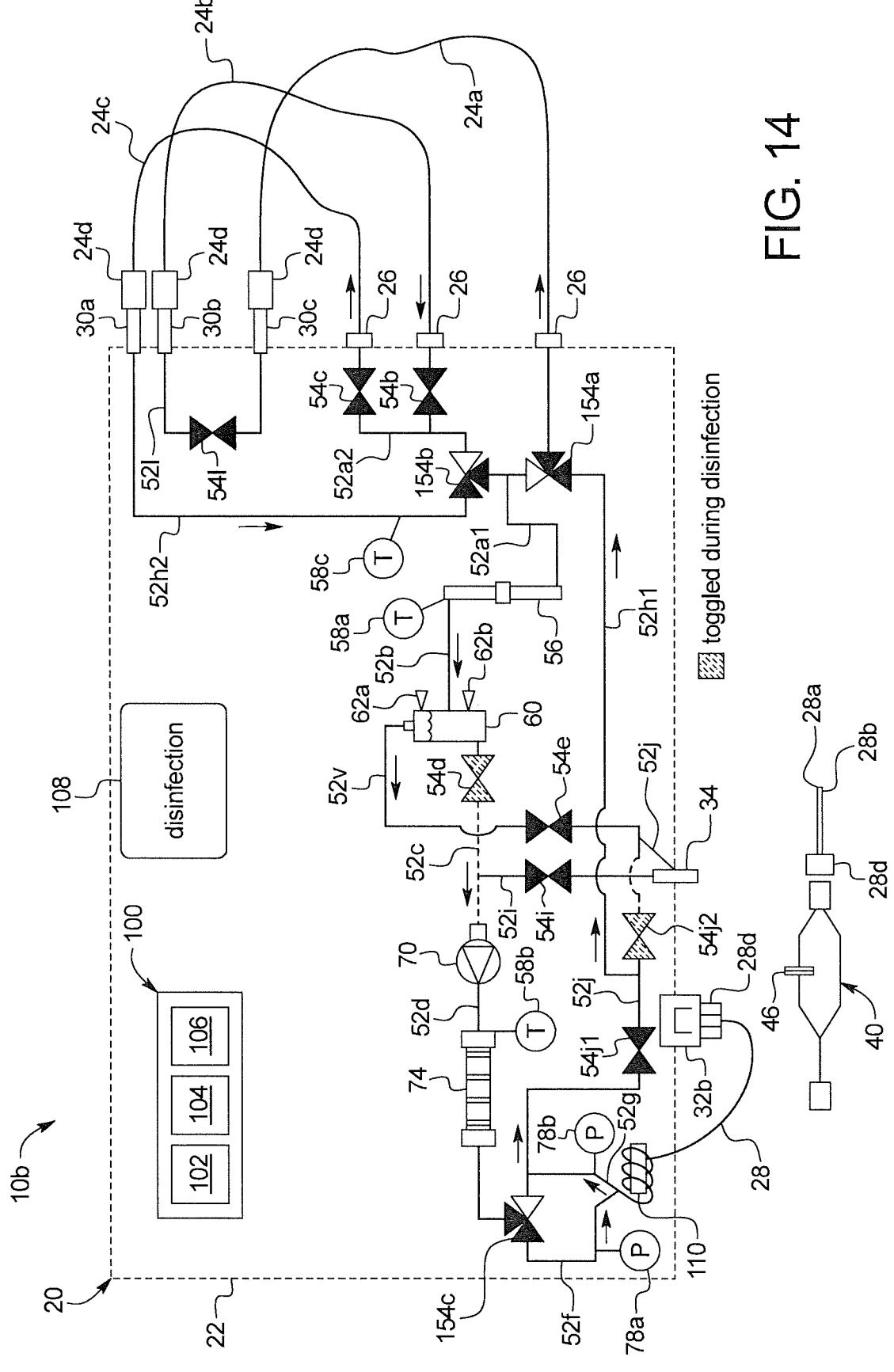
FIG. 14 is a schematic view illustrating a disinfection sequence for the second primary embodiment of the APD cycler and associated system of the present disclosure.

As illustrated in FIG. 14, at the end of treatment, control unit 100 in one embodiment automatically runs a disinfection sequence using a disinfection circuit 50 in which reusable patient line 28 is connected to patient line connector 32*b*, drain line connector 34 is covered or capped by rotatable or slideable cover 34*c* (see FIG. 3), and PD fluid lines 24*a* to 24*c* are plugged into disinfection connectors 30*a* to 30*c*. Control unit 100 in one embodiment opens all two-way fluid valves 54*b* to 54*e*, 54*i*, 54*j*1, 54*j*2 and 54*l* to form disinfection circuit 50. In another embodiment, certain two-way valves, e.g., supply valves 54*b* and 54*c*, may be closed or toggled open and closed during disinfection. Control unit 100 sets first three-way valve 154*a* so that PD fluid line 24*a* communicates fluidly with disinfection tubing or line 52*h*1. Second and third three-way valves 154*b* and 154*c* are toggled via control unit 100 at some desired frequency so that heated disinfection fluid, e.g., fresh dialysis fluid, contacts both fluid pathways controlled by the three-way valves. Likewise, air trap valve 54*d* may be toggled open and closed via control unit 100 at some desired frequency to allow air trap 60 to be filled completely with heated disinfection fluid and for disinfection fluid to flow into vent line 52*v* for disinfection.

Heated disinfection fluid, e.g., unused fresh PD fluid, is also pumped through both lumens 28*a* and 28*b* of reusable patient line 28 and the recirculation lumen of patient connector 32*b*. Heated disinfection fluid is likewise pumped through all fluid pathways of drain line connector 34. Disinfection pathway 52*l* allows disinfection connectors 30*b* and 30*c* and associated PD fluid lines 24*b* and 24*c*, respectively, to be fully disinfected, while disinfection pathway 52*h*2 does the same for disinfection connector 30*a* and associated PD fluid line 24*a*.

Control unit 100 runs dialysis fluid pump 70 and actuates heater 56 to pump heated (e.g., to 70° C. or greater) fresh PD fluid, used PD fluid, a combination of fresh and used PD fluid or some other dedicated disinfection fluid continuously throughout disinfection circuit 50, e.g., for a set amount of time, such as 120 minutes. One or both pressure sensors 78*a* and/or 78*b* may be used at the beginning of the disinfection sequence for control unit 100 to see if a disinfection pressure is reached and if not to determine that one of the disinfection connections has not been made or made correctly, and thereby halt the disinfection and post an audio, visual or audiovisual alarm at user interface 108. It is contemplated for control unit 100 to reverse dialysis fluid pump 70 one or more time during the disinfection sequence (arrows would run in reverse to those shown in FIG. 14) and/or allow a certain amount of air to fill a portion of disinfection circuit 50 during the disinfection sequence to increase turbulence and impact force on the insides of the lines or tubing forming disinfection circuit 50. Dialysis fluid pump 70 may also be run at a maximum safe pressure and flowrate for system 10*b* to likewise achieve better disinfection.

As discussed above for system 10*a*, the disinfection sequence described in connection with FIG. 14 for system 10*b* may end with a drain and rinse, a drain only or no drain or rinse (disinfection fluid left within cycler 20 until the next treatment). Again, the drain and possibly the rinse may be performed by connecting the next treatment's drain line 36 to drain line connector 34 after disinfection, allowing the disinfection fluid and possibly the rinse fluid to be pumped to house drain or a drain container. The drain line 36 may then be clamped at its distal end if needed (e.g., when using house drain) to wait for the next treatment. The rinse fluid may be a specialized rinse fluid or fluid from one of the next treatment's PD fluid containers 38*a* to 38*c* connected to one of reusable PD fluid lines 24*a* to 24*c*.

Third Primary Embodiment

Referring now to FIGS. 15 to 21, an alternative APD system employing disinfection is illustrated by system 10*c*. System 10*c* includes many of the same components as systems 10*a* and 10*b*, which are generally numbered the same and include all structure, functionality and alternatives discussed above for those systems. For example, system 10*c* includes cycler 20 and control unit 100 having one or more processor 102, one or more memory 104 and a video controller 106. System 10*c* includes PD fluid containers or bags 38*a* to 38*c* (e.g., holding different formulations of PD fluid), which connect to distal ends 24*d* of reusable PD fluid lines 24*a* to 24*c*, respectively. Reusable PD fluid lines 24*a* to 24*c* extend from apertures 26 defined or provided by housing 22 of cycler 20 (see FIG. 1). System 10*c* includes inline dialysis fluid heater 56, reusable line or tubing 52*b*, air trap 60 operating with respective upper and lower level sensors 62*a* and 62*b*, air trap valve 54*d*, vent valve 54*e*, reusable line or tubing 52*c*, dialysis fluid pump 70, temperature sensors 58*a* and 58*b*, reusable line or tubing 52*d*, pressure sensors 78*a*, 78*b*1 and 78*b*2, reusable patient tubing or lines 52*f* and 52*g*, hose reel 110, dual lumen reusable patient line 28, reusable drain tubing or line 52*i* extending to drain line connector 34 and having a drain line valve 54*i*, and reusable disinfection tubing or lines 52*h*1 and 52*h*2 operating with respective disinfection valves 54*h*1 and 54*h*2. FIGS. 15 to 21 also illustrate that system 10*c* includes and uses disposable filter set 40, which communicates fluidly with fresh PD fluid lumen 28*a* and used PD fluid lumen 28*b* of dual lumen reusable patient line 28. Each of pump 70, heater 56, the valves and sensors is controlled by and/or outputs to control unit 100.

System 10*c* does not illustrate but may still provide a conductivity sensor 74 outputting to control unit 100 for any of the reasons or uses discussed herein.

As with systems 10*a* and 10*b*, system 10*c* includes disinfection connectors 30*a* to 30*c* for connecting to distal ends 24*d* of reusable PD fluid lines 24*a* to 24*c*, respectively, during disinfection. A third disinfection tubing or line 52*h*3 extends between disinfection connectors 30*a* and 30*b* for use during disinfection. System 10*c* also employs patient line connector 32*b* discussed in connection with system 10*b*, which includes an internal lumen, e.g., a U-shaped lumen, which directs fresh or used dialysis fluid from one PD fluid lumen 28*a* or 28*b* of dual lumen reusable patient line 28 into the other PD fluid lumen 28*b* or 28*a*. System 10*c* further includes reusable supply tubing or lines 52*a*1 to 52*a*3, which communicate with reusable supply lines 24*a* to 24*c* and operate with valves 54*a* to 54*c*, respectively, to allow PD fluid from a desired PD fluid container or bag 38*a* to 38*c* into cycler 20.

One primary difference with system 10*c* is that, unlike systems 10*a* and 10*b*, drain line 52*i* during filling is fluidly connected downstream from dialysis fluid pump 70. In this manner, if drain valve 54*i* fails or somehow leaks during a patient fill, fresh PD fluid is pushed down disposable drain line 36 instead of used PD fluid potentially being pulled into pump 70 as in systems 10*a* and 10*b*. In system 10*c*, both valves 54*g* and 54*h*2 protect against used dialysis fluid being pulled from drain line connector 34 or drain line during patient filling.

An addition to system 10*c*, which may be provided in any of the systems discussed herein, is the provision of a flow switch 80 outputting to control unit 100. Flow switch 80 is set to trip or output at a designated low flowrate, which is indicative of one of containers or bags 38*a* to 38*c* becoming empty, and which may also be used to ensure that fresh PD fluid is flowing through inline heater 56 when the heater is powered for fluid heating. Control unit 100 may for example be programmed to use the output from flow switch 80 (i) during a final drain of all containers at the end of treatment and/or (ii) at the beginning of the disinfection sequence while filling disinfection circuit 50 to know when one container 38*a* to 38*c* is empty so that the filling may transition to use another container. Flow switch 80 may alternatively be a flow sensor having a variable output.

Another addition to system 10*c*, which may be provided in any of the systems discussed herein, is the provision of a leak detection pan 82 located at the bottom of housing 22 of cycler 20 and a corresponding leak detection sensor 84 outputting to control unit 100. Leak detection pan 82 may be made of any of the materials discussed herein and is angled or funneled to have an angle or funnel shape, which collects any type of fluid (fresh or used PD fluid, disinfection fluid, flush flow fluid, RO or distilled water) that falls from the reusable tubing of cycler 20 due to a faulty connection, ruptured material, or other reason. Leak detection sensor 84 in one embodiment does not contact the leaked fluid directly and may be any type of sensor discussed herein for level sensors 62a and 62b, e.g., ultrasonic, inductive, capacitive and/or optical. Leak detection sensor 84 may alternatively directly contact the leaked material, e.g., via an electrical contact closure sensor. Combinations of different types of sensors 84 and multiple sensors 84 may be provided as needed. Upon receiving a fluid leak signal from leak detection sensor 84, control unit 100 alarms and possibly sends a communication automatically to a network service portal indicating that a temporary replacement cycler is needed while the leaking cycler is repaired.

A further addition to system 10c, which may be provided in any of the systems discussed herein, is the optional addition of a pressure sensor 78c upstream of pump 70. Measuring the suction pressure of pump 70 may help control unit 100 to more accurately determine pump volume. For example, the output of certain piston pumps is dependent on inlet pressure. Another use for pressure sensor 78c is to determine if a currently used container or bag 38a to 38c has or is near empty. Here again, the empty determination may be used (i) during a final drain of all containers at the end of treatment and/or (ii) at the beginning of disinfection while filling the cycler circuit to know when one container 38a to 38c is empty so that the filling may transition to use another container. Thus pressure sensor 78c may negate the need for flow switch 80 or be used in addition to the switch.

Yet another addition to system 10c, which may be provided in any of the systems discussed herein, is the provision of redundant pressure sensors 78b1 and 78b2 (and possibly for pressure sensor 78a). Here, one sensor, e.g., sensor 78b1, is used for pump control as discussed herein, while the other pressure sensor, e.g., sensor 78b2, is a safety sensor or watchdog sensor to make sure control sensor 78b1 is reading accurately. If not, control unit 100 alarms and potentially sends a communication automatically to a network service portal indicating that a recalibration of control sensor 78b1 (or both sensors) is needed.

Still a further addition to system 10c, which may be provided in any of the systems discussed herein, is the provision of fluidic crosses, which are marked via an X in FIGS. 15 to 21. The fluidic crosses help reduce the overall amount and volume of the internal, reusable tubing for cycler 20 of system 10c, and may also reduce the number of valves needed. The crosses may also allow the portion of the fluid circuitry of cycler 20 that is shared by both fresh and used PD fluid to be minimized.

FIGS. 15 to 18 illustrate separate portions of one embodiment for a priming sequence for system 10c. As with the figures for systems 10a and 10b, darkened valves are open at least at some point within the sequence portion. The arrows show one embodiment for the direction of fresh or used dialysis fluid flow. Note also that reusable patient line 28 is connected to patient line connector 32b for each of FIGS. 15 to 18. It should be appreciated that the order of the priming sequence portions in FIGS. 15 to 18 may be shuffled, reversed or modified as desired, however, it may be preferred to prime initially from a larger source of fresh PD fluid, e.g., containers 38a and 38b holding for example 1.36%, 2.27% or 3.86% glucose PD fluid, which are used over the course of treatment, rather than a smaller container

38c holding for example icodextrin, which is only used for a last fill. Or, regardless of order, the priming using icodextrin may be only for priming its associated reusable PD fluid line 24c, wherein fresh PD fluid from one or more of the other containers is used to prime the remainder of the fluid circuit of cycler 20.

Figure 15:
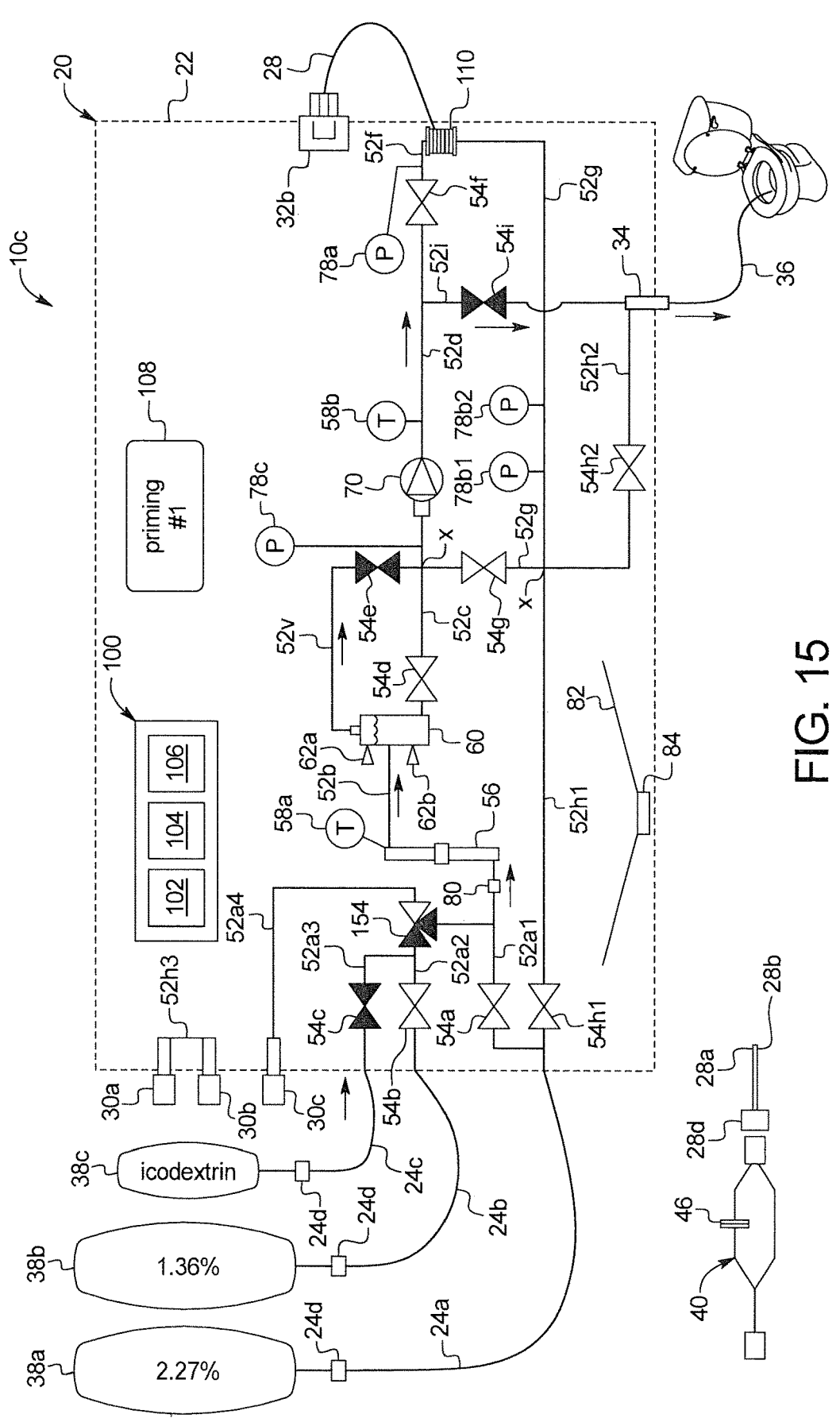
FIG. 15 is a schematic view illustrating a first portion of an example priming sequence for a third primary embodiment of the APD cycler and associated system of the present disclosure.

In FIG. 15, control unit 100 causes three-way valve 154 to be oriented in a treatment orientation and two-way supply valve 54c, vent valve 54e and drain valve 54i to be opened to allow fresh PD fluid to be pulled from PD fluid container or bag 38c and to prime reusable PD fluid line 24c, supply line 52a3, dialysis fluid line 52b, vent line 52v, dialysis fluid line 52d and drain line 52i to drain line 36. In an alternative embodiment, since PD fluid container or bag 38c holds icodextrin, the priming in FIG. 15 may instead be only from container or bag 38c, through PD fluid line 24c, to three-way valve 154, wherein valves 54e and 54i are instead closed.

Figure 16:
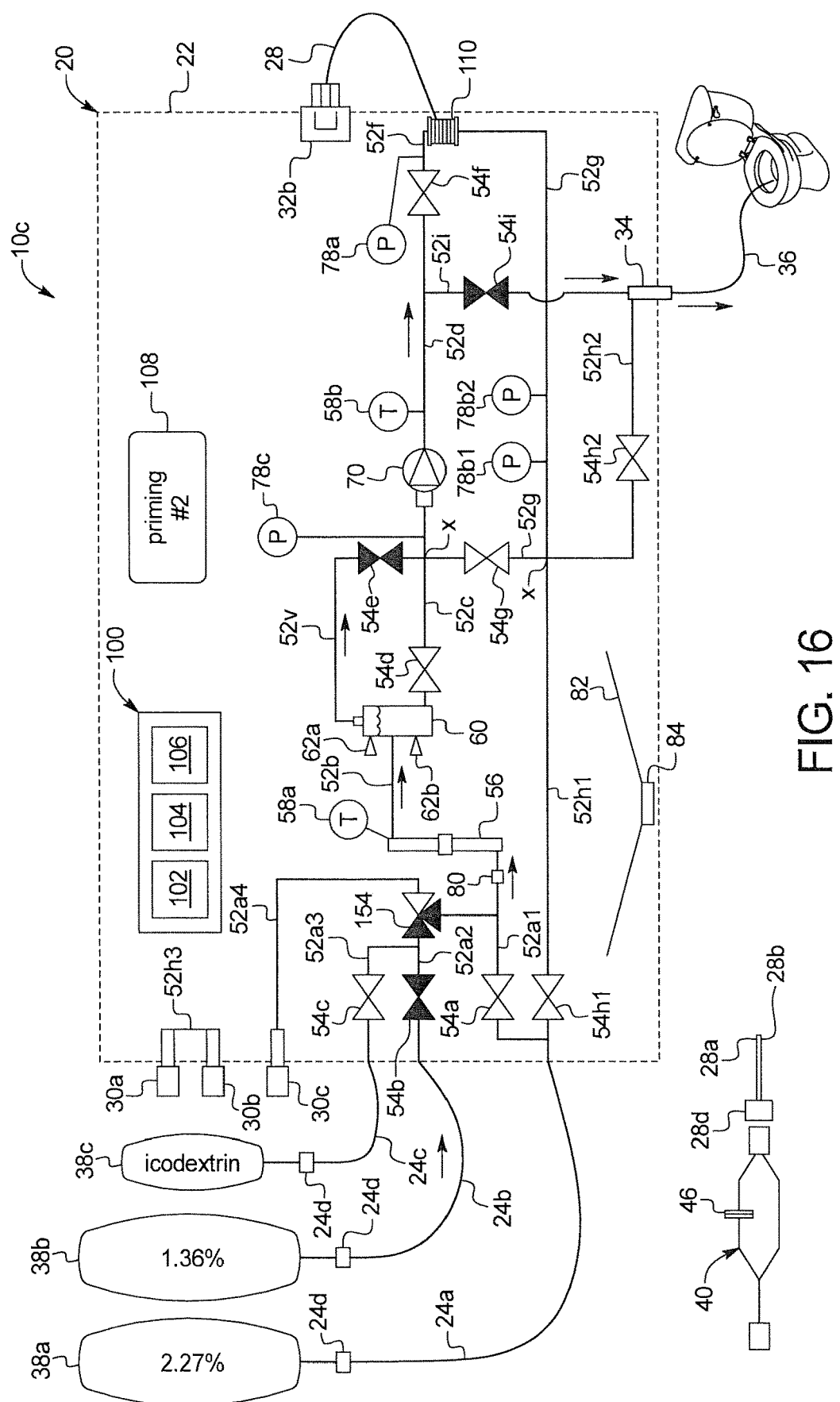
FIG. 16 is a schematic view illustrating a second portion of an example priming sequence for the third primary embodiment of the APD cycler and associated system of the present disclosure.

In FIG. 16, control unit 100 causes three-way valve 154 to be oriented in a treatment orientation and two-way supply valve 54b, vent valve 54e and drain valve 54i to be opened to allow fresh PD fluid to be pulled from PD fluid container or bag 38b and to prime reusable PD fluid line 24b, supply line 52a2, dialysis fluid line 52b, vent line 52v, dialysis fluid line 52d and drain line 52i to drain 36.

Figure 17:
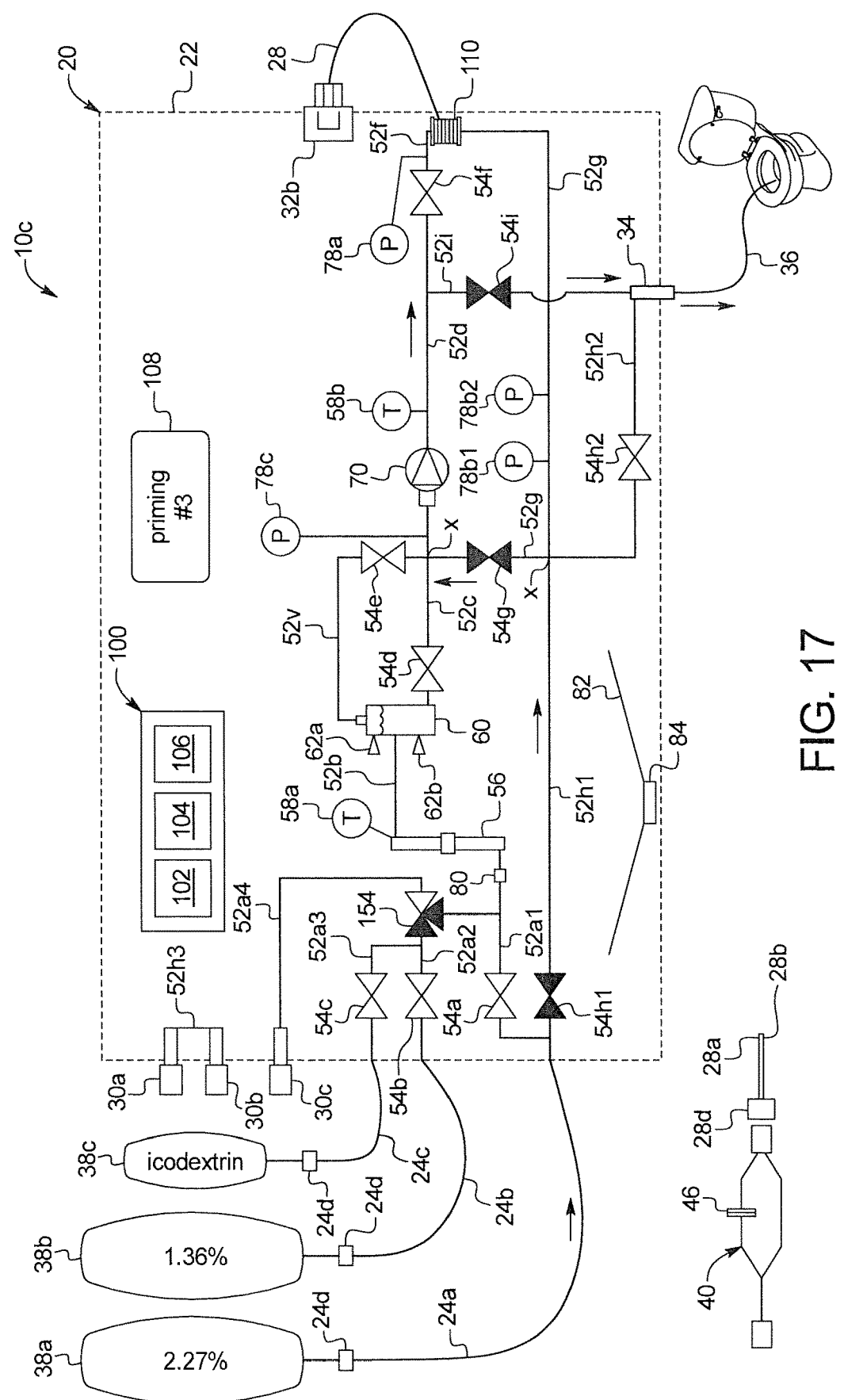
FIG. 17 is a schematic view illustrating a third portion of an example priming sequence for the third primary embodiment of the APD cycler and associated system of the present disclosure.

In FIG. 17, control unit 100 causes three-way valve 154 to be oriented in a treatment orientation (although not needed for the flowpath), two-way disinfection valve 54h1, patient valve 54g and drain valve 52i to be opened to allow fresh PD fluid to be pulled from PD fluid container or bag 38a and to prime reusable PD fluid line 24a, disinfection line 52h1, a portion of patient line 52g, dialysis fluid line 52d and drain line 52i to drain.

Figure 18:
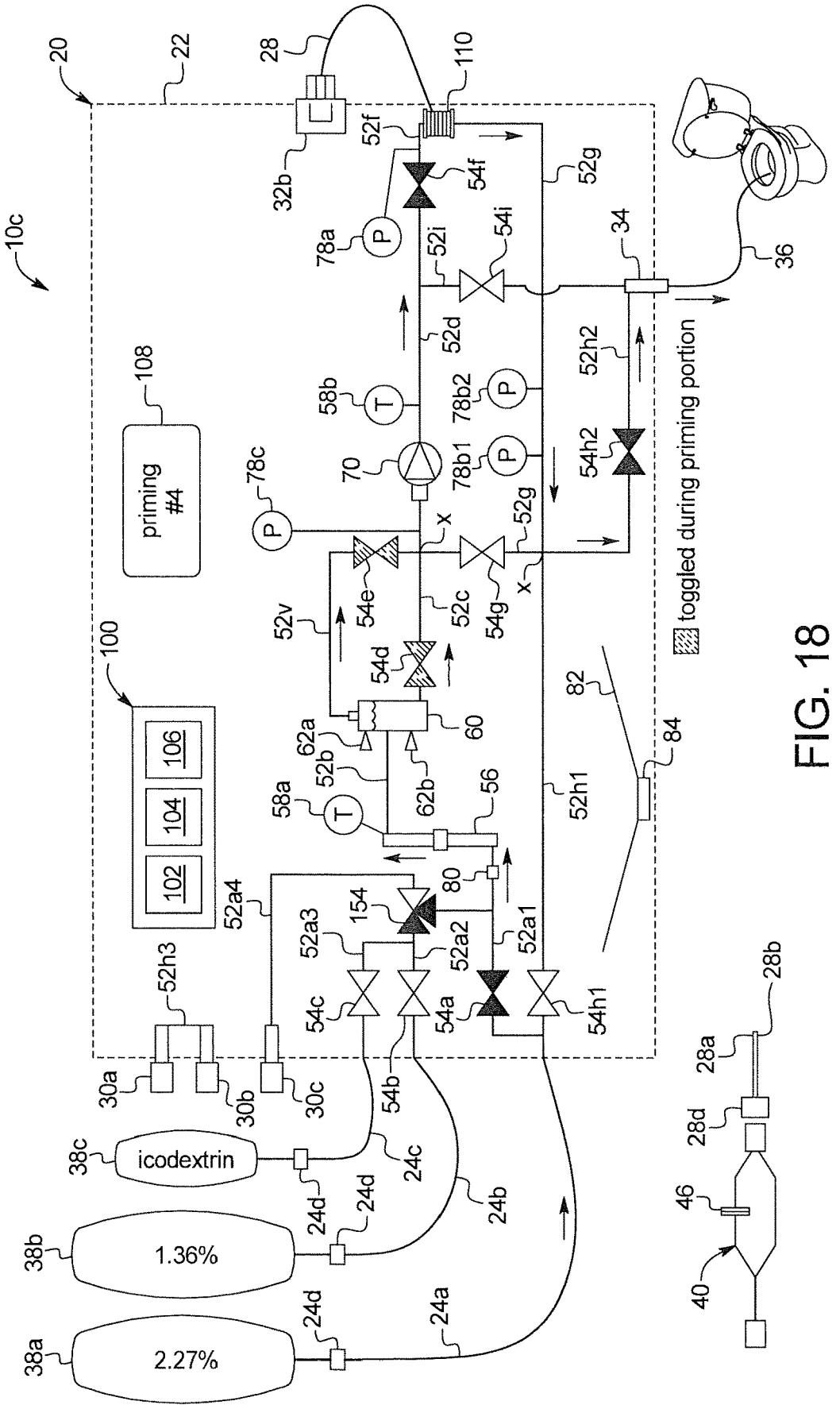
FIG. 18 is a schematic view illustrating a fourth portion of an example priming sequence for the third primary embodiment of the APD cycler and associated system of the present disclosure.

In FIG. 18, control unit 100 causes three-way valve 154 to be oriented in a treatment orientation (although not needed for the flowpath), two-way supply valve 54a, patient valve 54f and disinfection valve 54h2 to be opened, and drip chamber valve 54d and vent valve 54e to be toggled opened and closed to allow fresh PD fluid to be pulled from PD fluid container or bag 38a and to prime reusable PD fluid line 24a, supply line 52a1, dialysis fluid line 52b, dialysis fluid line 52c and vent line 52v alternatively due to the toggling, dialysis fluid line 52d, patient line 52f, a portion of patient line 52g and disinfection line 52h2 to drain.

FIGS. 17 and 18 illustrate that the same container 38a may be used to prime different portions of the fluid circuit of cycler 20. In the same way, container 38a may be used to prime the portion of the fluid circuit primed in FIG. 16, wherein container 38b in FIG. 16 is used only to prime up to three-way valve 154. Further alternatively, the roles of containers 38a and 38b may be reversed, wherein container 38b is used to prime the majority of the fluid circuit and container 38b is used only to prime up to valves 54a and 54h1.

Figure 19:
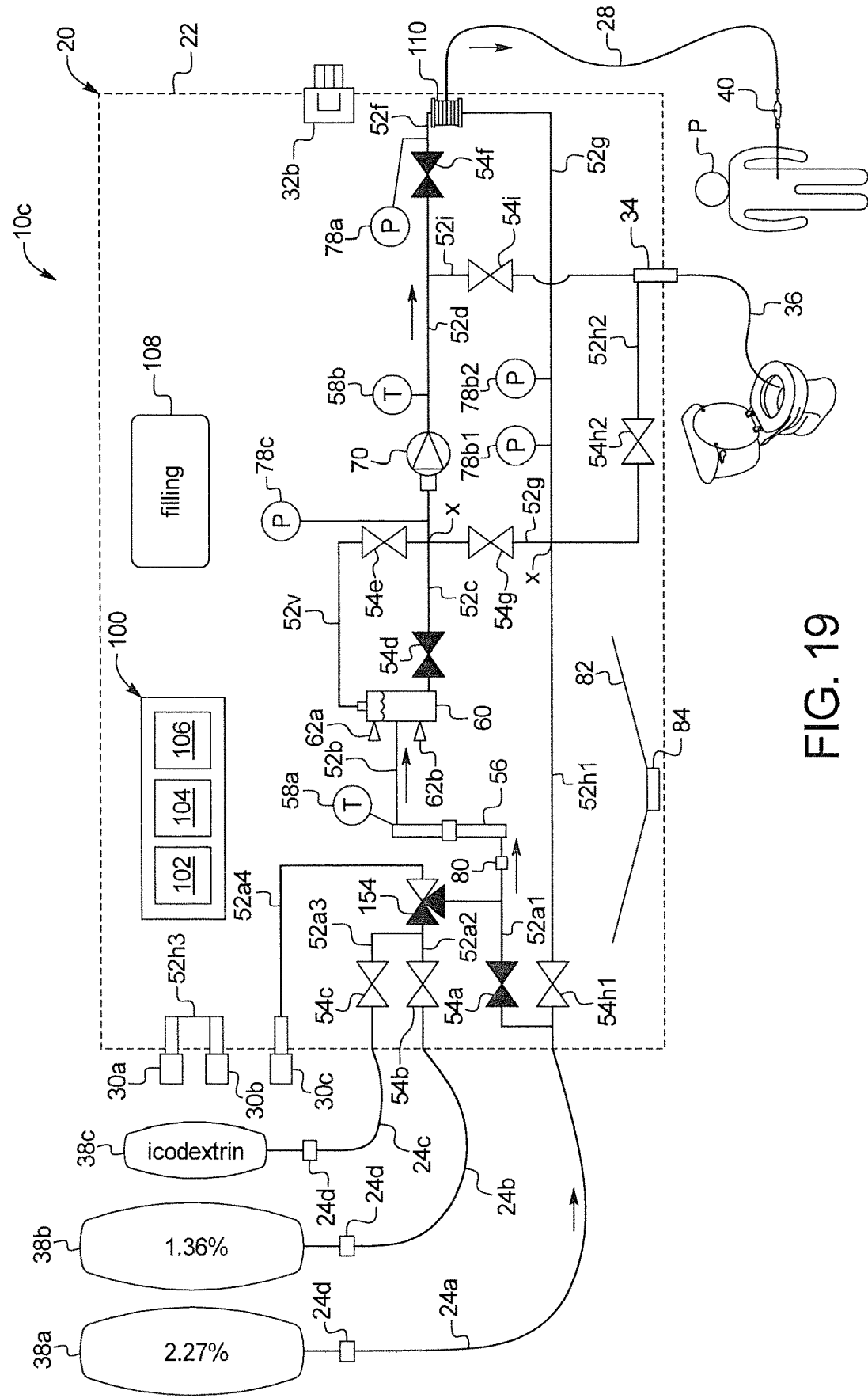
FIG. 19 is a schematic view illustrating an example patient filling sequence for the third primary embodiment of the APD cycler and associated system of the present disclosure.

FIG. 19 illustrates one embodiment for a patient fill using system 10c. FIG. 19 illustrates the patient fill coming from PD fluid container or bag 38a, however, the orientation of three-way valve 154 and the opened two-way PD valve 54d and patient valve 54f remain the same for each PD fluid container or bag 38a to 38c. To use PD fluid container or bag 38a, control unit 100 causes supply valve 54a to be opened as illustrated. To use PD fluid container or bag 38b, control unit 100 causes supply valve 54b to be opened. To use PD fluid container or bag 38c, control unit 100 causes supply valve 54c to be opened. Control unit 100 also causes inline heater 56 to heat fresh PD fluid to body or other desired temperature using feedback from at least temperature sensor 58a as discussed herein. Control unit 100 also causes dialysis fluid pump 70, e.g., an inherently volumetrically accurate piston pump, to meter a precise amount of fresh PD fluid through PD fluid lines 52b, 52c, 52d, patient line 52f, fresh PD lumen 28a and disposable filter set 40 to patient P. Pumping pressure is controlled to a safe positive pressure at the machine via feedback from pressure sensors 78a and 78b1 or 78b2 as discussed herein, e.g., using IPP via return lumen 28b as described above, to one to five psig (e.g., two psig (14 kPa)). Note that disposable filter set 40 shown unused in FIGS. 15 to 18 is connected and in use for the patient filling of FIG. 19.

Figure 20:
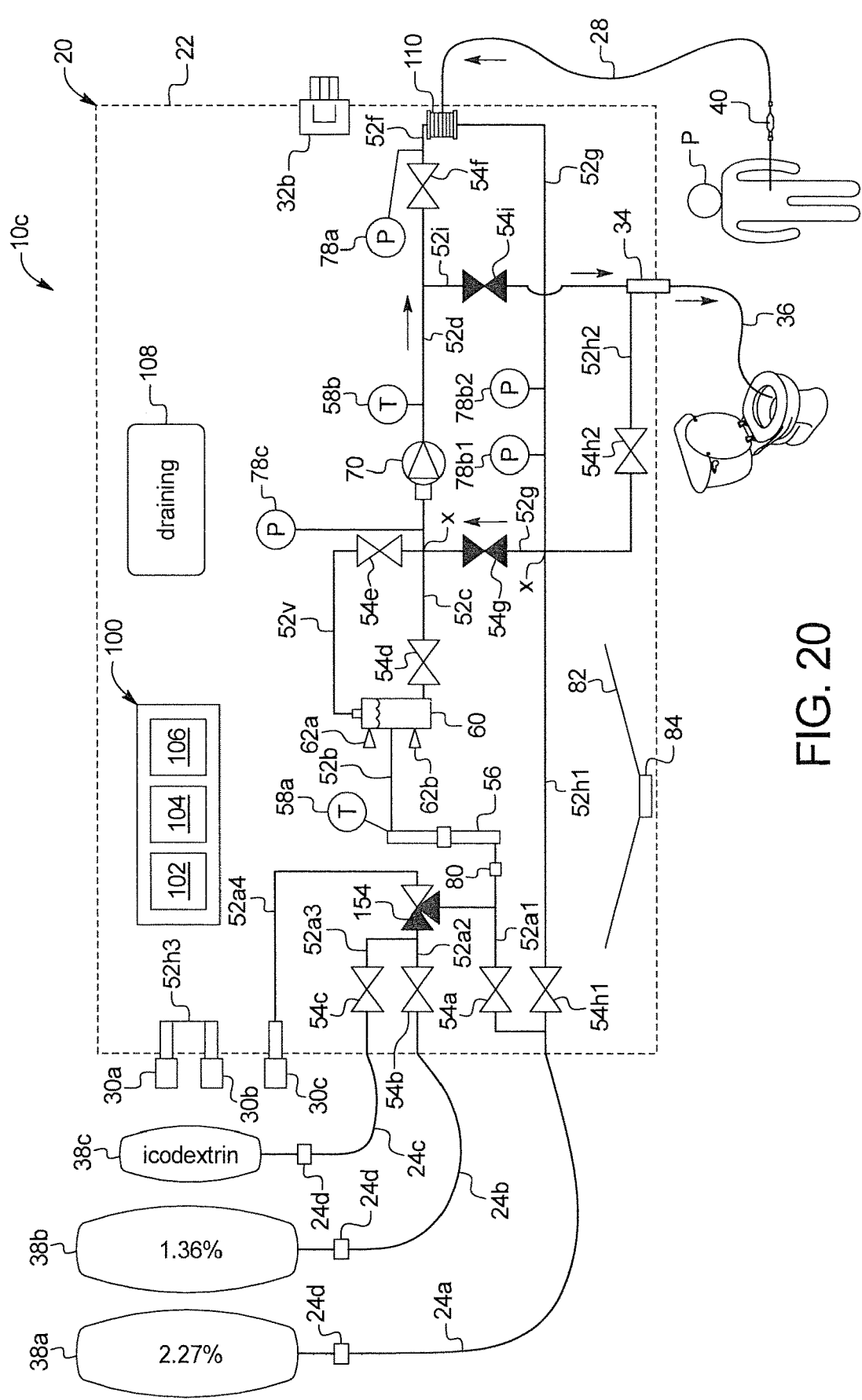
FIG. 20 is a schematic view illustrating an example patient draining sequence for the third primary embodiment of the APD cycler and associated system of the present disclosure.

FIG. 20 illustrates one embodiment for a patient drain using system 10c. FIG. 20 illustrates that all supply valves 54a, 54b and 54c are closed as is disinfection valve 54h1. Control unit 100 causes patient valve 54g and drain valve 54i to open to allow PD fluid pump 70 to pump used dialysis fluid from patient P, through used PD lumen 28b, patient line 52g, PD fluid line 52d, reusable drain line 52i and disposable drain line 36 to house drain or a drain container. As discussed herein, the patient drain may end upon removing a precise amount of effluent and/or by sensing a characteristic increase in negative pressure signaling that patient P is or is almost empty. Pumping pressure is controlled to a safe negative pressure at the machine via feedback from pressure sensors 78a and 78b1 or 78b2 as discussed herein, e.g., using IPP via fill lumen 28a as described above, to −1.0 psig to −3.0 psig (e.g., −1.3 psig (−9 kPa)). Note that disposable filter set 40 shown unused in FIGS. 15 to 18 is connected and in use for the patient draining of FIG. 20. Also, as has been described herein, the patient drain (FIG. 20) may be performed before the patient fill (FIG. 19) if patient P begins treatment full of effluent from a previous treatment or an intermediate exchange.

Figure 21:
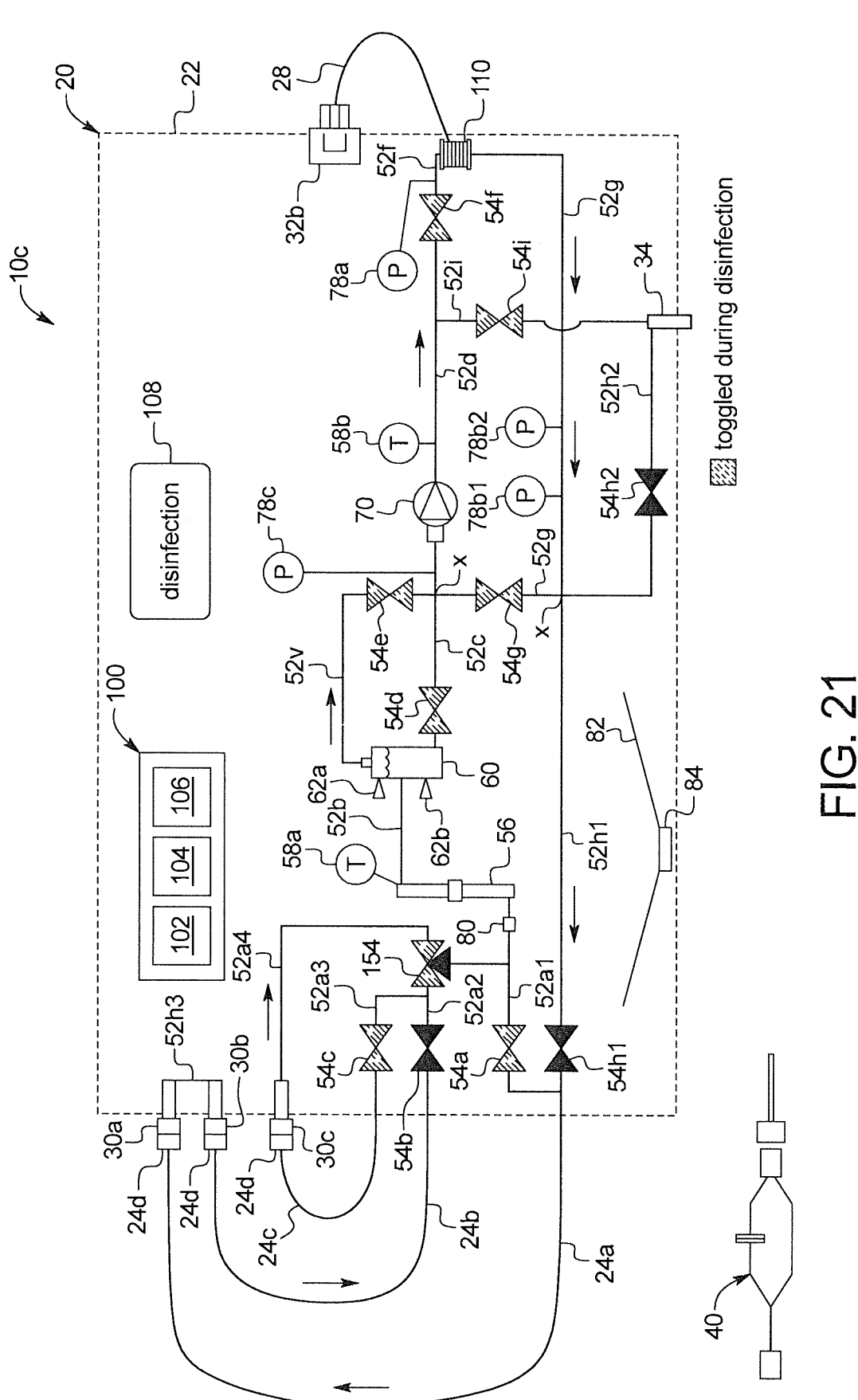
FIG. 21 is a schematic view illustrating an example disinfection sequence for the third primary embodiment of the APD cycler and associated system of the present disclosure.

FIG. 21 illustrates one embodiment for a disinfection sequence using system 10c. As illustrated, PD fluid containers or bags 38a to 38c are removed from reusable PD fluid lines 24a to 24c, respectively, after a final draining of the containers and a filling of the reusable cycler tubing or lines for disinfection (unless a different disinfection fluid is used). Distal ends 24d of reusable PD fluid lines 24a to 24c are connected respectively to disinfection connectors 30a to 30c. Disposable filter set 40 is removed from reusable patient line 28, which is then connected to patient line connector 32b. FIG. 21 illustrates that control unit 100 causes certain valves to remain open (fully darkened), while other valves are toggled (hatched lines) during the disinfection sequence. It should be appreciated that the valves that are opened versus the ones that are toggled may be modified from the arrangement illustrated in FIG. 21. Three-way valve 154 is likely toggled between supply lines 52a2, 52a3 and disinfection connector line 52a4 in any valve open versus toggle arrangement. Control unit 100 may cause pump 70 to run in one direction or switch back and forth in two directions one or more time. During the disinfection sequence, control unit 100 causes heater 56 to heat the disinfection fluid (e.g., fresh PD fluid) to a disinfection temperature, e.g., 70° C. or greater. The disinfection sequence lasts for a specified period of time to provide a proper disinfection dose A0.

Fourth Primary Embodiment

Figure 22:
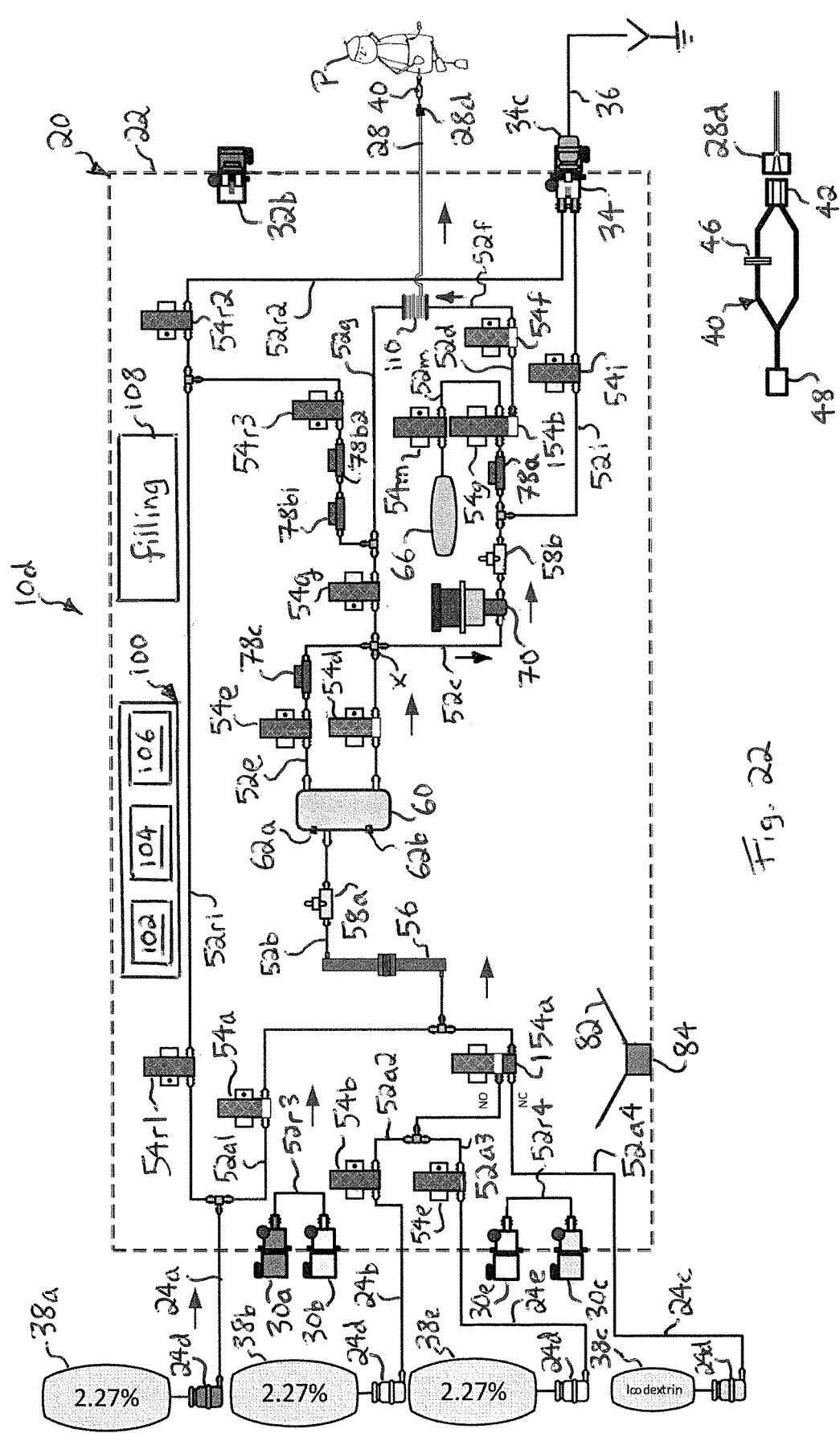
FIG. 22 is a schematic view illustrating an example patient filling sequence for a fourth primary embodiment of the APD cycler and associated system of the present disclosure.
Figure 23:
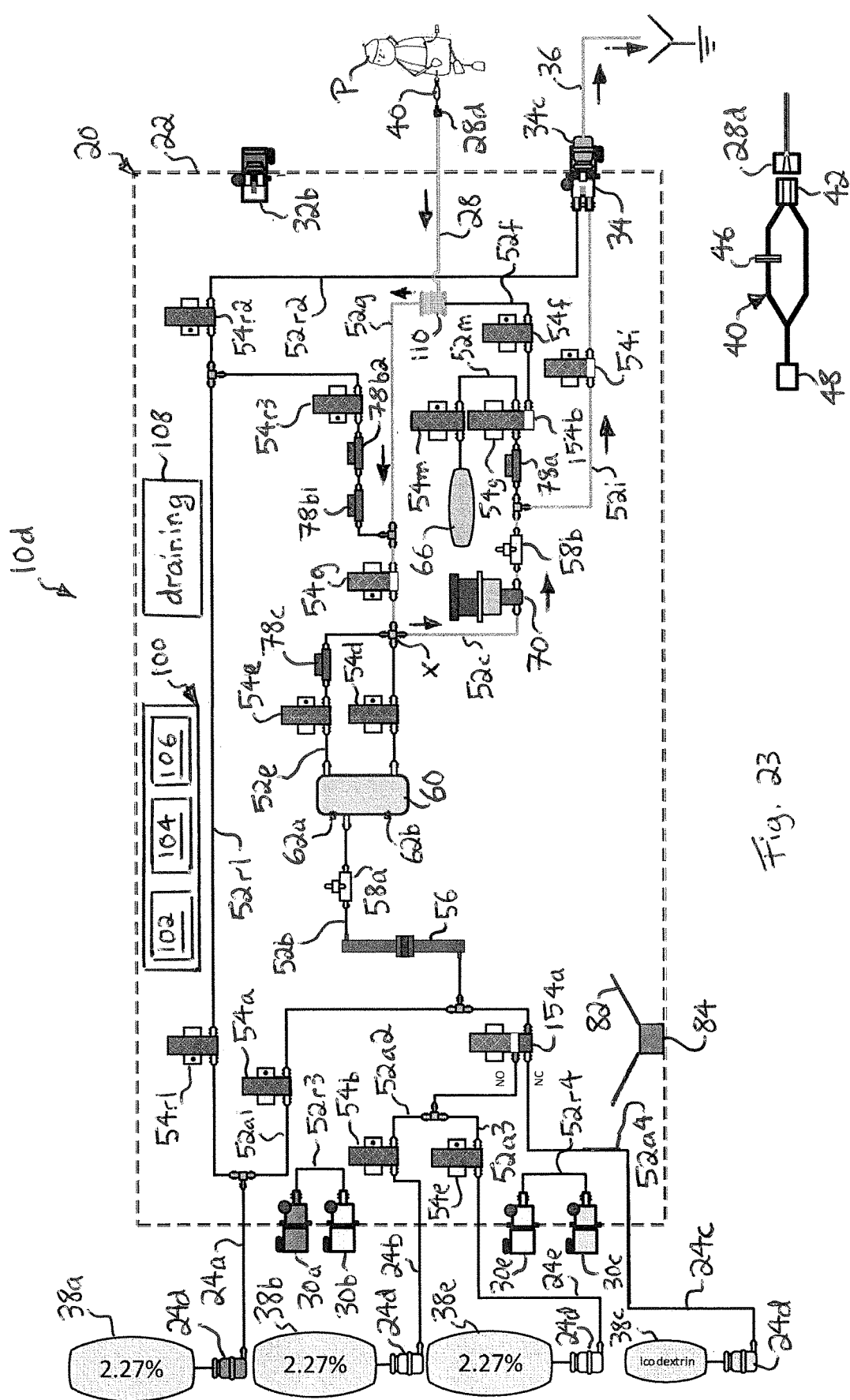
FIG. 23 is a schematic view illustrating an example patient draining sequence for the fourth primary embodiment of the APD cycler and associated system of the present disclosure.
Figure 24:
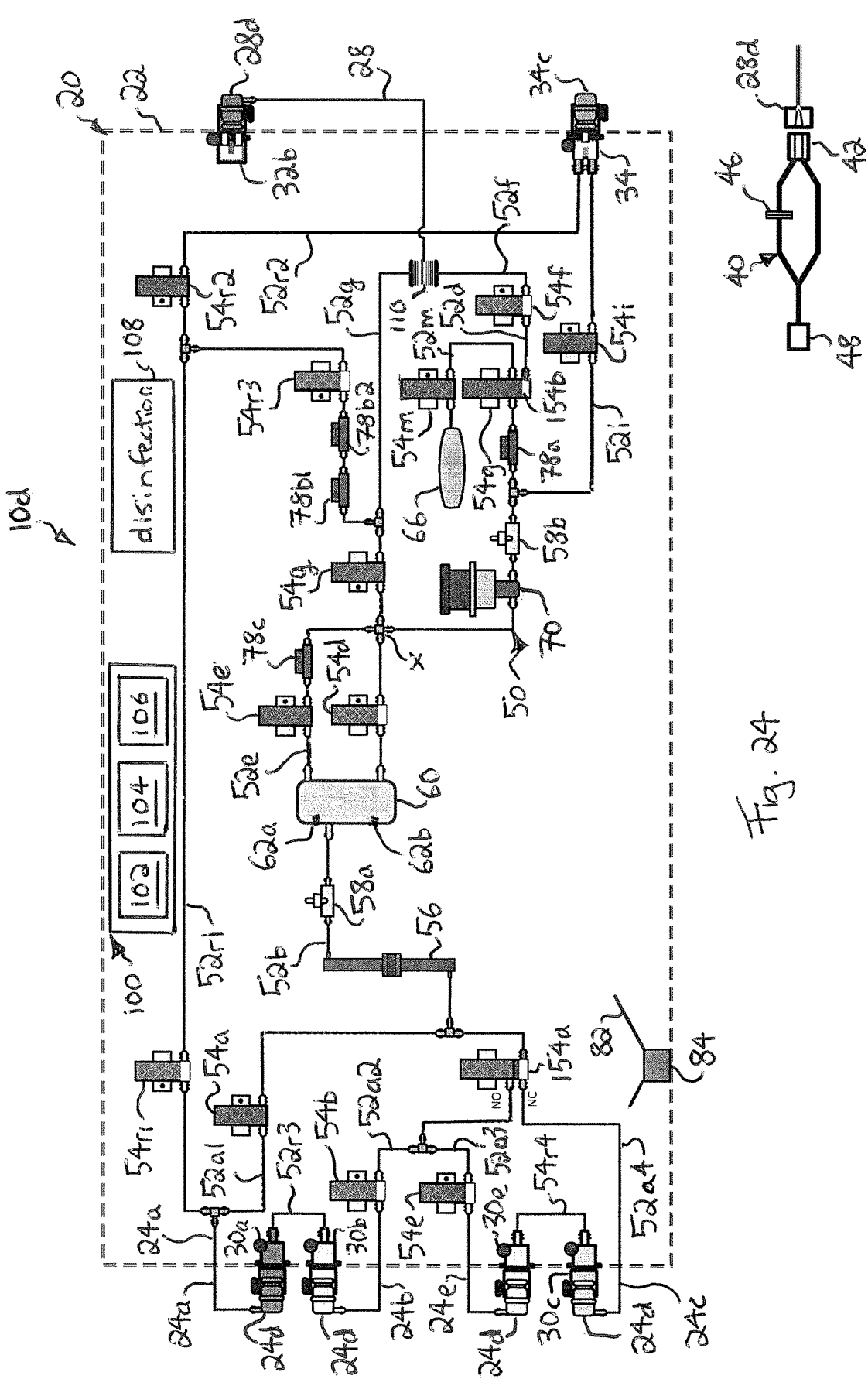
FIG. 24 is a schematic view illustrating an example disinfection sequence for the fourth primary embodiment of the APD cycler and associated system of the present disclosure.

Referring now to FIGS. 22 to 24, a further alternative APD system employing disinfection is illustrated by system 10d. System 10d includes many of the same components as systems 10a to 10c, which are generally numbered the same and include all structure, functionality and alternatives discussed above for those systems. For example, system 10d includes cycler 20 and control unit 100 having one or more processor 102, one or more memory 104, video controller 106 and user interface 108. System 10d includes inline dialysis fluid heater 56, reusable lines or tubes 52a and 52b, air trap 60 operating with respective upper and lower level sensors 62a and 62b, air trap valve 54d, vent valve 54e located along vent line 52e, reusable line or tubing 52c, dialysis fluid pump 70, temperature sensors 58a and 58b, reusable line or tubing 52d, pressure sensors 78a, 78b1, 78b2 and 78c, reusable patient tubing or lines 52f and 52g, hose reel 110, dual lumen reusable patient line 28, reusable drain tubing or line 52i extending to drain line connector 34 and having a drain line valve 54i, and reusable recirculation disinfection tubing or lines 52r1 and 52r2 operating with respective disinfection valves 54r1 and 54r2. A third recirculation or disinfection tubing or line 52r3 extends between disinfection connectors 30a and 30b for use during disinfection. A fourth recirculation or disinfection tubing or line 52r4 extends between disinfection connectors 30a and 30b for use during disinfection.

System 10d does not illustrate but may still provide a conductivity sensor 74 outputting to control unit 100 for any of the reasons or uses discussed herein. Each of pump 70, heater 56, the valves and sensors is controlled by and/or outputs to control unit 100.

One primary difference with system 10d is that the system includes PD fluid containers or bags 38a to 38c (e.g., holding the same or different formulations of PD fluid), which connect to distal ends 24d of reusable PD fluid lines 24a to 24c, respectively. System 10d further includes a fourth PD fluid container or bag 38e that connects to a distal end 24d of reusable PD fluid lines 24e. Fourth PD fluid container or bag 38e may hold the same or different type of PD fluid as PD fluid containers or bags 38a to 38c. Reusable PD fluid lines 24a to 24c and 24e extend in one embodiment from apertures 26 defined or provided by housing 22 of cycler 20 (see FIG. 1).

System 10d accordingly includes four disinfection connectors 30a to 30c and 30e for connecting to distal ends 24d of reusable PD fluid lines 24a to 24c and 24e, respectively, during disinfection. System 10d also employs patient line connector 32b discussed in connection with systems 10b and 10c, which includes an internal lumen, e.g., a U-shaped lumen, which directs fresh or used dialysis fluid from one PD fluid lumen 28a or 28b of dual lumen reusable patient line 28 into the other PD fluid lumen 28b or 28a. System 10d further includes reusable supply tubing or lines 52a1 to 52a4, which communicate with reusable supply lines 24a to 24c and 24e and operate with valves 54a to 54c and 54e, respectively, to allow PD fluid from a desired PD fluid container or bag 38a to 38c into cycler 20. Three-way valve 154a in the illustrated embodiment allows for control unit 100 to select between (i) 2.27% glucose dialysis fluid from container or bag 38b or 38e and (ii) icodextrin from container or bag 38c. In the illustrated embodiment, icodextrin from container or bag 38c is connected to the normally closed port of three-way valve 154a.

FIGS. 22 to 24 also illustrate that system 10d includes and uses disposable filter set 40, which communicates fluidly with fresh PD fluid lumen 28a and used PD fluid lumen 28b of dual lumen reusable patient line 28. Disposable filter set 40 includes a disposable connector 42 that connects to distal end 28d of reusable patient line 28. Disposable filter set 40 includes a connector 48 that connects to the patient's transfer set. Disposable filter set 40 further includes a sterilizing grade filter membrane 46 that further filters fresh PD fluid.

System 10*d*, like system 10*c*, is constructed such that drain line 52*i* during filling is fluidly connected downstream from dialysis fluid pump 70. In this manner, if drain valve 54*i* fails or somehow leaks during a patient fill, fresh PD fluid is pushed down disposable drain line 36 instead of used PD fluid potentially being pulled into pump 70 as in systems 10*a* and 10*b*.

System 10*d* includes many of the additions and advantages described above with system 10*c*, including all structure, functionality and alternatives described for such additions and advantages. For example, system 10*d* includes leak detection pan 82 located at the bottom of housing 22 of cycler 20 and a corresponding leak detection sensor 84 outputting to control unit 100. In another example, system 10*d* may be provided with an additional pressure sensor 78*c* located upstream of dialysis fluid pump 70. Again, measuring the suction pressure of pump 70 may help control unit 100 to more accurately determine pump volume. Additional pressure sensor 78*c* in the illustrated embodiment is located along vent line 52*e*, which may be filled with air or a mixture of air and PD fluid, but which should nevertheless be at the same negative pressure as PD fluid located within PD fluid line 52*c*. In a further example, system 10*d* includes redundant pressure sensors 78*b*1 and 78*b*2, the output of one of which is used for pump control as discussed herein, while the output of the other pressure sensor is a safety or watchdog output to make sure the control pressure sensor is reading accurately. In still a further example, system 10*d* may employ one or more cross, marked via an X in FIGS. 22 to 24, which may (i) reduce the overall amount and volume of the internal, reusable tubing, (ii) reduce the number of valves needed, and (iii) allow the portion of the fluid circuitry shared by both fresh and used PD fluid to be minimized.

Another difference with system 10*d* is that the system includes a source of acid, such as a citric acid container or bag 66. Citric acid container or bag 66 is in selective fluid communication with second three-way valve 154*b* via a citric acid valve 54*m* located along a citric acid line 52*m*. Citric acid line 52*m* is connected in one embodiment to the normally closed port of second three-way valve 154*b*, so as to provide redundant valves between citric acid container or bag 66 and the PD fluid circuit during treatment. The redundant valves ensure that no citric (or other) acid reaches the treatment fluid lines during treatment. Citric (or other) acid is instead used during disinfection. In an embodiment, control unit 100 commends inherently accurate pump 70 to operate in reverse with citric acid valve 54*m* open and second three-way valve 154*b* energized to open its normally closed port and close its normally open port. Inherently accurate pump 70 meters a desired amount of citric (or other) acid into disinfection circuit 50.

FIG. 22 illustrates one embodiment for a patient fill using system 10*d*. FIG. 22 illustrates the patient fill coming from PD fluid container or bag 38*a* (see arrows), wherein control unit 100 causes supply valve 54*a* to open, however, the patient fill may be supplied from any container or bag 38*a* to 38*c* or 38*e*. To use PD fluid container or bag 38*b*, control unit 100 instead causes supply valve 54*b* to be opened and first three-way valve 154*a* to be unenergized so that its normally open port remains open. To use PD fluid container or bag 38*c* (e.g., holding icodextrin), control unit 100 instead causes first three-way valve 154*a* to be energized so that its normally open port closes and its normally closed port opens. To use PD fluid container or bag 38*e*, control unit 100 instead causes supply valve 54*e* to be opened and first three-way valve 154*a* to be unenergized so that its normally open port remains open. During filling, control unit 100 causes all other valves, including recirculation or disinfection valves 54*r*1 and 54*r*2, vent valve 54*e*, patient draining valve 54*g*, and drain valve 54*i* to be closed.

During the patient fill of FIG. 22, control unit 100 also causes inline heater 56 to heat fresh PD fluid to body or other desired temperature using feedback from at least temperature sensor 58*a* as discussed herein. Control unit 100 also causes dialysis fluid pump 70, e.g., an inherently volumetrically accurate piston pump, to meter a precise amount of fresh PD fluid through PD fluid lines 52*b*, 52*c*, 52*d*, fresh PD patient line 52*f*, fresh PD lumen 28*a* of dual lumen patient line 28, and disposable filter set 40 to patient P (see arrows). Pumping pressure is controlled to a safe positive pressure at the machine via feedback from one or more pressure sensor 78*a*, 78*b*1 or 78*b*2 as discussed herein to one to five psig (e.g., two psig (14 kPa)). One or more pressure sensor 78*b*1 or 78*b*2 may be used to sense IPP via return lumen 28*b* as described above because pressure sensors 78*b*1 or 78*b*2 are located between valves 54*g*, 54*r*3 and patient P. Note that disposable filter set 40 shown unused in FIG. 24 is connected and in use for the patient filling of FIG. 22.

FIG. 23 illustrates one embodiment for a patient drain using system 10*d*. In FIG. 20, control unit 100 causes all supply valves 54*a*, 54*b* and 54*e*, vent valve 54*e*, patient filling valve 54*f*, and recirculation or disinfection valves 54*r*1 and 54*r*2 to be closed, and first and second three-way valves 154*a*, 154*b* to be unenergized. Control unit 100 causes patient draining valve 54*g* and drain valve 54*i* to open to allow PD fluid pump 70 to pump used dialysis fluid from patient P, through used PD lumen 28*b* of dual lumen patient line 28, reusable used PD line 52*g*, reusable PD fluid lines 52*c* and 52*d*, reusable drain line 52*i* and disposable drain line 36 to house drain or a drain container (see arrows). As discussed herein, the patient drain may end upon removing a precise amount of effluent and/or by sensing a characteristic increase in negative pressure signaling that patient P is or is almost empty.

Pumping pressure for the patient draining of FIG. 23 is controlled to a safe negative pressure at the machine via feedback from at least one pressure sensor 78*a*, 78*b*1, 78*b*2 or 78*c* as discussed herein to −1.0 psig to −3.0 psig (e.g., −1.3 psig (−9 kPa)). For sensing IPP using pressure sensor 78*a* via fill lumen 28*a* as described above, pressure sensor 78*a* can be moved so as to be located between patient filling valve 54*f* and hose reel 110, so that patient filling valve 54*f* can be closed during a patient drain, while allowing pressure sensor 78*a* to sense the pressure within patient P via fill lumen 28*a*. Note that disposable filter set 40 shown unused in FIG. 24 is connected and in use for the patient draining of FIG. 23. Also, as has been described herein, the patient drain (FIG. 23) may be performed before the patient fill (FIG. 13) if patient P begins treatment full of effluent from a previous treatment or an intermediate exchange.

FIG. 24 illustrates one embodiment for a disinfection sequence using system 10*d*. As illustrated, PD fluid containers or bags 38*a* to 38*c* and 38*e* are removed from reusable PD fluid lines 24*a* to 24*c* and 24*e*, respectively, after a final draining of the containers and a filling of the reusable cycler tubing or lines for disinfection (unless a different disinfection fluid is used). Distal ends 24*d* of reusable PD fluid lines 24*a* to 24*c* and 24*e* are connected respectively to disinfection connectors 30*a* to 30*c* and 30*e*. Disposable filter set 40 is removed from reusable patient line 28, which is then connected to patient line connector 32*b*. Disposable drain line 36 is removed from drain line connector 34, which is then sealed closed via a moveable, e.g., rotatable or slide-able, cover 34c. A disinfection circuit 50 is thus formed as illustrated in FIG. 24.

During disinfection, as with systems 10a to 10c, control unit 100 causes certain valves to remain open, while other valves are toggled during the disinfection sequence. First and second three-way valves 154a and 154b are likely toggled between unengerized and energized states. Control unit 100 may cause pump 70 to run in one direction or switch back and forth in two directions one or more time. During the disinfection sequence, control unit 100 causes heater 56 to heat the disinfection fluid (e.g., fresh PD fluid) to a disinfection temperature, e.g., 70° C. or greater. The disin-fection sequence lasts for a specified period of time to provide a proper disinfection dose A0.

Alternative Patient Line Filter Set

Figure 25:
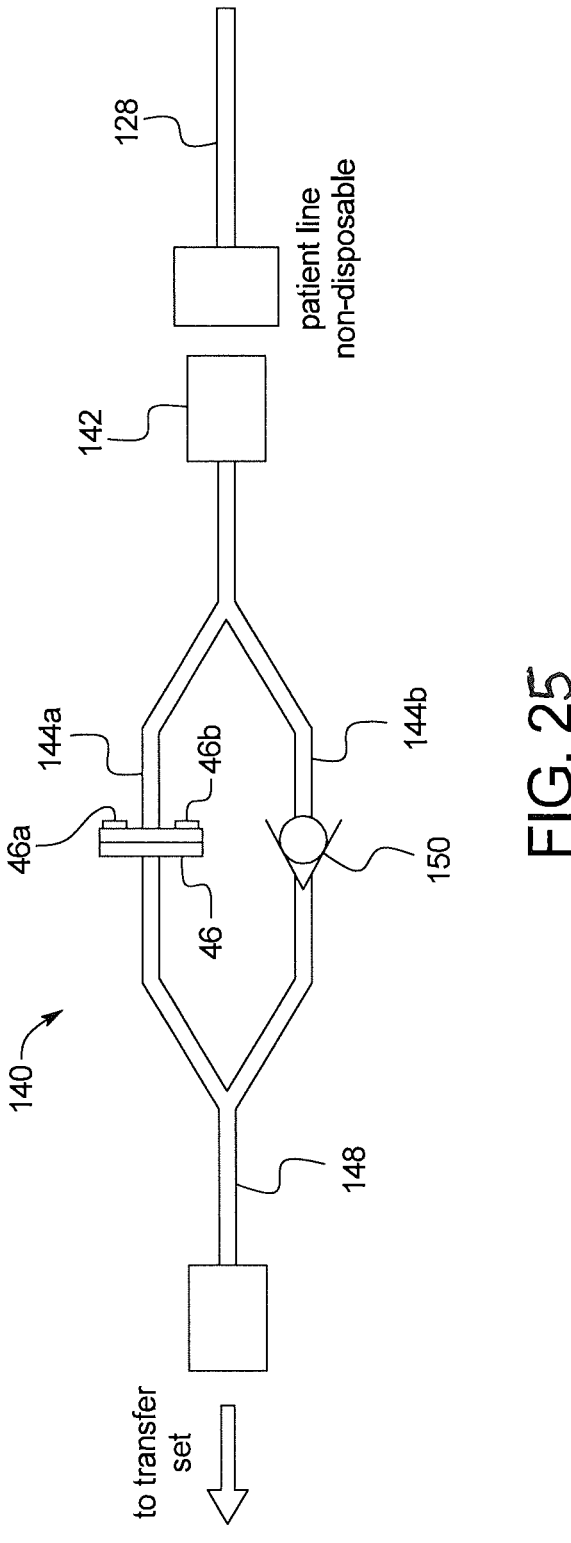
FIG. 25 is a schematic view illustrating an alternative embodiment of a disposable filter set for connection to a reusable patient line of the present disclosure.

Referring now to FIG. 25, an alternative disposable patient line filter set 140 useable with any of the systems discussed herein is disclosed (illustrated with system 210 next). Disposable patient line filter set 140 includes a connector 142 that connects to the distal end of an alterna-tive single lumen reusable patient line 128. Disposable patient line filter set 140 may be made, for example, of any of the polymer materials discussed herein. Disposable patient line filter set 140, like disposable patient line filter set 40, also includes (i) a first or fresh disposable line 144a that communicates with single lumen reusable patient line 128 and (ii) a second or used disposable line 144b that likewise communicates with single lumen reusable patient line 128. A sterilizing grade filter membrane 46, including all struc-ture, functionality and alternatives discussed above, is located in or along first or fresh disposable line 144a and provides a final stage of PD fluid filtration prior to PD fluid delivery to the patient. Fresh disposable line 144a and used disposable line 144b converge into a common line 148 that connects to a patient's transfer set.

A check valve or one-way valve 150 is located in used disposable line 144b. Check valve 150 is oriented so as to force fresh PD fluid being pumped to the patient to flow through sterilizing grade filter membrane 46 for final puri-fication and sterilization prior to delivery to the patient. The orientation of check valve or one-way valve 150 allows used PD fluid or effluent to be pulled under negative pressure through second or used disposable line 144b. In an embodi-ment, check valve or one-way valve 150 is structured such that the negative pressure needed to pull used PD fluid through valve 150 is less than the pressure needed to pull used PD fluid back through sterilizing grade filter membrane 46. Effluent taking the path of least resistance therefore flows mainly through check valve or one-way valve 150 along used disposable line 144b. Any effluent flowing through sterilizing grade filter membrane 46, however, is not harmful to the filter, which only needs to remain intact for the current treatment. Additionally, fibrin and other materials trapped on the patient side of sterilizing grade filter mem-brane 46 may be pushed back to the patient on the next fill, clearing the filter membrane 46.

Hose Reel

Figure 26:
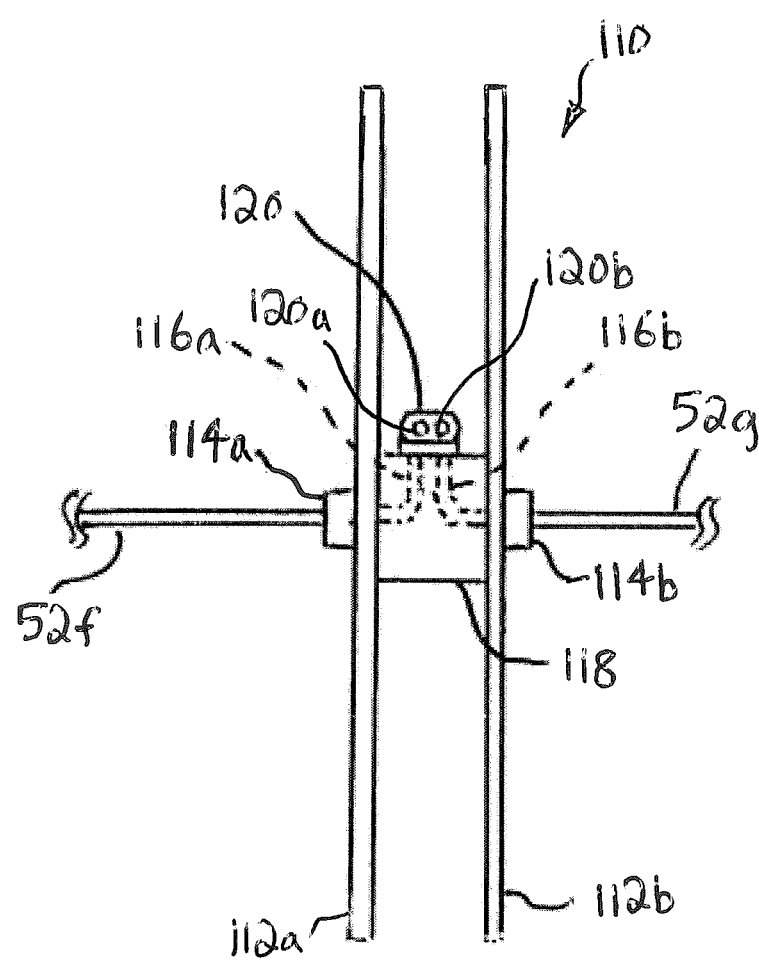
FIG. 26 is a schematic view illustrating one possible PD fluid flowpath for a reusable patient line hose reel of the present disclosure.

FIGS. 2, 5 to 24, 28, 29, 31 and 32 illustrate that any of the systems described herein may be provided with a spool or hose reel 110 located within housing 22 or 222 of APD cyclers 20 or 220, respectively. Spool or hose reel 110 is configured to automatically retract reusable patient line 28 or 128 when the patient line is connected to patient line connector 32a, 32b, 132 or is otherwise not connected to the patient. FIG. 26 schematically illustrates one embodiment for fluidically accommodating hose reel 110. Hose reel 110 may be made of any of the plastics, polymers and/or metals discussed herein. Any portion of hose reel 110 that contacts fresh or used PD fluid is made of a medically and physi-ologically safe material. In the illustrated embodiment, hose reel includes winding reels 112a, 112b between which reusable dual lumen patient line 28 or single lumen patient line 128 is unwound and rewound.

Rotating seals 114a, 114b extend from and may be formed with winding reels 112a, 112b, respectively. Rotating seal 114a seals rotatably to an end of fixed fresh PD fluid line 52f, e.g., via compressible gasket, such as an o-ring gasket made of a medically safe material, such as silicone rubber. Rotat-ing seal 114b seals rotatably to an end of fixed used PD fluid line 52g, e.g., via compressible gasket, such as an o-ring gasket made of a medically safe material. Rotating seals 114a, 114b allow hose reel 110 to rotate in a fluid-tight manner relative to fixed fresh and used PD fluid lines 52f, 52g located within housing 22 of cycler 20. In the illustrated embodiment, fixed fresh and used PD fluid lines 52f, 52g are shown extending to winding reels 112a, 112b, respectively, from opposite directions. In an alternative embodiment, fixed fresh and used PD fluid lines 52f, 52g extend to one of the winding reels 112a, 112b from the same direction. Here, rotating seal 114b may rotate sealingly about rotating seal 114a or vice versa.

In the illustrated embodiment, a rotating fresh fluid hose reel pathway 116a is formed within a rotating winding spool 118. Rotating fresh fluid hose reel pathway 116a commu-nicates fluidly with fixed fresh PD fluid line 52f. A rotating used fluid hose reel pathway 116b is formed within rotating winding spool 118. Rotating used fluid hose reel pathway 116b communicates fluidly with fixed used PD fluid line 52g. Winding reels 112a, 112b may be formed with or attached to rotating winding spool 118. Rotating fresh and used fluid hose reel pathways 116a, 116b illustrate that fresh and used PD fluid flows through hose reel 110 in each of systems 10a to 10d and 210 discussed herein. It should also be appreciated that rotating fresh and used fluid hose reel pathways 116a, 116b of hose reel 110 form part of the disinfection circuits discussed herein, such as disinfection circuits 50, 250.

A rotating connector 120 for connecting to dual lumen patient line 28 is formed with or attached to winding spool 118. One end of dual lumen patient line 28 is attached sealingly to rotating connector 120. Dual lumen patient line 28 accordingly extends from rotating connector 120. A fresh lumen 120a of rotating connector 120 communicates fluidly with fresh fluid hose reel pathway 116a and fresh PD fluid lumen 28a of dual lumen reusable patient line 28. A used lumen 120b of rotating connector 120 communicates fluidly with used fluid hose reel pathway 116b and used PD fluid lumen 28b of dual lumen reusable patient line 28. In an alternative embodiment using alternative single lumen patient line connector 132 and an alternative single lumen reusable patient line, fresh and used fluid hose reel pathways 116a, 116b tee fluidically together before extending to a single lumen provided by rotating connector 120.

Figure 27:
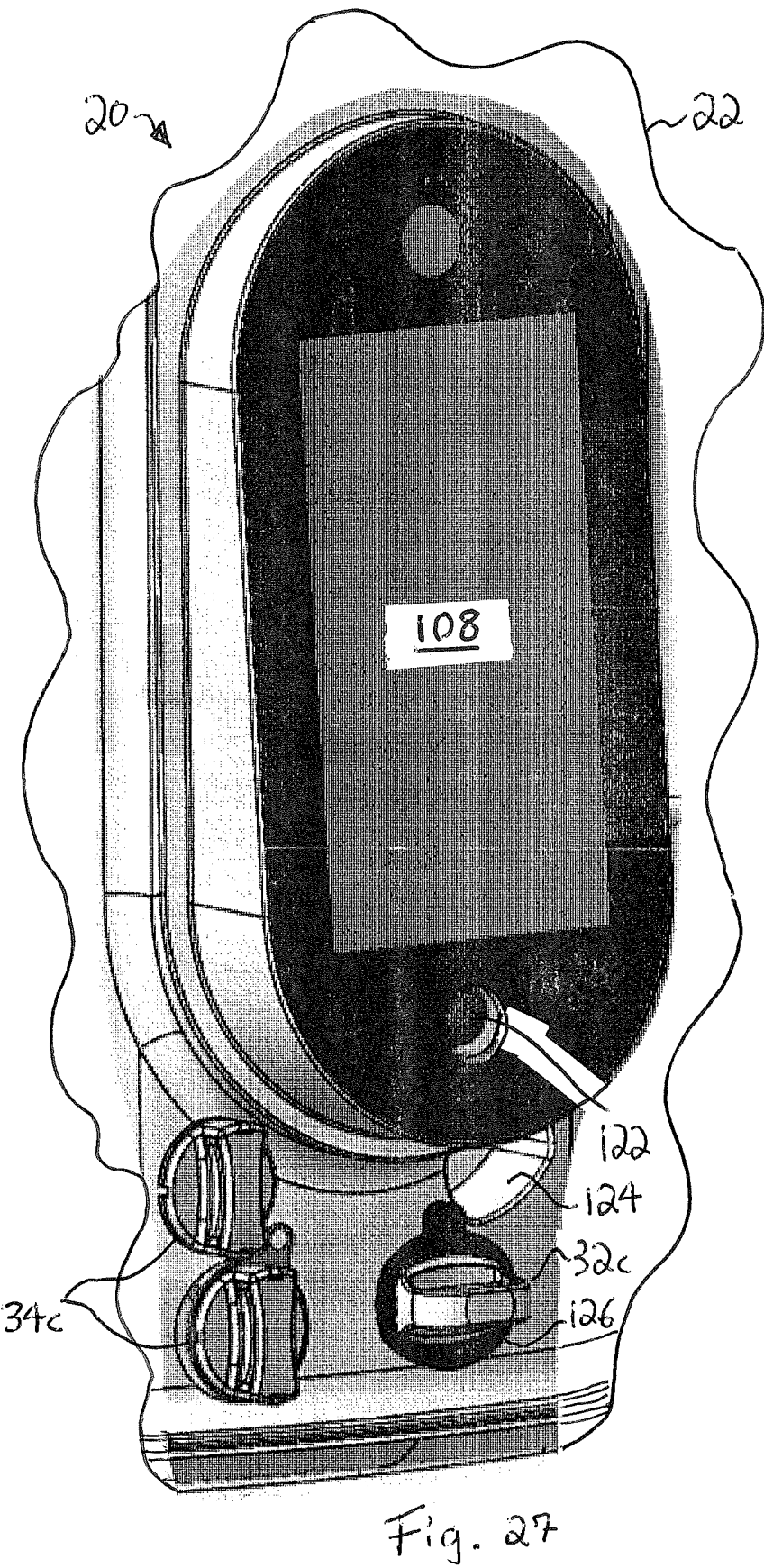
FIG. 27 is a sectioned perspective view illustrating one embodiment for a front of the APD cycler housing of the present disclosure showing the distal end of the reusable patient line pulled into the housing via the hose reel.

Referring now to FIG. 27, a portion of housing 22 of cycler for any of systems 10a to 10d and 210 discussed herein is illustrated. For reference, one embodiment for user interface 108 is illustrated. Also, moveable, e.g., rotatable or slideable, cover 34c of drain line connector 34 is illustrated in two positions, one position in which cover 34c is rotated up to allow disposable drain line 36 to be connected to drain line connector 34, and a second position in which cover 34c is rotated down to sealingly cap drain line connector 34 when disposable drain line 36 has been removed for disinfection.

FIG. 27 also illustrates a pressable actuator or button 122 that the patient or other user activates (e.g., presses) to allow a releasable lock to be lifted so that hose reel 110 can retract and coil reusable patient line 28 or 128 into housing 22. Until actuator or button 122 is activated (e.g., pressed), reusable patient line 28 or 128 remains uncoiled from spool or hose reel 110, so that the spool does not pull on the reusable patient line during treatment. In an embodiment, actuator or button 122 is a momentary button that the patient has to continuously press during the retraction and coiling of the patient line onto hose reel 110. If the patient or user stops pressing button 122, the retraction stops. Such configuration of pressable actuator button 122 has the added advantage that the patient or user may pull patient line 28 or 128 to any desired distance from housing 22, up to a maximum distance, wherein the patient line is held in place by the releasable lock at the desired distance.

FIG. 27 further illustrates an alternative patient line connector 32c. Patient line connectors 32a, 32b and 132 are each illustrated as being provided by or attached to housing 22 of cycler 20, wherein patient line 28 or 128 is connected to patient line connectors 32a, 32b and 132 from the outside of housing 22. Alternative patient line connector 32c is not provided by or attached to housing 22, and instead comes free from cycler 20 and patient line 28 or 128. Alternative patient line connector 32c when not needed (patient line 28 or 128 is connected to the patient) is stored within a cavity 124 provided by housing 22. When the patient has disconnected reusable patient line 28 or 128 from patient line filter set 40 or 140, respectively, and patient line connector 32c is needed for disinfection, the patient pulls patient line connector 32c from cavity 124 and connects connector 32c to the end of reusable patient line 28 or 128. The patient then presses and holds actuator or button 122 to enable hose reel 110 to automatically retract and coil patient line 28 or 128, such that patient line connector 32c is pulled into docking port 126 and the coiling is completed.

In the case of dual lumen patient line 28, patient line connector 32c includes or defines an internal lumen, e.g., a U-shaped or 180° lumen, which directs fresh or used dialysis fluid from one PD fluid lumen 28a or 28b of dual lumen reusable patient line 28 into the other PD fluid lumen 28b or 28a. During disinfection, the disinfection fluid, e.g., heated fresh PD fluid, may flow up one lumen 28a or 28b of dual lumen reusable patient line 28, through patient line connector 32c, and down the other lumen of dual lumen reusable patient line 28.

Spool or hose reel 110 is useful during heat disinfection because the heated disinfection fluid (PD fluid, water or other) within coiled patient line 28 or 128 retains heat due to being coiled (reducing surface area exposed to ambient) and for the coils being located within a housing 22 or 222. If it is determined that retaining coiled patient line 28 or 128 on spool or hose reel 110 within housing 22 or 222 causes the housing to be too big or cumbersome, spool or hose reel 110 may instead be provided separate from housing 22 or 222. Here, separate spool or housing 22 or 222 having coiled patient line 28 or 128 may be provided within a separate cover or enclosure that helps the heated disinfection fluid to retain heat.

Water Disinfection with Water Cleaning

Figure 28:
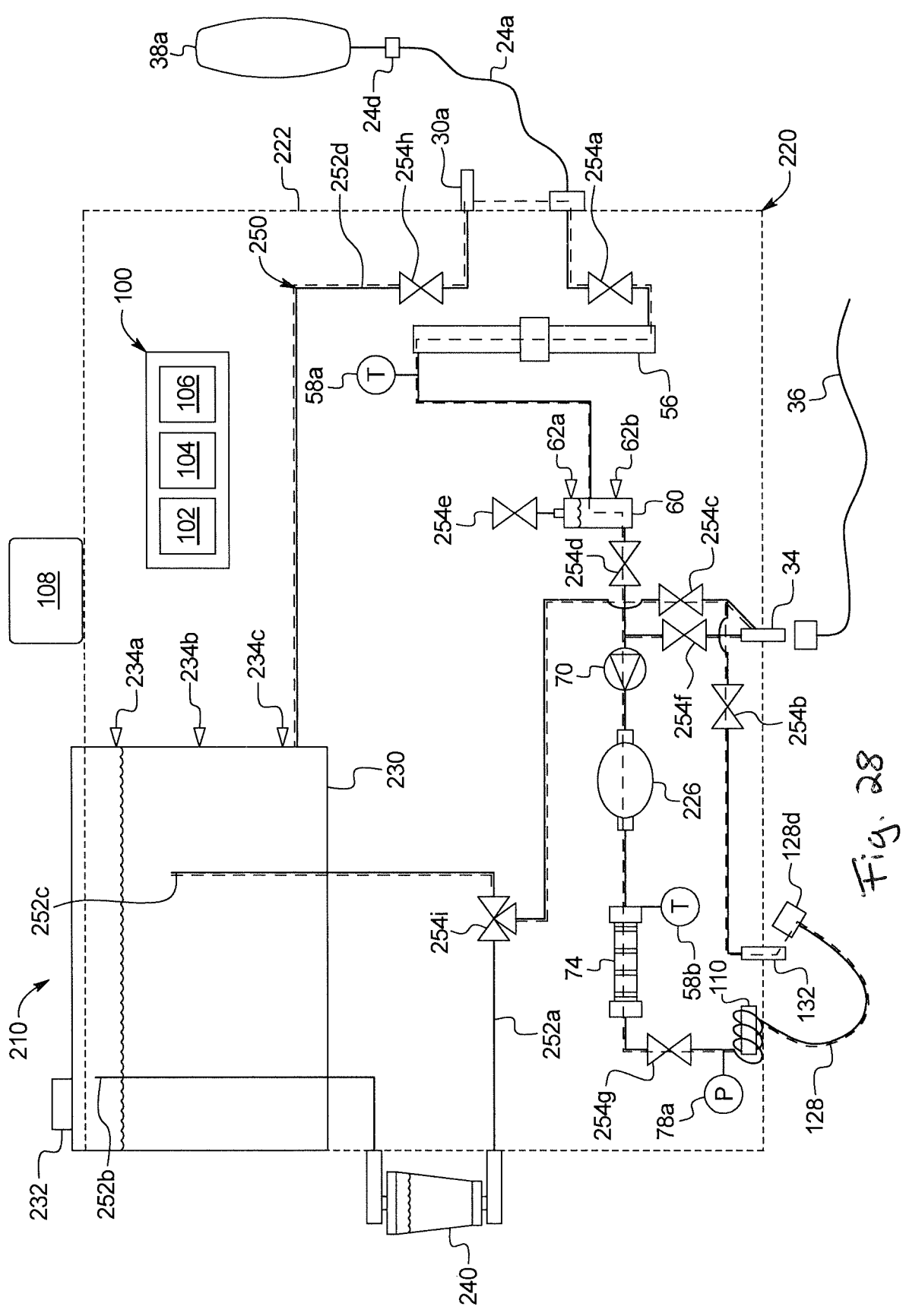
FIGS. 28 and 29 are schematic views of an alternative APD cycler and system of the present disclosure using water (or other disinfection fluid) for disinfection, wherein the disinfection water is cleaned for a subsequent disinfection.
Figure 29:
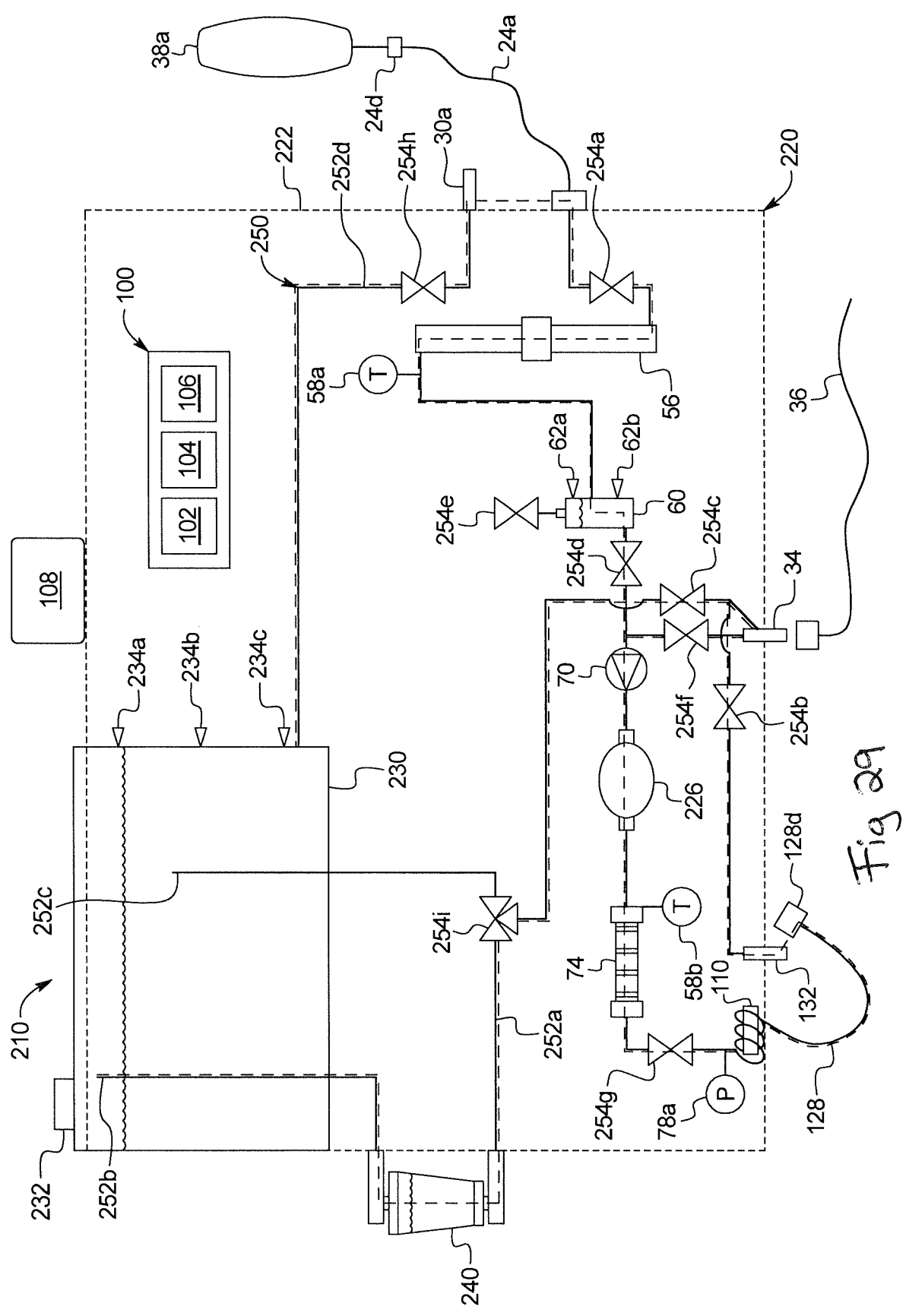

FIGS. 28 and 29 illustrate an alternative disinfection system 210, which uses water for disinfection. System 210 includes many of the same components as systems 10a to 10d, wherein like components are numbered the same and include all of the materials, structure, functionality and alternatives discussed in connection with systems 10a to 10d. In particular, and moving generally from right to left, system 210, like systems 10a and 10b, includes one or more PD fluid container or bag 38a to 38c, here PD fluid container or bag 38a is connected to distal end 24d of reusable PD fluid line 24a, wherein PD fluid line 24a connects releasably to disinfection connector 30a during the disinfection and water cleaning sequences discussed below. PD fluid container or bag 38a to 38c may contain different types and formulations of fresh PD fluid as described above.

Disinfection connector 30a, drain line connector 34 (which may be releasably covered by moveable, e.g., rotatable or slideable, cover 34c) and alternative single lumen patient line connector 132 extend from a housing 222 of cycler 220 of system 210. Housing houses dialysis fluid inline heater 56, which may be a resistive heater having a reusable heater body that accepts PD fluid for treatment heating and water for disinfection heating. Temperature sensor 58a provides temperature feedback for controlling dialysis fluid inline heater 56 as discussed above. Air trap 60 operating with upper and lower level sensors 62a and 62b is located downstream from dialysis fluid inline heater 56.

System 210 also includes dialysis fluid pump 70 having a reusable pump body that accepts fresh and used PD fluid and water for pumping. Dialysis fluid pump 70 is inherently accurate and may be a piston, membrane, gear pump (gear pump may be better suited here for operation with flowmeter 226) or centrifugal pump. System 210 additionally provides a flowmeter 226 (which may also be provided in systems 10a to 10d) to generate flowrate outputs for treatment, the disinfection sequence and the water cleaning sequence. Conductivity sensor 74 having temperature compensation via temperature sensor 58b is likewise provided for any of the purposes discussed above. Pressure sensor 78a is provided for outputting to control fresh and used PD fluid patient pressures and the disinfection and water cleaning sequence pressures.

In the illustrated embodiment, single lumen reusable patient line 128 is provided and operates with alternative disposable patient line filter set 140 discussed in connection with FIG. 25. Single lumen reusable patient line 128 includes a distal end 128d that plugs releasably into alternative single lumen patient line connector 132 when not used for treatment, e.g., during the disinfection and water cleaning sequences.

System 210 also includes a plurality of two-way fluid valves 254a to 254h, which are electrically actuated valves having a reusable valve body that occludes (e.g., when unpowered for fail safe operation) or allows (e.g., when powered) PD fluid or water to flow through the body. Three-way valve 254i is also provided. The valves include a PD fluid line valve 254a, disinfection line valves 254b and 254c, air trap valve 254d, vent valve 254e, drain line valve 254f, patient line valve 254g and water cleaning valves 254h and 254i (e.g., three-way). PD fluid line valve 254a allows fresh PD fluid to be pumped to the patient. During disinfection, distal end 24d of reusable PD fluid line 24a is connected to disinfection connector 30a, which allows disinfection water to circulate into the PD fluid line upstream of inline heater 56. Disinfection line valves 254b and 254c allow water to circulate for disinfection and water cleaning when opened. Air trap valve 254d allows air trap 60 to be filled when closed and fresh PD fluid to flow for treatment when opened. Vent valve 254e is opened when air trap 60 is filled or drained. Drain valve 254*f* is opened when the patient is drained. Water cleaning valve 254*h* either isolates water tank 230 or allows water to be recirculated for disinfection. Three-way water tank valve 254*i* in the illustrated arrangement is either in (i) an orientation in which cleaning cartridge 240 is isolated (FIG. 28) or (ii) an orientation in which cleaning cartridge 240 is made part of the active fluid circuit (FIG. 29).

Cycler 220 of system 210 includes a user interface 108 including all structure, functionality and alternatives discussed above, which is under control of video controller 106 of control unit 100. Control unit 100 includes one or more processor 102 and one or more memory 104 that receive, store and process signals or outputs from the pressure sensor 78*a*, temperature sensors 58*a* and 58*b* and conductivity sensor 74. Control unit 100 uses pressure feedback to control dialysis fluid pump 70 to pump fresh and used PD fluid at safe patient pressure limits for treatment and system limits for disinfection and water cleaning. Control unit 100 uses temperature feedback to control inline dialysis fluid heater 56 to heat the fresh dialysis fluid to, e.g., body temperature and disinfection water, e.g., reverse osmosis ("RO") water, to a disinfection temperature, e.g., 70° C. or greater. Control unit 100 uses temperature compensated conductivity readings to analyze fresh and/or used dialysis fluid for the reasons discussed herein.

As illustrated in detail below, control unit 100 also opens and closes dialysis fluid valves 254*a* to 254*i* in combination with the operation of dialysis fluid pump and heater 56 to run a priming sequence (e.g., using fresh PD fluid), a patient fill sequence (using fresh PD fluid), a patient drain sequence (used PD fluid or effluent), a disinfection sequence (using water or other disinfection fluid held within tank 30 such as a citric acid solution) after a PD treatment and a water cleaning sequence (using water) after the disinfection sequence.

Cycler 220 of system 210 provides a water tank 230 that holds a desired quantity of water (or other disinfection fluid), e.g., two to four liters, or enough to fully fill, or at least adequately fill, a disinfection and water cleaning circuit 250, which includes each of the lines associated with each of fluid valves 254*a* to 254*i*, reusable PD fluid line 24*a* and reusable patient line 128. Water tank 230 may be made, for example, of any of the materials discussed herein and includes a removable and resealable cap 232, which may be accessed from outside of housing 222, to fill water tank 230 when needed.

Level sensors 234*a*, 234*b* and 234*c* are provided to sense high, medium and low levels, respectively, within water tank 230. Any or all level sensors 62*a*, 62*b*, 234*a*, 234*b* and 234*c* may be noninvasive ultrasonic, inductive, capacitive and/or optical sensors that detect when water (or other disinfection fluid) is present or not present at the particular level at which they are set relative to air trap 60 or water tank 230. Level sensors 234*a*, 234*b* and 234*c* output to control unit 100 and may be used to confirm that a desired level of water resides within tank during treatment (e.g., water should be at high level sensor), during disinfection (e.g., water should be at medium level sensor) and during water cleaning (e.g., water should be at low level sensor).

FIGS. 28 and 29 also illustrate that a cleaning cartridge 240 is spliced in between a sorbent line or tube 252*a*, leading to three-way water cleaning valve 254*i*, and sorbent line or tube 252*b*, leading to water tank 230. Cleaning cartridge 240 is also illustrated in FIG. 1 showing that it may be slid conveniently into a slot 224 of housing 222 of cycler 220. In FIG. 1, sliding cleaning cartridge 240 into slot 224 makes a first sealed fluid communication with sorbent line or tube 252*a* and a second sealed fluid communication with sorbent line or tube 252*b*. Cleaning cartridge 240 may be a sorbent cartridge that holds activated carbon, for example. Disinfection lines or tubes 252*c* and 252*d* are placed in sealed fluid communication with water tank 230. In an embodiment, control unit 100 monitors the service hours or number of treatments that cleaning cartridge 240 has performed and prompts the patient or caregiver via user interface 108 to replace cleaning cartridge 240 after a predetermined number of service hours or treatments. As discussed herein, control unit 100 may also include a transceiver (not illustrated) and a wired or wireless connection to a network, e.g., the internet, for sending treatment data, such as service hours or number of treatments for cleaning cartridge 240, to and receiving prescription or other instructions, such as a notice to replace cleaning cartridge 240, from a doctor's or clinician's server interfacing with a doctor's or clinician's computer.

Control unit 100 runs a priming sequence in an embodiment by pulling fresh PD fluid from PD fluid container or bag 38*a* via dialysis fluid pump 70 and pushing the fluid through reusable patient line 128 and disposable drain line 36 to house drain or a drain container. Control unit 100 runs an initial drain sequence by pulling used PD fluid or effluent from the patient, through disposable patient line filter set 140 and reusable patient line 128 via dialysis fluid pump 70 and pushing the used PD fluid to house drain or a drain container. Control unit 100 runs a patient fill sequence in an embodiment by pulling fresh PD fluid from PD fluid container or bag 38*a* via dialysis fluid pump 70 and pushing the fresh PD fluid to the patient via reusable patient line 128, disposable patient line filter set 140 and the patient's transfer set. The drain and fill sequences are repeated until treatment has been completed.

After treatment, it is contemplated (although not required) to first drain as much used PD fluid as possible to house drain or a drain container via drain line 36. Here, control unit 100 causes vent valve 254*e* to open to allow air into the PD fluid circuit, and causes dialysis fluid pump 70 to run in the normal treatment direction, pulling used PD fluid from chamber 60 and the intervening PD lines past the pump, further passing the fluid through valve 254*b* and drain port 34 to drain via drain line 36. Valves 254*f* and 254*c* are closed during this phase. Draining as much of the used PD fluid as possible may allow the disinfection water to last longer, and it is therefore contemplated to add an additional three-way valve (not illustrated) between valves 254*a* and 254*h* that can be toggled by control unit 100 to either allow fresh dialysis fluid in through reusable PD fluid line 24*a* for treatment or air in through disinfection connector 30*a* to backfill the PD fluid drained before treatment. Pulling air from disinfection connector 30*a* enables more of the PD circuit to be drained.

After any of the PD fluid draining embodiments, distal end 128*d* of reusable patient line 128 is next connected to single lumen patient line connector 132, disposable drain line 36 is discarded and rotatable or slideable cover 34*c* seals drain line connector 34 closed, and distal end 24*d* of reusable PD fluid line 24*a* is connected to disinfection connector 30*a* (repeated for any additional reusable PD fluid lines 24*b*, 24*c*, etc.). Control unit 100 then opens all fluid valves except vent valve 254*e* (or closes or toggles open and closed certain valves, e.g., any one or more of PD fluid line valves 54*a* to 54*c*) and sets three-way valve 254*i* in FIG. 28 so that cleaning cartridge 240 is isolated but disinfection lines or tubes 252*c* and 252*d* are open to form disinfection circuit 250. Dialysis fluid pump 70 then circulates water from water tank 230 around disinfection circuit 250, while heater 56 heats the water, e.g., to at least 70° C. Dialysis fluid pump 70 may pump heated water in forward and reverse directions, and/or the heated water may include slugs of entrained air to increase turbulence and enhance disinfection. The disinfection sequence is performed for a predetermined period of time in one embodiment.

In one embodiment, control unit 100 drains the disinfection water or other disinfection fluid as a first step in a next treatment, e.g., when a new drain line 36 is connected to drain line connector 34. FIG. 29 illustrates an alternative embodiment wherein instead of draining the water just used for disinfection, which may contain fats, proteins, fibrin, etc., removed from the inner walls of disinfection circuit 250, control unit 100 transitions instead to a water cleaning sequence in which three-way valve 254*i* in FIG. 29 is changed so that disinfection line or tube 252*c* is closed and cleaning cartridge 240 and sorbent lines or tubes 252*a* and 252*b* are brought into fluid communication with water cleaning circuit 250, which also includes disinfection line 252*d*. With all other valves open except vent valve 254*e*, dialysis fluid pump 70 circulates water from water tank 230 around water cleaning circuit 250, which includes cleaning cartridge 240 configured to clean the water. Dialysis fluid heater 56 may or may not be energized. The water treatment is performed for a predetermined period of time in one embodiment. When water cleaning is complete, control unit 100 causes dialysis fluid pump 70 to pump as much water as possible back to water tank 230, where it is stored for the disinfection of cycler 20 after the next treatment. To this end, vent valve 254*e* may be opened during the water return to backfill the lines with air that has been filtered via a hydrophobic filter provided with vent valve 254*e*.

Figure 31:
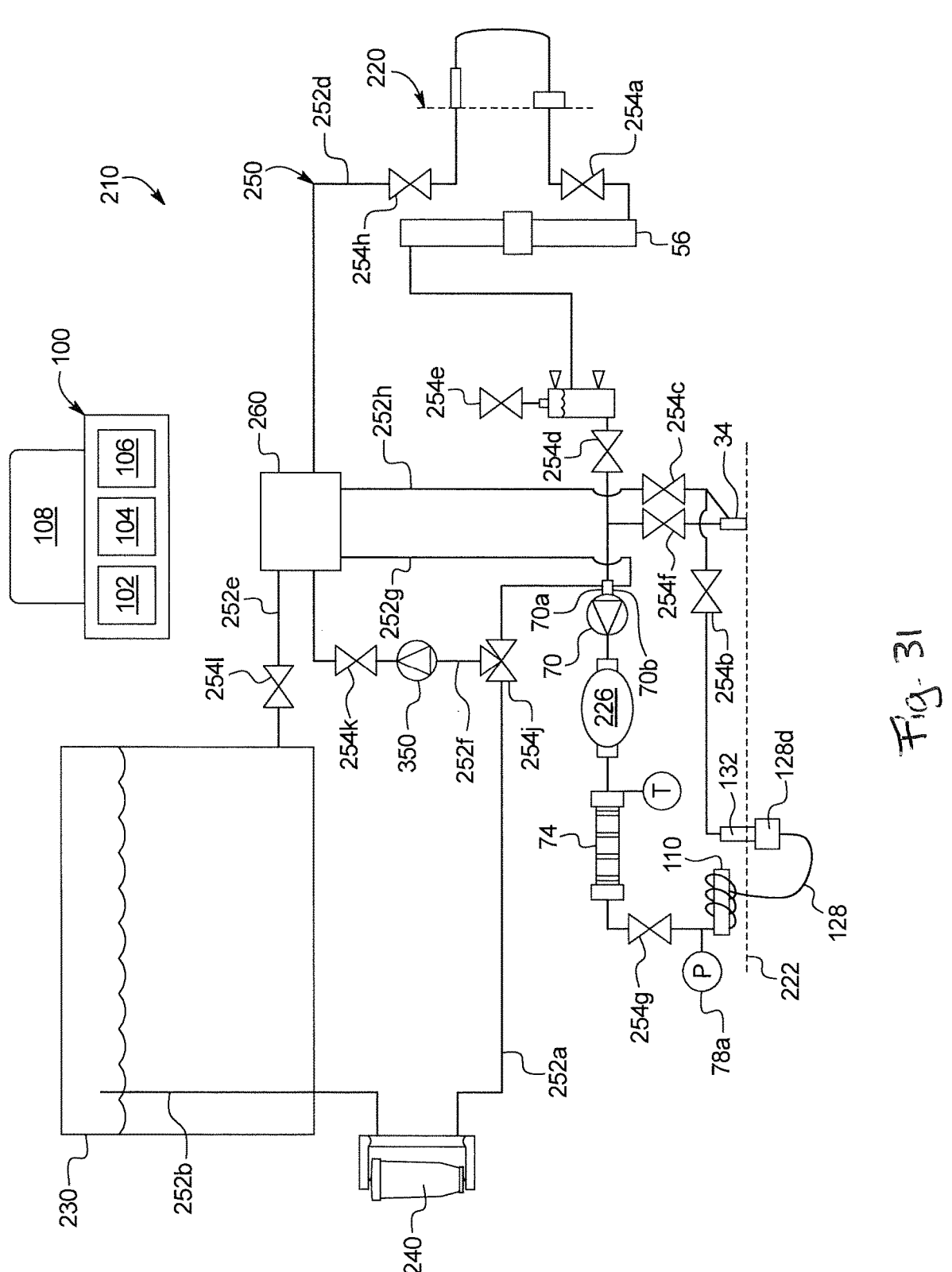
Figure 30:
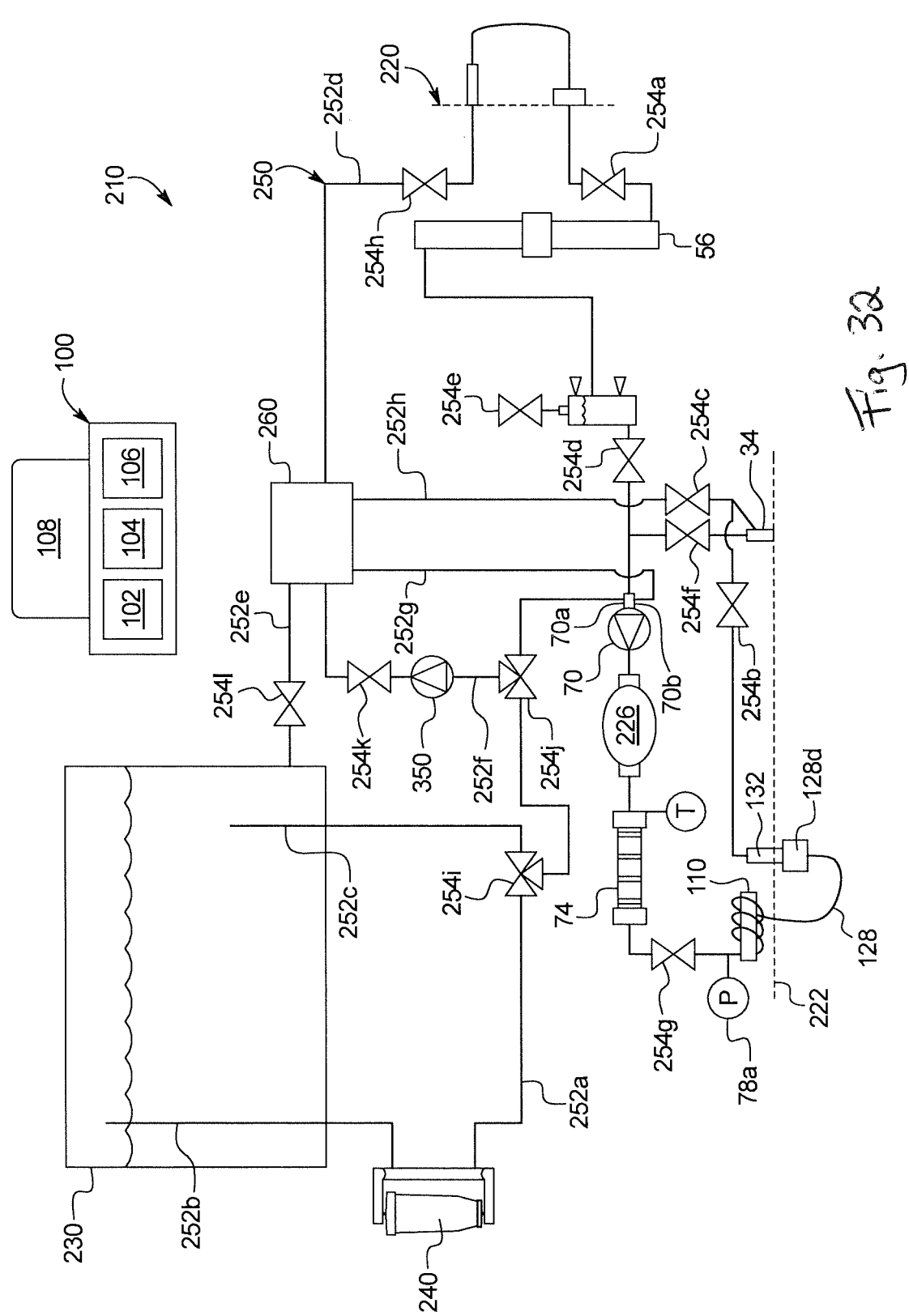

As illustrated in FIGS. 31 and 32, it is contemplated in FIGS. 28 and 29 to add an extra pump 350 under control of control unit 100, which is positioned and arranged (e.g., along lines 252*a* or 252*c* in FIGS. 28 and 29, wherein three-way valve 254*i* is reoriented to allow recirculation) to independently circulate water from water tank 230 to cleaning cartridge 240 and back to water tank 230. In such pumping, no other portion of the PD fluid path is influenced. The disinfection water or other disinfection fluid in the PD fluid path after use is then either emptied to drain or delivered back up to water tank 230 prior to the next treatment. If delivered back to water tank 230, such water is cleaned in the next water cleaning cycle using cleaning cartridge 240 and the additional pump under control of the control unit. In any case, the addition of a dedicated cleaning pump 350 prevents bacteria removed in cleaning cartridge 240 from potentially reaching fresh PD fluid elsewhere in the cycler circuit.

Citric Acid Disinfection

It is contemplated to periodically run a citric acid disinfection sequence for any of systems 10*a*, 10*b*, 10*c*, 10*d* and 210. Here, citric acid container or bag 66 may be connected to any reusable fluid line 24*a* to 24*c*, 24*e* or to the location illustrated in connection with system 10*d* of FIGS. 22 to 24. Control unit 100 may use the output of a conductivity sensor, such as conductivity sensor 74, to confirm that citric acid is indeed present and to only allow dialysis fluid pump 70 to operate when reusable patient line 28 or 128 is plugged into patient line connector 32*a*, 32*b* or 132, or is plugged by patient line connector 32*c*, as sensed as described herein. The citric acid disinfection sequence helps to remove and hinder the growth of biofilm and to remove endotoxin residuals. Citric acid may also help to remove calcium carbonate, which may be a problem if using certain PD fluids containing both bicarbonate and calcium.

Pump Flush Flow

Figure 30:
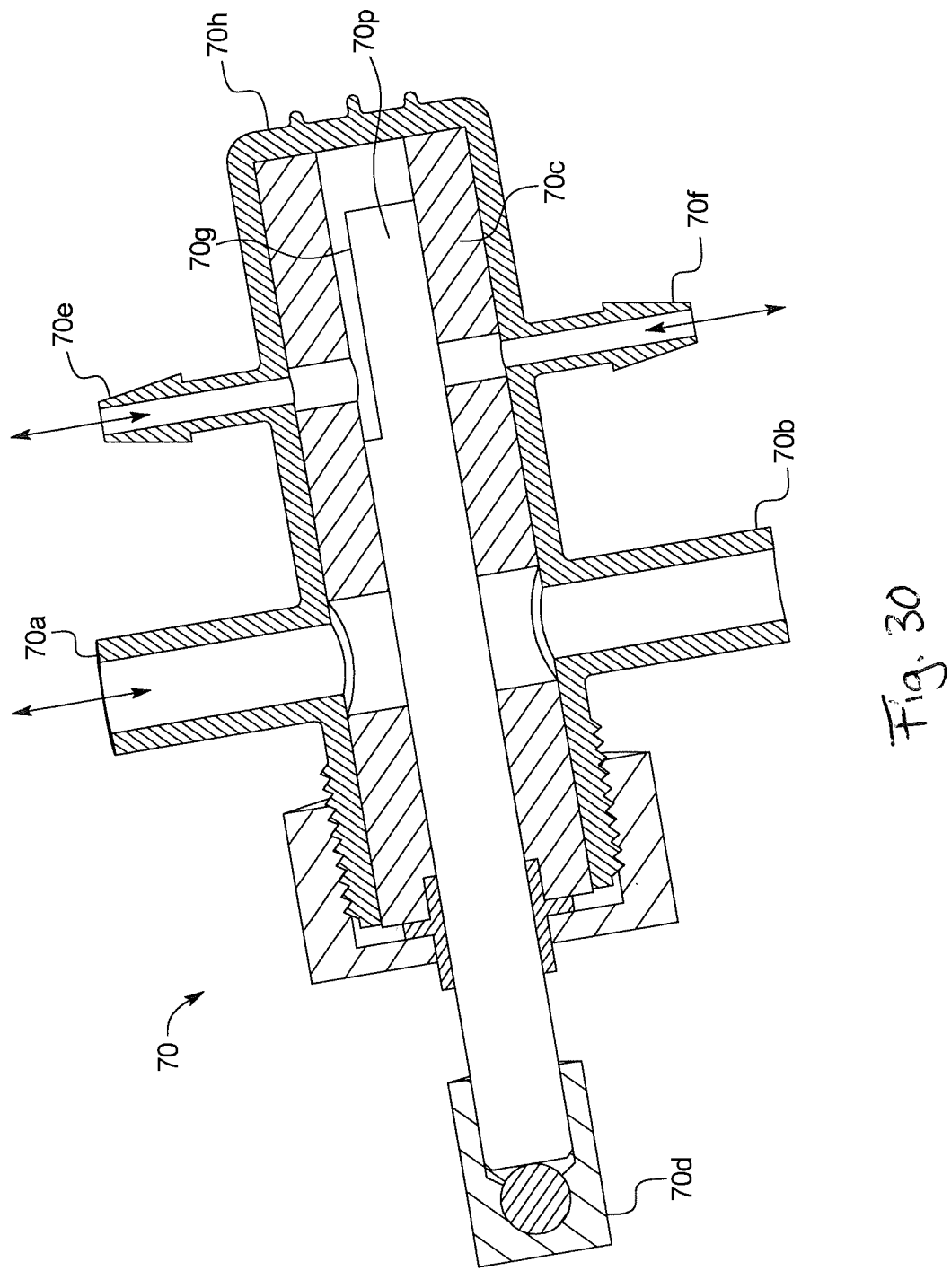
FIG. 30 is a sectioned elevation view of one embodiment of a piston pump configured to receive a flush flow, the piston pump useable with any of the systems described herein.

As discussed above, dialysis fluid pump 70 is of a type that is inherently accurate so that a separate PD fluid volume measurement apparatus, such as a balance chamber or an apparatus using the ideal gas law, is not needed. Likewise, flow sensors, such as a differential flow sensors, are not needed. As illustrated in FIG. 30, dialysis fluid pump 70 is in one embodiment an electrically operated piston pump. Piston pump 70 includes a housing 70*h* holding a cylinder 70*c* within which a piston 70*p* is actuated via a motor (not illustrated), under control of control unit 100, driving a motion coupler 70*d* coupled to piston 70*p*, wherein motion coupler 70*d* converts a rotational motion of the motor to a rotational and translational movement of piston 70*p*. Housing 70*h* includes PD fluid inlet/outlet ports 70*e* and 70*f* (bidirectional) and flush flow ports 70*a* and 70*b* (bidirectional or stagnant).

Motion coupler 70*d* moves piston 70*p* in and out relative to cylinder 70*c* to create positive and negative pumping pressure, respectively. Motion coupler 70*d* also rotates piston 70*p* within cylinder 70*c* to move fluid from one of ports 70*e* and 70*f* acting as a PD fluid inlet port to the other of ports 70*e* and 70*f* acting as a PD fluid outlet port. The distal end of piston 70*p* includes a cutout or groove 70*g* forming a flat. The open area formed by groove 70*g* accepts PD fluid at the inlet port 70*e* or 70*f* (under negative pressure when piston 70*p* is retracted within cylinder 70*c*) and is then rotated to deliver PD fluid at the outlet port 70*e* or 70*f* (under positive pressure when piston 70*p* is extended within cylinder 70*c*). Groove 70*g* provides the valve functionality for dialysis fluid pump 70 to have different flow directions.

The translational and rotational movement of piston 70*p* within cylinder 70*c* creates heat and friction. A flush flow of fluid is provided accordingly to lubricate the translational and rotational movement of piston 70*p* within cylinder 70*c*. The flush flow of fluid, e.g., reverse osmosis, distilled or deionized water, is provided at flush flow ports 70*a* and 70*b* to contact piston 70*p* as it is moved translationally and rotationally within cylinder 70*c*. The flush flow of fluid may be circulated or stagnant.

System 210 of FIGS. 28 and 29 provides water tank 230. It is contemplated to provide a column of water (not illustrated) extending from water tank 230 so as to contact the needed lubrication areas or portions of piston 70*p* via flush flow ports 70*a* and 70*b*. FIGS. 31 and 32 illustrate alternative embodiments for using the water in water tank 230 of system 210 for providing a flush flow to flush flow ports 70*a* and 70*b* of piston pump 70. System 210 in FIGS. 31 and 32 includes each of the structures, functionality and alternatives of like numbered components of system 210 of FIGS. 28 and 29. In particular, system 210 in FIGS. 31 and 32 includes control unit 100, valves 254*a* to 254*h*, lines 252*a* to 252*d*, disinfection and water cleaning circuit 250, heater 56, air trap 60, PD fluid pump 70, flowmeter 226, conductivity sensor 74, pressure sensor 78*a*, alternative single lumen patient line connector 132 extending from housing 222 of cycler 220, single lumen reusable patient line 128 including distal end 128*d* and drain line connector 34, which have each been described above.

System 210 of FIG. 31 does not include tank line 252*c* or three-way valve 254*i* connecting to line 252*c* discussed in connection with FIGS. 28 and 29 but does include a three-way valve 254*j* in fluid communication with flush flow port 70*a*, line 252*a* and an additional line 252*f* leading to a flush flow pump 350 (which may be any type of pump discussed herein and is in one embodiment a micropump) under control of control unit 100. System 210 of FIG. 32 has a corresponding three-way valve 254*j* but also provides three-way valve 254*i* connecting to line 252*c*. System 210 of both FIGS. 31 and 32 provides a secondary flush flow chamber 260, which holds whatever type of fluid is held within disinfection tank 230, e.g., a fluid suitable for both disinfection and flush flow, e.g., reverse osmosis, distilled or deionized water.

System 210 of both FIGS. 31 and 32 includes a two-way valve 254*k* located between recirculation/flush flow pump 350 and flush flow chamber 260. A line 252*e* having two-way valve 254*l* extends from disinfection or water tank 230 to flush flow chamber 260. A line 252*g* extends from flush flow chamber 260 to flush flow port 70*b* of PD fluid pump 70. A line 252*h* extends from flush flow chamber 260 to disinfection line valve 254*c* leading to drain line connector 34.

The provision of both three-way valves 254*i* and 254*j* in system 210 of FIG. 32 allows for a greater volume of water, perhaps all, to be included in the disinfection sequence. In system 210 of FIG. 31, a smaller volume such as a fraction of the full volume of water, is disinfected. The fluid of the smaller volume disinfection is not the same from time to time, however, over multiple sequences all water of FIG. 31 is at some point disinfected and cleaned.

During patient fills and drains, control unit 100 causes flush flow valve 254*k* to be open and three-way valve 254*j* to be oriented such that flush flow water is circulated from flush flow port 70*a* of pump 70 via pump 350 back into flush flow tank 260 via line 252*f*. Water is pumped from flush flow tank 260 via line 252*g* to flush flow port 70*b* of pump 70. Valves 254*l*, 254*c* and 254*h* and their associated lines are closed.

For disinfection using system 210 of FIGS. 31 and 32, the flush flow just described is provided while PD fluid pump 70 is actuated. It is contemplated to first have user interface 108 prompt the user to connect reusable patient line 128 to single lumen patient line connector 132 and then for control unit 100 to cause pump 70 to pump as much used PD fluid to drain 36 as possible with the drain line connected to drain line connector 34. In an alternative embodiment, control unit 100 may also cause disinfection (flush flow) water to, in addition, rinse any residual PD fluid to drain. In either case, air may be backfilled into water cleaning circuit 250 via vent valve 254*e* to leave the circuit primarily full of air. Next, user interface 108 prompts the user to remove drain line 36 from drain line connector 34. Control unit 100 then opens all two-way valves (including tank/chamber valve 254*l*) except drain valve 254*f* and runs pump 70 to fill disinfection circuit 250 with disinfection/flush flow water. Here, three-way valve 254*j* (FIG. 31) or 254*i* (FIG. 32) is oriented to isolate disposable cleaning cartridge 240.

Then, in one embodiment, with disinfection circuit 250 filled with disinfection/flush flow water, control unit 100 runs a water cleaning phase in which all valves are closed except flush flow valve 254*k*, tank/chamber valve 254*l*, and wherein three-way valves 254*j* and 254*i* are oriented such that water circulates through cleaning cartridge 240. Pump 350 is operated to circulate all of the water in water tank 230 a number of times sufficient to adequately clean the water. PD fluid pump 70 is not actuated and thus does not need flush flow. The reason for running water cleaning phase before the heated portion of the disinfection sequence is to avoid mixing water that is to be used for disinfection with the cleaned water. Also, using smaller flush flow chamber 260 as the source for disinfection water uses less energy to disinfect cycler 220, and since the disinfection volume is a smaller volume, the disinfection time is lessened.

After the water cleaning phase is completed, control unit 100 closes tank/chamber valve 254*l* and reorients three-way valves 254*j* and 254*i* such that water does not circulate through cleaning cartridge 240. Pump 70 and heater 56 are actuated, flush flow is provided, and the disinfection of disinfection circuit 250 takes place according to any of the embodiments discussed herein.

As discussed above, systems 10*a* to 10*d* in one embodiment use dialysis fluid for disinfection and do not provide or require a separate water source. The glucose or dextrose provided with the dialysis fluid, however, makes the dialysis fluid unsuitable for use as a flushing fluid for dialysis fluid pump 70. It is expressly contemplated to provide flush flow tank 260 holding any type of flush flow water discussed herein, line 252*h* to flush flow port 70*b*, line 252*f* from flush flow port 70*a*, recirculation/flush flow pump 350, flush flow valve 254*k* and possibly flush flow drain line 252*h* to either or any of systems 10*a* to 10*d*. Here water tank 230 is not provided. The patient or caregiver instead periodically tops off flush flow tank 260 with flush flow water, e.g., via a resealable lid. Control unit 100 of system 210 is programmed in one embodiment to open flush flow valve 254*k* and run pump 350 whenever dialysis fluid pump 70 is actuated.

Figure 33:
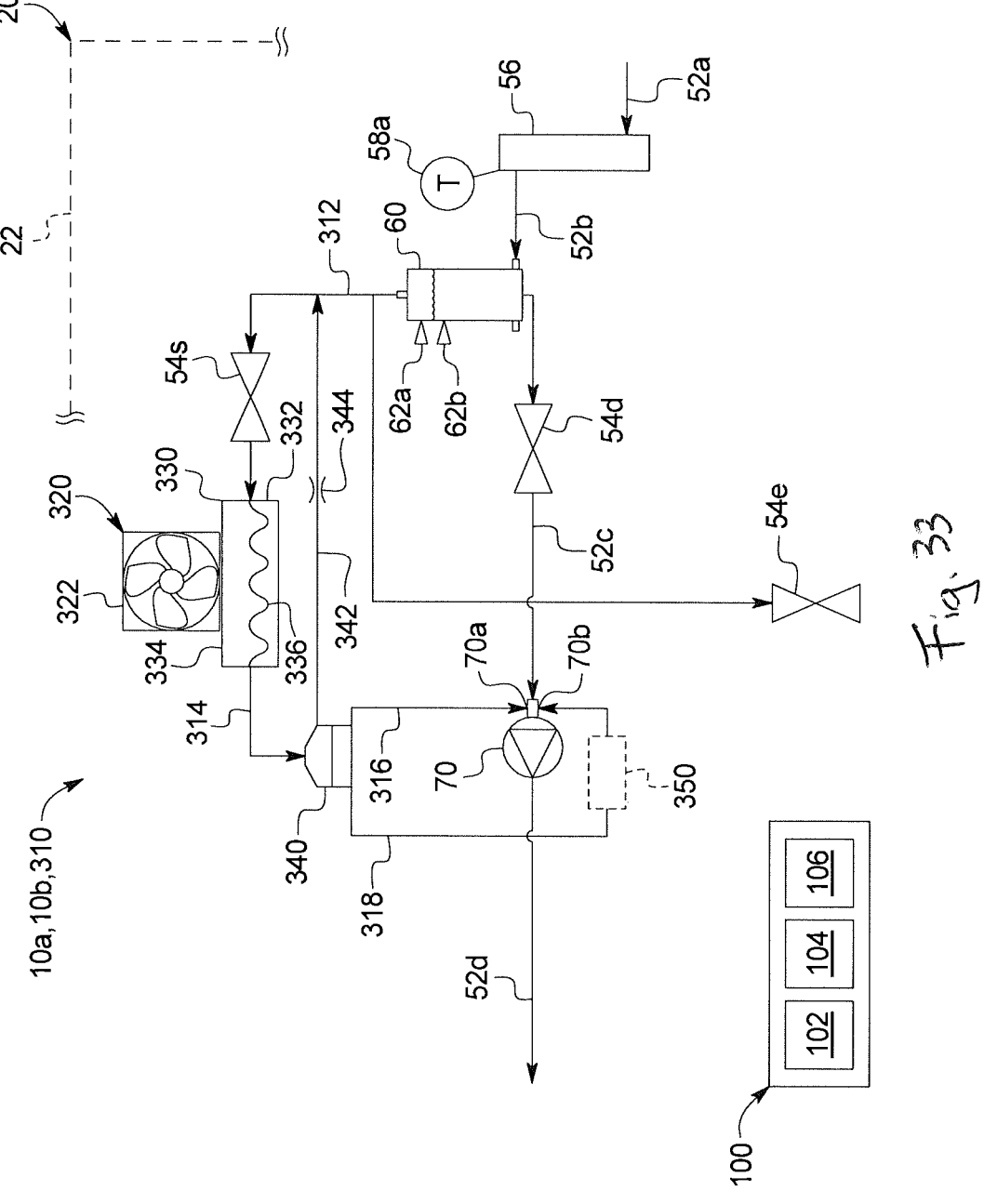
FIG. 33 is a schematic view of one embodiment for a water production subsystem of the present disclosure, which many be used for producing flush flow water for lubricating the dialysis fluid pumps of the present disclosure.

Referring now to FIG. 33, various embodiments for an alternative flush flow solution are illustrated, which includes a water production subsystem 310, which may be used with systems 10*a* to 10*d*, wherein peritoneal dialysis fluid is used for disinfection in one embodiment, and such that a separate source of water is not needed. Subsystem 310 in the illustrated embodiment uses heater 56 operable with temperature sensor 58*a*, container or air trap 60 operable with level sensors 62*a* and 62*b* and vent valve 54*e*, container or air trap valve 54*d* and dialysis fluid pump 70, including each of the structures, functionality and alternatives for those components discussed herein. Subsystem 310 also includes a steam line 312 that extends from container or air trap 60 through a steam valve 54*s* to a condenser 320. The steam is condensed in condenser 320 to form distilled water, which flows, e.g., via gravity, to a collection chamber 340. Collection chamber 340 provides flush flow water as needed to flush flow ports 70*a* and 70*b* of dialysis fluid pump 70. Flush flow ports 70*a* and 70*b* are located at an area of dialysis fluid pump 70 needing lubrication and possibly cooling. Each of the above components, including any electrical parts of condenser 320, is under the control of and/or outputs to control unit 100 of cycler 20.

Condenser 320 may be provided in a plurality of ways. In one embodiment, condenser 320 includes a fan 322 and a fluid carrying structure that forces the steam to remain in an air flow area of fan, for example, a reusable conductive (e.g., stainless steel) coil. In another embodiment, condenser 320 includes a thermoelectric cooler 330, which may be a Peltier device or module. Peltier module 330 may be viewed as a solid-state active heat pump, which transfers heat from one side of the module to the other side of the module via the consumption of electrical energy.

Thermoelectric performance of thermoelectric cooler 330 is a function of ambient temperature, thermal load, the geometry of thermoelectric cooler 330 (e.g., Peltier geometry), and the electrical parameters of thermoelectric cooler 330 (e.g., Peltier electrical parameters). The amount of heat that is moved via thermoelectric cooler 330 is proportional to electrical current delivered to the cooler via control unit 100 and time. The cooling effect in one implementation is described by Equation 1 where (Q) is the cooling effect in Watts [W], (P) is the Peltier coefficient, (I) is the current and (t) is the time.

$$Q=PIt \qquad \text{Equation 1}$$

The Peltier coefficient (P) depends on the temperature and materials from which the Peltier module is made. Peltier modules may be made of two dissimilar materials, which are typically semi-conductors. The materials may be placed thermally in parallel and electrically in series and may be joined by thermal plates to allow heat to flow from one side of the module to the other when an electric current or an electromagnetic field is applied to the module. In the illustrated embodiment, heat is transferred from the cooled side 332 of Peltier module 330 to the warmed side 334.

In the illustrated embodiment, a condensing pathway 336 is formed in the cooled side 332 of Peltier module 330, which receives steam from steam line 312 and outputs distilled water to collection chamber 340 via distilled water line 314. Condensing pathway 336 may be a serpentine pathway that increases contact time with the cooled side 332 of Peltier module 330. While condensing pathway 336 is illustrated as extending through cooled side 332 of Peltier module 330, condensing pathway 336 may be located alternatively on the underside and in thermal contact with cooled side 332. Condensing pathway may 336 accordingly be made of a reusable conductive material, such as stainless steel. FIG. 33 further illustrates that condenser 320 may also provide fan 322 under control of control unit 100 at the warmed side 334 of Peltier module 330 to convect heat away from the warmed side 334, increasing the efficiency of Peltier module 330. To this end, the warmed side 334 of Peltier module 330 may be provided with heat fins (not illustrated), which may be cooled via fan 322. Although not illustrated, it is contemplated to communicate warmed side 334 of Peltier module 330 with container or air trap 60 to recoup some of the heat generated at module 330, e.g., via thermal contact. Alternatively, tubing or line 52a running to heater 56 may run through or along the top of warmed side 334 of Peltier module 330.

In the illustrated embodiment, distilled water free flows to collection chamber 340, filling the chamber, which may for example hold 10 ml or less of distilled water. Distilled water flows from collection chamber 340 into either of, or both of, flush flow lines 316 and 318 that extend and connect sealingly to flush flow ports 70a and 70b, respectively, of dialysis fluid pump 70. Once chamber 340 and flush flow lines 316 and 318 are filled with distilled water, additional distilled water flows from condenser 320 back to container or air trap 60 via return line 342. In an embodiment, a flow restrictor 344 is located along return line 342 to initially resist flow through the restrictor until chamber 340 and flush flow lines 316 and 318 are filled with distilled water. Return line 342 is illustrated as connecting to steam line 312 to return distilled water to container or air trap 60. In an alternative embodiment, return line 342 extends directly to container or air trap 60.

In the illustrated embodiment for water production subsystem 310, the arrows of flush flow lines 316 and 318 are both pointing towards their respective flush flow ports 70a and 70b of dialysis fluid pump 70, indicating that the lines are statically filled with distilled water under head pressure from chamber 340. In this way, the lubrication-needing portions or areas of dialysis fluid pump 70 are under constant contact with distilled water. In an alternative and perhaps preferred embodiment, a small flush fill pump 350, e.g., micropump, under control of control unit 100 is located along one of flush flow lines 316 or 318 to recirculate the distilled water from chamber 340 to one of flush flow ports 70a or 70b and from the other flush flow port back to chamber 340. Here, the arrow of the return flush flow line 316 or 318 points instead towards chamber 340. Flush fill pump 350 may also be used during the preparation of the distilled water to recirculate the distilled water in an effort to return residual water from the previous treatment to container or air trap 60. Flush fill pump 350 may further be used to create a negative pressure to accelerate the vaporization during the distillation phase.

Under normal operation, e.g., during priming, draining or filling, steam valve 54s is closed and dialysis fluid pump 70 operates with the flush flow of distilled water just described. In one embodiment, at the end of disinfection when the disinfection fluid is already heated, steam valve 54s is opened before energizing heater 56, in one embodiment, to allow residual water from the previous treatment to gravity flow from chamber 340 into container or air trap 60. Heater 56, with air trap valve 54d closed, steam valve 54s open and container or air trap 60 full, as indicated by the output from upper level sensor 62a, is then energized additionally to heat or otherwise create steam or high water-containing air from the already heated disinfection fluid, e.g., dialysis fluid. The steam rising from the heated disinfection fluid within container or air trap 60 is free not only of glucose or dextrose contained in the dialysis fluid but also of fibrin, proteins, fats and other solid particles and liquid impurities contained in the disinfection fluid at the end of disinfection. The steam condenses into distilled and purified water via thermoelectric cooler 330 and collection chamber 340 as described above, which is well suited for flush flow.

In another embodiment, control unit 100 is operated such that steam valve 54s is opened during disinfection while energizing heater 56 to allow residual water from the previous treatment to gravity flow from chamber 340 into container or air trap 60. With air trap 60 full as indicated by the output from upper level sensor 62a, liquid within air trap 60 is energized additionally to heat or otherwise create steam or high water-containing air from the already heated disinfection fluid, e.g., dialysis fluid. The steam rising from the heated disinfection fluid within container or air trap 60 is again free of impurities contained in the disinfection fluid. The steam condenses into distilled and purified water via thermoelectric cooler 330 and collection chamber 340 as described above, which is well suited for flush flow.

Figure 34:
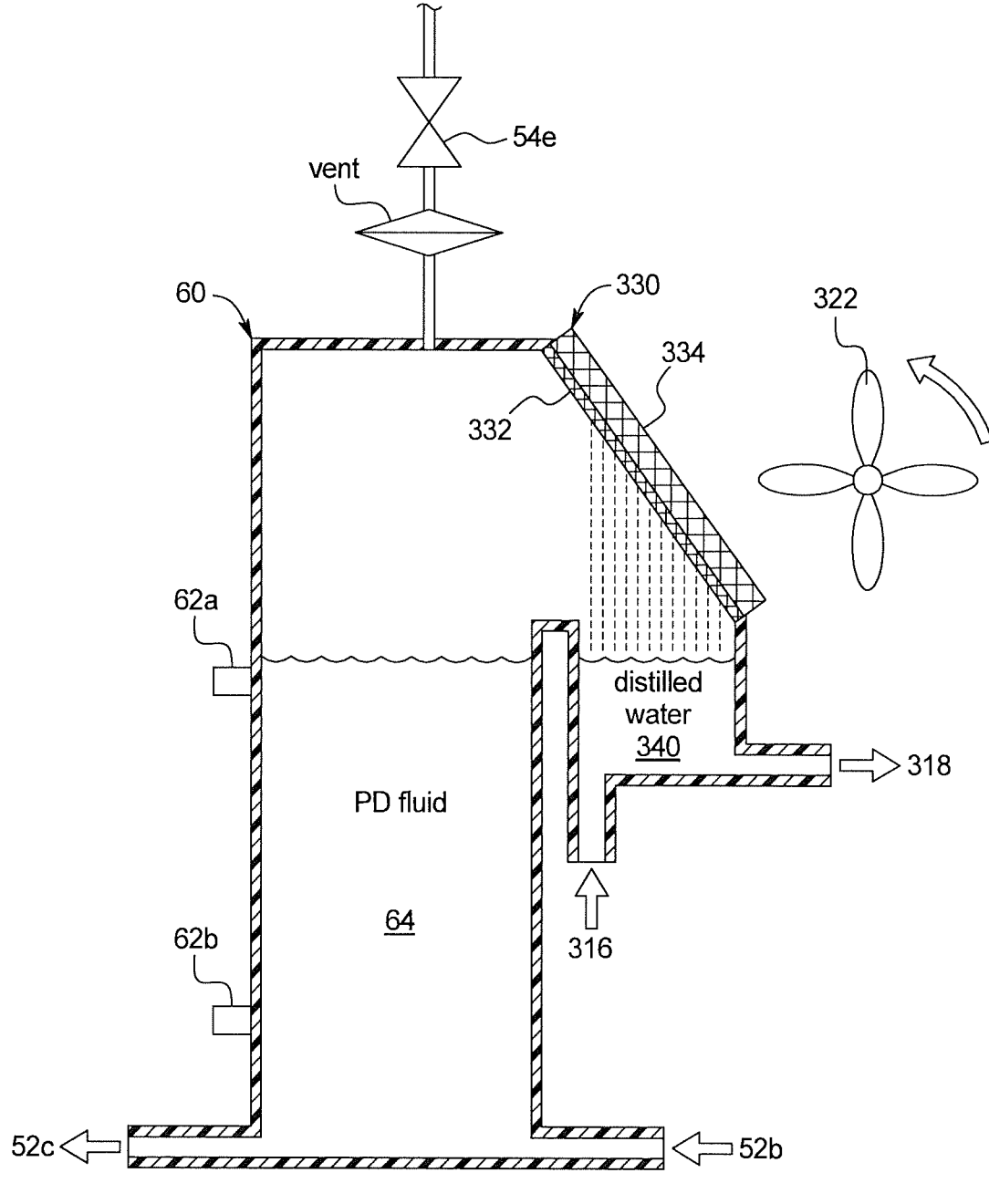
FIG. 34 is a sectioned elevation view for an alternative combined air trap and distilled water collection chamber useable with the water production subsystem of FIG. 33.

Referring now to FIG. 34, an alternative structure for water production subsystem 310 is illustrated, in which thermoelectric cooler 330 and collection chamber 340 are combined with air trap 60. Air trap 60 in the illustrated embodiment receives fresh PD fluid from PD fluid line 52b, fresh PD fluid exits air trap 60 via PD fluid line 52c, and air trap 60 is vented through a hydrophobic vent via vent valve 54e. Air trap 60 includes a primary chamber 64 that holds fresh PD fluid, which has been heated by heater 56 to a temperature sufficient to cause steam, water vapor or heavily water-laden air to rise above the PD fluid level (as maintained by level sensors 62a and 62b). Thermoelectric cooler 330 (e.g., Peltier module, FIG. 33) under control of control unit 100 is provided at the top of air trap 60, e.g., at an angle, and is located above distilled water collection chamber 340. Thermoelectric cooler 330 as discussed above includes a cooled side 332 and a warmed side 334 that is cooled by a fan 322 under control of control unit 100 to increases the effectiveness of the thermoelectric cooler.

Thermoelectric cooler 330 is affixed to or molded into an opening formed in air trap 60 such that cooled side 332 faces the steam or heavily water-laden air, which is condensed by the cooled side 332. Water droplets may be formed on the angled surface of cooled side 332 and run via gravity down the surface into distilled water collection chamber 340. The water droplets may alternatively or additionally fall through the air into water collection chamber 340. Water collection chamber 340 in the illustrated embodiment is separated from primary chamber 64 of air trap 60 via an air gap to mitigate conductive heat transfer from the heated PD fluid and the reheating of the distilled water.

Water collection chamber 340 in the illustrated embodiment is provided with ports that connect to flush flow lines 316 and 318. As illustrated in FIG. 33, a flush flow pump 350 (e.g., micropump) under control of control unit 100 is optionally provided to pump distilled water, e.g., via flush flow line 318 from water collection chamber 340, through flush flow ports 70a and 70b of pump 70 and back to water collection chamber 340 via line 316.

In a further alternative embodiment, it is contemplated to configure thermoelectric cooler 330 such that warmed side 334 is positioned to act as a heat pump that helps to heat the PD fluid to form water vapor. Here, the heat is used instead of being discarded and fan 322 is not needed, resulting in an overall more energy efficient water production subsystem 310. It should be appreciated that cooled side 332 is still positioned to condense the water vapor as described herein.

Thermoelectric cooler or Peltier module 330 has been described in connection with creating distilled water for flush flow. It is contemplated to alternatively or additionally use thermoelectric cooler or Peltier module 330 to heat dialysis fluid instead of an electric or resistive inline heater contemplated for dialysis fluid inline heater 56. Thermoelectric cooler or Peltier module 330 is quiet and does not require its control board to be fan-cooled. Thermoelectric cooler or Peltier module 330 also provides a cool side, which can be used to cool and prolong the life of the electronics associated with control unit 100. Thermoelectric cooler or Peltier module 330 also provides a built-in safety because the modules lose their ability to move energy if a temperature difference becomes too great. Thus, if a problem occurs and cycler 10a, 10b or 210 becomes stuck and tries to overheat, Peltier module 330 will stop at its maximum temperature difference.

It should also be understood that other changes and modifications to the presently preferred embodiments described herein are covered by the appended claims. For example, while the drain line is illustrated and described as being disposable, the drain line may alternatively be reusable, wherein an additional disinfection connector is provided for the drain line to connect to the disinfection loop for the disinfection sequence. Also, while heat disinfection is disclosed, chemical disinfection, e.g., citric acid, may be provided alternatively or in addition to heat disinfection. There may be chemical benefits to using used dialysis fluid as a disinfectant. Additionally, while the present disclosure discusses the provision of a final stage filter in the fresh disposable line, a second filter may be provided in the used disposable line, e.g., a course filter to remove fibrin or other effluent artifacts from the used dialysis fluid. Other types of disinfection, e.g., ultraviolet light, may be used additionally. Further, while the systems discussed herein show the patient line being reusable and the drain line being disposable, it is contemplated to alternatively make the drain line reusable (e.g., single lumen where both ends plug into cycler 20 or dual lumen like dual lumen patient line 28) and the patient line disposable, or to make both the patient and drain lines reusable.

The invention is claimed as follows:

1. A peritoneal dialysis system comprising:
   a housing;
   a dialysis fluid pump housed by the housing and including a reusable pump body that accepts PD fluid for pumping;
   a dialysis fluid inline heater housed by the housing and including a reusable heater body that accepts PD fluid for heating;
   at least one reusable PD fluid line extending from the housing;
   at least one disinfection connector supported by the housing and configured to accept one of the at least one reusable PD fluid line;
   a control unit configured to run a disinfection sequence after a PD treatment, wherein each of the at least one reusable PD fluid line is connected to one of the at least one disinfection connectors, and wherein at least one of the dialysis fluid pump and the dialysis fluid inline heater is actuated during the disinfection sequence;
   at least one of a reusable patient line or reusable drain line and at least one of
      (i) a patient line connector supported by the housing, the patient line connector configured to accept the reusable patient line for running the disinfection sequence, or
      (ii) a drain line connector supported by the housing, the drain line connector configured to accept the reusable drain line for running the disinfection sequence; and
   at least one spool located within the housing, the at least one spool configured to automatically retract at least one of (i) the reusable patient line when the patient line is connected to the patient line connector or (ii) the reusable drain line when the drain line is connected to the drain line connector.

2. The PD system of claim 1, wherein the control unit is configured to cause (i) the dialysis fluid inline heater to heat the PD fluid to at least 70° C. and (ii) the dialysis fluid pump to recirculate the heated PD fluid during the disinfection sequence.

3. The PD system of claim 1, wherein the dialysis fluid pump is a piston, gear, membrane or centrifugal pump, the reusable pump body of the piston, gear, membrane or centrifugal pump accepting PD fluid for pumping.

4. The PD system of claim 1, wherein the dialysis fluid pump is volumetrically inherently accurate.

5. The PD system of claim 1, which includes a pressure sensor located downstream from the dialysis fluid pump, the pressure sensor providing pressure feedback to the control unit, the pressure feedback used by the control unit to control a pressure of the PD fluid pumped by the dialysis fluid pump.

6. The PD system of claim 5, wherein the control unit controls electrical current to the dialysis fluid pump to control the pressure of the PD fluid.

7. The PD system of claim 1, which includes a temperature sensor located downstream from the dialysis fluid inline heater, the temperature sensor providing temperature feedback to the control unit, the temperature feedback used by the control unit to control a temperature of the PD fluid heated by the dialysis fluid inline heater.

8. The PD system of claim 1, which includes an air trap located downstream from the dialysis fluid inline heater, the air trap configured to collect air removed from dialysis fluid heated by the dialysis fluid inline heater and/or from a PD fluid container.

9. The PD system of claim 8, which includes at least one level sensor positioned and arranged to detect dialysis fluid within the air trap, the at least one level sensor providing an output to the control unit, the control unit configured to use the output to control a dialysis fluid level within the air trap.

10. The PD system of claim 1, which includes a conductivity sensor in fluid communication with the dialysis fluid pump, the conductivity sensor providing an output to the control unit, the control unit configured to use the output to at least one of (i) ensure fresh PD fluid is of a prescribed type or (ii) analyze used PD fluid for treatment effectiveness and/or patient disease.

11. The PD system of claim 1, which includes a plurality of dialysis fluid valves, each dialysis fluid valve including a reusable valve body that occludes or allows PD fluid to flow through the reusable valve body, the plurality of valves including at least one of (i) at least one first valve between each of the at least one reusable PD fluid lines and the dialysis fluid inline heater, (ii) a second valve between the dialysis fluid inline heater and the dialysis fluid pump, or (iii) at least one third valve provided along a disinfection line in fluid communication with the at least one disinfection connector.

12. The PD system of claim 1, wherein the reusable patient line is a dual lumen patient line.

13. The PD system of claim 1, which includes a disposable filter set configured to interface between the reusable patient line and a patient's transfer set, the disposable filter set providing a final stage of PD fluid filtration prior to delivery to the patient, and wherein the final stage of PD fluid filtration is optionally sterile filtration.

14. The PD system of claim 1, wherein at least one of (i) the reusable patient line when plugged into the patient line connector forms part of a disinfection loop for the disinfection sequence or (ii) the reusable patient line is coated with a non-sticking or smooth coating.

15. The PD system of claim 14, wherein the disinfection loop further includes at least one of (i) a first fluid line leading from the at least one reusable PD fluid line to the reusable heater body, (ii) a second fluid line leading from the reusable heater body to the reusable pump body, or (iii) a third fluid line leading from the reusable pump body to the reusable patient line.

16. The PD system of claim 1, which includes a dual lumen connector allowing a disinfection loop to be formed with an associated line removed from the connector, wherein the connector is optionally a drain line connector.

17. The PD system of claim 1, which includes a source of flush flow fluid and at least one flush flow line for communicating the flush flow fluid from the source to the dialysis fluid pump, wherein the source of flush flow fluid includes a mechanism to heat PD fluid to form steam or water vapor, and a condenser for condensing the steam or water vapor into the flush flow fluid.

18. The PD system of claim 1, which includes at least one of a flow switch or a pressure sensor positioned between the dialysis fluid pump and the at least one reusable PD fluid line, and wherein the control unit is configured to use at least one output from the at least one flow switch or pressure sensor to detect an empty or no flow condition of a PD fluid container in fluid communication with one of the at least one reusable PD fluid line.

19. The PD system of claim 18, wherein the control unit is further configured to use an output from the pressure sensor in a fluid volume delivered determination for the dialysis fluid pump.

20. A peritoneal dialysis ("PD") system comprising:
a housing;
a dialysis fluid pump housed by the housing and including a reusable pump body that accepts PD fluid for pumping;
a dialysis fluid inline heater housed by the housing and including a reusable heater body that accepts PD fluid for heating;
a reusable patient line extending from the housing;
a patient line connector supported by the housing, the patient line connector configured to accept the patient line for running disinfection sequence;
a control unit configured to run a disinfection sequence after a PD treatment, wherein the reusable patient line is connected to the patient line connector, and wherein the dialysis fluid pump and the dialysis fluid inline heater are actuated during the disinfection sequence;
a patient line connector supported by the housing, the patient line connector configured to accept the reusable patient line for running the disinfection sequence; and
at least one spool located within the housing, the at least one spool configured to automatically retract the reusable patient line when the patient line is connected to the patient line connector.

21. The PD system of claim 20, wherein the control unit is configured to cause (i) the dialysis fluid inline heater to heat the PD fluid to at least 70° C. and (ii) the dialysis fluid pump to recirculate the heated PD fluid during the disinfection sequence.

22. The PD system of claim 20, which includes a disposable filter set configured to interface between the reusable patient line and a patient's transfer set, the disposable patient filter set providing at least one of (i) a final stage of PD fluid filtration prior to delivery to the patient, wherein the final stage of PD fluid filtration is optionally sterile filtration, or (ii) a final stage of air removal from the PD fluid prior to delivery to the patient.

23. The PD system of claim 22, wherein the disposable filter set includes a final stage filter located along a first disposable line and which includes a second disposable line operating in parallel with the first disposable line.

24. The PD system of claim 23, wherein the reusable patient line is a dual lumen patient line including a first lumen in fluid communication with the first disposable line and a second lumen in fluid communication with the second disposable line.

25. The PD system of claim 20, which includes a source of flush flow fluid and at least one flush flow line for communicating the flush flow fluid from the source to the dialysis fluid pump.

26. The PD system of claim 20, which includes a leak detection sensor and a leak detection pan located at a bottom of the housing, the leak detection pan formed so as to collect leaked PD fluid at a location detectable by the leak detection sensor.

* * * * *